US009211382B2

(12) United States Patent
Hale et al.

(10) Patent No.: US 9,211,382 B2
(45) Date of Patent: *Dec. 15, 2015

(54) DRUG CONDENSATION AEROSOLS AND KITS

(75) Inventors: Ron L. Hale, Woodside, CA (US);
Craig C. Hodges, Walnut Creek, CA (US); Peter M. Lloyd, Walnut Creek, CA (US); Amy T. Lu, Los Altos, CA (US); Daniel J. Myers, Mountain View, CA (US); Joshua D. Rabinowitz, Princeton, NJ (US); Martin J. Wensley, Los Gatos, CA (US); Jeffrey A. McKinney, Lafayette, CA (US); Alejandro C. Zaffaroni, Atherton, CA (US)

(73) Assignee: Alexza Pharmaceuticals, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/569,006

(22) Filed: Aug. 7, 2012

(65) Prior Publication Data

US 2013/0032139 A1    Feb. 7, 2013

Related U.S. Application Data

(63) Continuation of application No. 12/117,737, filed on May 8, 2008, now Pat. No. 8,235,037, which is a (Continued)

(51) Int. Cl.
| | |
|---|---|
| *A61K 9/12* | (2006.01) |
| *A61K 9/14* | (2006.01) |
| *A61M 15/00* | (2006.01) |
| *H05B 3/00* | (2006.01) |
| *A61M 11/04* | (2006.01) |
| *A61K 9/00* | (2006.01) |
| *A61K 31/4468* | (2006.01) |
| *A61K 31/519* | (2006.01) |
| *A61K 31/5415* | (2006.01) |
| *A61K 31/5517* | (2006.01) |
| *A61K 31/553* | (2006.01) |

(52) U.S. Cl.
CPC .............. *A61M 11/04* (2013.01); *A61K 9/0004* (2013.01); *A61K 9/007* (2013.01); *A61K 9/0078* (2013.01); *A61K 31/4468* (2013.01); *A61K 31/519* (2013.01); *A61K 31/5415* (2013.01); *A61K 31/553* (2013.01); *A61K 31/5517* (2013.01); *A61M 11/041* (2013.01); *A61M 11/042* (2014.02); *A61M 11/047* (2014.02); *A61M 15/00* (2013.01)

(58) Field of Classification Search
CPC ..... A61B 12/006; A61M 15/00; A61K 9/007; A61K 11/047

See application file for complete search history.

(56) References Cited

U.S. PATENT DOCUMENTS

| | | | |
|---|---|---|---|
| 1,239,634 | A | 9/1917 | Stuart |
| 1,535,486 | A | 4/1925 | Lundy |
| 1,803,334 | A | 5/1931 | Lehmann |
| 1,864,980 | A | 6/1932 | Curran |
| 2,084,299 | A | 6/1937 | Borden |
| 2,086,140 | A | 7/1937 | Ernst |
| 2,230,753 | A | 2/1941 | Klavehn et al. |
| 2,230,754 | A | 2/1941 | Klavehn et al. |
| 2,243,669 | A | 5/1941 | Clyne |
| 2,309,846 | A | 2/1943 | Holm |
| 2,469,656 | A | 5/1949 | Lienert |
| 2,714,649 | A | 8/1955 | Critzer |
| 2,741,812 | A | 4/1956 | Andre |
| 2,761,055 | A | 8/1956 | Ike |
| 2,887,106 | A | 5/1959 | Robinson |
| 2,898,649 | A | 8/1959 | Murray |
| 2,902,484 | A | 9/1959 | Horclois |
| 3,043,977 | A | 7/1962 | Morowitz |
| 3,080,624 | A | 3/1963 | Webber, III |

(Continued)

FOREIGN PATENT DOCUMENTS

| | | |
|---|---|---|
| CA | 2152684 | 1/1996 |
| CN | 1082365 | 2/1994 |

(Continued)

OTHER PUBLICATIONS

Office Action mailed Jan. 26, 2007 with respect to U.S. Appl. No. 10/057,198.
Office Action mailed Jul. 3, 2006 with respect to U.S. Appl. No. 10/057,198.
Office Action mailed Sep. 20, 2005 with respect to U.S. Appl. No. 10/057,198.
Office Action mailed Dec. 04, 2003 with respect to U.S. Appl. No. 10/057,198.
Office Action mailed Jan. 12, 2005 with respect to U.S. Appl. No. 10/057,197.

(Continued)

*Primary Examiner* — Mina Haghighatian
(74) *Attorney, Agent, or Firm* — Swanson & Bratschun, L.L.C.

(57) ABSTRACT

The present invention provides novel condensation aerosols for the treatment of disease and/or intermittent or acute conditions. These condensation aerosols have little or no pyrolysis degradation products and are characterized by having an MMAD of between 1-3 microns. These aerosols are made by rapidly heating a substrate coated with a thin film of drug having a thickness of between 0.05 and 20 μm, while passing a gas over the film, to form particles of a desirable particle size for inhalation. Kits comprising a drug and a device for producing a condensation aerosol are also provided, wherein the device, has an element for heating the drug which is coated as a film on the substrate and contains a therapeutically effective dose of a drug when the drug is administered in aerosol form, and an element allowing the vapor to cool to form an aerosol. Methods for use are also disclosed.

36 Claims, 19 Drawing Sheets

Related U.S. Application Data continuation of application No. 11/504,419, filed on Aug. 15, 2006, now abandoned, which is a continuation of application No. 10/718,982, filed on Nov. 20, 2003, now Pat. No. 7,090,830, which is a continuation-in-part of application No. 10/057,197, filed on Oct. 26, 2001, now Pat. No. 7,766,013, said application No. 10/718,982 is a continuation-in-part of application No. 10/057,198, filed on Oct. 26, 2001, now abandoned, said application No. 10/718,982 is a continuation-in-part of application No. 10/146,080, filed on May 13, 2002, now Pat. No. 7,942,147, which is a continuation-in-part of application No. 10/057,198, filed on Oct. 26, 2001, now abandoned, said application No. 10/718,982 is a continuation-in-part of application No. 10/146,086, filed on May 13, 2002, now Pat. No. 7,458,374, and a continuation-in-part of application No. 10/146,088, filed on May 13, 2002, now Pat. No. 7,537,009, which is a continuation-in-part of application No. 10/057,198, filed on Oct. 26, 2001, now abandoned, said application No. 10/718,982 is a continuation-in-part of application No. 10/146,515, filed on May 13, 2002, now Pat. No. 6,682,716, which is a continuation-in-part of application No. 10/057,198, filed on Oct. 26, 2001, now abandoned, said application No. 10/718,982 is a continuation-in-part of application No. 10/146,516, filed on May 13, 2002, now Pat. No. 6,737,042, said application No. 10/718,982 is a continuation-in-part of application No. 10/150,056, filed on May 15, 2002, now Pat. No. 6,805,853, said application No. 10/718,982 is a continuation-in-part of application No. 10/150,267, filed on May 15, 2002, now Pat. No. 6,797,259, said application No. 10/718,982 is a continuation-in-part of application No. 10/150,268, filed on May 15, 2002, now Pat. No. 6,780,399, said application No. 10/718,982 is a continuation-in-part of application No. 10/150,591, filed on May 17, 2002, now Pat. No. 6,780,400, said application No. 10/718,982 is a continuation-in-part of application No. 10/150,857, filed on May 17, 2002, now Pat. No. 6,716,415, said application No. 10/718,982 is a continuation-in-part of application No. 10/151,596, filed on May 16, 2002, now Pat. No. 6,855,310, said application No. 10/718,982 is a continuation-in-part of application No. 10/151,626, filed on May 16, 2002, now Pat. No. 6,783,753, said application No. 10/718,982 is a continuation-in-part of application No. 10/152,639, filed on May 20, 2002, now Pat. No. 6,716,416, said application No. 10/718,982 is a continuation-in-part of application No. 10/152,640, filed on May 20, 2002, now Pat. No. 6,743,415, said application No. 10/718,982 is a continuation-in-part of application No. 10/152,652, filed on May 20, 2002, now Pat. No. 6,740,307, said application No. 10/718,982 is a continuation-in-part of application No. 10/153,139, filed on May 20, 2002, now Pat. No. 6,814,954, said application No. 10/718,982 is a continuation-in-part of application No. 10/153,311, filed on May 21, 2002, now Pat. No. 6,884,408, said application No. 10/718,982 is a continuation-in-part of application No. 10/153,313, filed on May 21, 2002, now abandoned, said application No. 10/718,982 is a continuation-in-part of application No. 10/153,831, filed on May 21, 2002, now Pat. No. 6,740,308, said application No. 10/718,982 is a continuation-in-part of application No. 10/153,839, filed on May 21, 2002, now Pat. No. 6,776,978, said application No. 10/718,982 is a continuation-in-part of application No. 10/154,594, filed on May 23, 2002, now Pat. No. 6,740,309, said application No. 10/718,982 is a continuation-in-part of application No. 10/154,765, filed on May 23, 2002, now Pat. No. 6,814,955, said application No. 10/718,982 is a continuation-in-part of application No. 10/155,097, filed on May 23, 2002, now Pat. No. 6,716,417, said application No. 10/718,982 is a continuation-in-part of application No. 10/155,373, filed on May 22, 2002, now Pat. No. 6,737,043, said application No. 10/718,982 is a continuation-in-part of application No. 10/155,621, filed on May 22, 2002, now Pat. No. 6,759,029, said application No. 10/718,982 is a continuation-in-part of application No. 10/155,703, filed on May 22, 2002, now Pat. No. 6,803,031, said application No. 10/718,982 is a continuation-in-part of application No. 10/155,705, filed on May 22, 2002, now Pat. No. 6,805,854, said application No. 10/718,982 is a continuation-in-part of application No. 10/280,315, filed on Oct. 25, 2002, now abandoned, said application No. 10/718,982 is a continuation-in-part of application No. 10/302,010, filed on Nov. 21, 2002, now Pat. No. 7,078,016, said application No. 10/718,982 is a continuation-in-part of application No. 10/302,614, filed on Nov. 21, 2002, now abandoned, said application No. 10/718,982 is a continuation-in-part of application No. 10/322,227, filed on Dec. 17, 2002, now abandoned, said application No. 10/718,982 is a continuation-in-part of application No. 10/633,877, filed on Aug. 4, 2003, now Pat. No. 7,585,493, said application No. 10/718,982 is a continuation-in-part of application No. 10/633,876, filed on Aug. 4, 2003, now Pat. No. 7,645,442.

(60) Provisional application No. 60/296,225, filed on Jun. 5, 2001, provisional application No. 60/294,203, filed on May 24, 2001, provisional application No. 60/317,479, filed on Sep. 5, 2001, provisional application No. 60/345,882, filed on Nov. 9, 2001, provisional application No. 60/345,145, filed on Nov. 9, 2001, provisional application No. 60/345,876, filed on Nov. 9, 2001, provisional application No. 60/332,280, filed on Nov. 21, 2001, provisional application No. 60/336,218, filed on Oct. 30, 2001, provisional application No. 60/335,049, filed on Oct. 30, 2001, provisional application No. 60/371,457, filed on Apr. 9, 2002, provisional application No. 60/332,279, filed on Nov. 21, 2001, provisional application No. 60/332,165, filed on Nov. 21, 2001, provisional application No. 60/342,066, filed on Dec. 18, 2002, provisional application No. 60/412,068, filed on Sep. 18, 2002.

(56) References Cited

U.S. PATENT DOCUMENTS

| | | |
|---|---|---|
| 3,164,600 A | 1/1965 | Janssen et al. |
| 3,169,095 A | 2/1965 | Thiel et al. |
| 3,200,819 A | 8/1965 | Gilbert |
| 3,219,533 A | 11/1965 | Mullins |
| 3,282,729 A | 11/1966 | Richardson et al. |
| 3,296,249 A | 1/1967 | Bell |
| 3,299,185 A | 1/1967 | Oda et al. |
| 3,371,085 A | 2/1968 | Reeder et al. |
| 3,393,197 A | 7/1968 | Pachter |

(56) References Cited

U.S. PATENT DOCUMENTS

| | | |
|---|---|---|
| 3,433,791 A | 3/1969 | Bentley et al. |
| 3,560,607 A | 2/1971 | Hartley et al. |
| 3,701,782 A | 10/1972 | Hester |
| 3,749,547 A | 7/1973 | Gregory et al. |
| 3,763,347 A | 10/1973 | Whitaker et al. |
| 3,831,606 A | 8/1974 | Damani |
| 3,847,650 A | 11/1974 | Gregory et al. |
| 3,864,326 A | 2/1975 | Babington |
| 3,894,040 A | 7/1975 | Buzby, Jr. |
| 3,909,463 A | 9/1975 | Hartman |
| 3,930,796 A | 1/1976 | Haensel |
| 3,943,941 A | 3/1976 | Boyd et al. |
| 3,949,743 A | 4/1976 | Shanbrom |
| 3,971,377 A | 7/1976 | Damani |
| 3,982,095 A | 9/1976 | Robinson |
| 3,987,052 A | 10/1976 | Hester, Jr. |
| 4,008,723 A | 2/1977 | Borthwick et al. |
| 4,020,379 A | 4/1977 | Manning |
| 4,045,156 A | 8/1977 | Chu et al. |
| 4,079,742 A | 3/1978 | Rainer et al. |
| 4,104,210 A | 8/1978 | Coran et al. |
| 4,121,583 A | 10/1978 | Chen |
| 4,141,369 A | 2/1979 | Burruss |
| 4,160,765 A | 7/1979 | Weinstock |
| 4,166,087 A | 8/1979 | Cline et al. |
| 4,183,912 A | 1/1980 | Rosenthale |
| 4,184,099 A | 1/1980 | Lindauer et al. |
| 4,190,654 A | 2/1980 | Gherardi et al. |
| 4,198,200 A | 4/1980 | Fonda et al. |
| RE30,285 E | 5/1980 | Babington |
| 4,219,031 A | 8/1980 | Rainer et al. |
| 4,229,447 A | 10/1980 | Porter |
| 4,229,931 A | 10/1980 | Schlueter et al. |
| 4,232,002 A | 11/1980 | Nogrady |
| 4,236,544 A | 12/1980 | Osaka |
| 4,251,525 A | 2/1981 | Weinstock |
| 4,276,243 A | 6/1981 | Partus |
| 4,280,629 A | 7/1981 | Slaughter |
| 4,284,089 A | 8/1981 | Ray |
| 4,286,604 A | 9/1981 | Ehretsmann et al. |
| 4,303,083 A | 12/1981 | Burruss, Jr. |
| 4,340,072 A | 7/1982 | Bolt et al. |
| 4,346,059 A | 8/1982 | Spector |
| 4,347,855 A | 9/1982 | Lanzillotti et al. |
| 4,376,767 A | 3/1983 | Sloan |
| 4,391,285 A | 7/1983 | Burnett et al. |
| 4,423,071 A | 12/1983 | Chignac et al. |
| 4,474,191 A | 10/1984 | Steiner |
| 4,484,576 A | 11/1984 | Albarda |
| 4,508,726 A | 4/1985 | Coleman |
| 4,523,589 A | 6/1985 | Krauser |
| 4,556,539 A | 12/1985 | Spector |
| 4,566,451 A | 1/1986 | Badewien |
| 4,588,425 A | 5/1986 | Usry et al. |
| 4,588,721 A | 5/1986 | Mahan |
| 4,591,615 A | 5/1986 | Aldred et al. |
| 4,605,552 A | 8/1986 | Fritschi |
| 4,627,963 A | 12/1986 | Olson |
| 4,647,428 A | 3/1987 | Gyulay |
| 4,647,433 A | 3/1987 | Spector |
| 4,654,370 A | 3/1987 | Marriott, III et al. |
| 4,683,231 A | 7/1987 | Glassman |
| 4,693,868 A | 9/1987 | Katsuda et al. |
| 4,708,151 A | 11/1987 | Shelar |
| 4,714,082 A | 12/1987 | Banerjee et al. |
| 4,722,334 A | 2/1988 | Blackmer et al. |
| 4,734,560 A | 3/1988 | Bowen |
| 4,735,217 A | 4/1988 | Gerth et al. |
| 4,735,358 A | 4/1988 | Morita et al. |
| 4,753,758 A | 6/1988 | Miller |
| 4,755,508 A | 7/1988 | Bock et al. |
| 4,756,318 A | 7/1988 | Clearman et al. |
| 4,765,347 A | 8/1988 | Sensabaugh, Jr. et al. |
| 4,771,795 A | 9/1988 | White et al. |
| 4,774,971 A | 10/1988 | Vieten |
| 4,793,365 A | 12/1988 | Sensabaugh, Jr. et al. |
| 4,793,366 A | 12/1988 | Hill |
| 4,800,903 A | 1/1989 | Ray et al. |
| 4,801,411 A | 1/1989 | Wellinghoff et al. |
| 4,814,161 A | 3/1989 | Jinks et al. |
| 4,819,665 A | 4/1989 | Roberts et al. |
| 4,848,374 A | 7/1989 | Chard et al. |
| 4,852,561 A | 8/1989 | Sperry |
| 4,853,517 A | 8/1989 | Bowen et al. |
| 4,854,331 A | 8/1989 | Banerjee et al. |
| 4,858,630 A | 8/1989 | Banerjee et al. |
| 4,863,720 A | 9/1989 | Burghart et al. |
| 4,881,541 A | 11/1989 | Eger et al. |
| 4,881,556 A | 11/1989 | Clearman et al. |
| 4,889,850 A | 12/1989 | Thornfeldt et al. |
| 4,895,719 A | 1/1990 | Radhakrishnan et al. |
| 4,906,417 A | 3/1990 | Gentry |
| 4,911,157 A | 3/1990 | Miller |
| 4,917,119 A | 4/1990 | Potter et al. |
| 4,917,120 A | 4/1990 | Hill |
| 4,917,830 A | 4/1990 | Ortiz et al. |
| 4,922,901 A | 5/1990 | Brooks et al. |
| 4,924,883 A | 5/1990 | Perfetti et al. |
| 4,928,714 A | 5/1990 | Shannon |
| 4,941,483 A | 7/1990 | Ridings et al. |
| 4,947,874 A | 8/1990 | Brooks et al. |
| 4,947,875 A | 8/1990 | Brooks et al. |
| 4,950,664 A | 8/1990 | Goldberg |
| 4,955,945 A | 9/1990 | Weick |
| 4,959,380 A | 9/1990 | Wilson |
| 4,963,289 A | 10/1990 | Ortiz et al. |
| 4,984,158 A | 1/1991 | Hillsman |
| 4,989,619 A | 2/1991 | Clearman et al. |
| 5,016,425 A | 5/1991 | Weick |
| 5,017,575 A | 5/1991 | Golwyn |
| 5,019,122 A | 5/1991 | Clearman et al. |
| 5,020,548 A | 6/1991 | Farrier et al. |
| 5,027,836 A | 7/1991 | Shannon et al. |
| 5,033,483 A | 7/1991 | Clearman et al. |
| 5,042,509 A | 8/1991 | Banerjee et al. |
| 5,049,389 A | 9/1991 | Radhakrishnan |
| 5,060,666 A | 10/1991 | Clearman et al. |
| 5,060,667 A | 10/1991 | Strubel |
| 5,060,671 A | 10/1991 | Counts et al. |
| 5,067,499 A | 11/1991 | Banerjee et al. |
| 5,072,726 A | 12/1991 | Mazloomdoost et al. |
| 5,076,292 A | 12/1991 | Sensabaugh, Jr. et al. |
| 5,099,861 A | 3/1992 | Clearman et al. |
| 5,105,831 A | 4/1992 | Banerjee et al. |
| 5,109,180 A | 4/1992 | Boultinghouse et al. |
| 5,112,598 A | 5/1992 | Biesalski |
| 5,118,494 A | 6/1992 | Schultz et al. |
| 5,119,834 A | 6/1992 | Shannon et al. |
| 5,126,123 A | 6/1992 | Johnson |
| 5,133,368 A | 7/1992 | Neumann et al. |
| 5,135,009 A | 8/1992 | Muller et al. |
| 5,137,034 A | 8/1992 | Perfetti et al. |
| 5,144,962 A | 9/1992 | Counts et al. |
| 5,146,915 A | 9/1992 | Montgomery |
| 5,156,170 A | 10/1992 | Clearman et al. |
| 5,160,664 A | 11/1992 | Liu |
| 5,164,740 A | 11/1992 | Ivri |
| 5,166,202 A | 11/1992 | Schweizer |
| 5,167,242 A | 12/1992 | Turner et al. |
| 5,177,071 A | 1/1993 | Freidinger et al. |
| 5,186,164 A | 2/1993 | Raghuprasad |
| 5,192,548 A | 3/1993 | Velasquez et al. |
| 5,224,498 A | 7/1993 | Deevi et al. |
| 5,229,120 A | 7/1993 | DeVincent |
| 5,229,382 A | 7/1993 | Chakrabarti et al. |
| 5,240,922 A | 8/1993 | O'Neill |
| 5,249,586 A | 10/1993 | Morgan et al. |
| 5,255,674 A | 10/1993 | Oftedal et al. |
| 5,261,424 A | 11/1993 | Sprin et al. |
| 5,264,433 A | 11/1993 | Sato et al. |
| 5,284,133 A | 2/1994 | Burns et al. |
| 5,292,499 A | 3/1994 | Evans et al. |
| 5,333,106 A | 7/1994 | Lanpher et al. |
| 5,345,951 A | 9/1994 | Serrano et al. |

(56) References Cited

U.S. PATENT DOCUMENTS

| | | |
|---|---|---|
| 5,363,842 A | 11/1994 | Mishelevich et al. |
| 5,364,838 A | 11/1994 | Rubsamen |
| 5,366,770 A | 11/1994 | Wang |
| 5,372,148 A | 12/1994 | McCafferty et al. |
| 5,376,386 A | 12/1994 | Ganderton et al. |
| 5,388,574 A | 2/1995 | Ingebrethsen |
| 5,391,081 A | 2/1995 | Lampotang et al. |
| 5,399,574 A | 3/1995 | Robertson et al. |
| 5,400,808 A | 3/1995 | Turner et al. |
| 5,431,167 A | 7/1995 | Savord |
| 5,436,230 A | 7/1995 | Soudant et al. |
| 5,451,408 A | 9/1995 | Mezei et al. |
| 5,455,043 A | 10/1995 | Fischel-Ghodsian |
| 5,456,247 A | 10/1995 | Shilling et al. |
| 5,456,677 A | 10/1995 | Spector |
| 5,457,100 A | 10/1995 | Daniel |
| 5,457,101 A | 10/1995 | Greenwood et al. |
| 5,459,137 A | 10/1995 | Andrasi et al. |
| 5,462,740 A | 10/1995 | Evenstad et al. |
| 5,468,936 A | 11/1995 | Deevi et al. |
| 5,501,236 A | 3/1996 | Hill et al. |
| 5,507,277 A | 4/1996 | Rubsamen et al. |
| 5,511,726 A | 4/1996 | Greenspan et al. |
| 5,519,019 A | 5/1996 | Andrasi et al. |
| 5,522,385 A | 6/1996 | Lloyd et al. |
| 5,525,329 A | 6/1996 | Snyder et al. |
| 5,540,959 A | 7/1996 | Wang |
| 5,543,434 A | 8/1996 | Weg |
| 5,544,646 A | 8/1996 | Lloyd et al. |
| 5,564,442 A | 10/1996 | MacDonald et al. |
| 5,584,701 A | 12/1996 | Lampotang et al. |
| 5,586,550 A | 12/1996 | Ivri et al. |
| 5,592,934 A | 1/1997 | Thwaites |
| 5,605,146 A | 2/1997 | Sarela |
| 5,605,897 A | 2/1997 | Beasley, Jr. et al. |
| 5,607,691 A | 3/1997 | Hale et al. |
| 5,619,984 A | 4/1997 | Hodson et al. |
| 5,622,944 A | 4/1997 | Hale et al. |
| 5,627,178 A | 5/1997 | Chakrabarti et al. |
| 5,641,938 A | 6/1997 | Holland et al. |
| 5,649,554 A | 7/1997 | Sprinkel |
| 5,655,523 A | 8/1997 | Hodson et al. |
| 5,656,255 A | 8/1997 | Jones |
| 5,660,166 A | 8/1997 | Lloyd et al. |
| 5,666,977 A | 9/1997 | Higgins et al. |
| 5,690,809 A | 11/1997 | Subramaniam et al. |
| 5,694,919 A | 12/1997 | Rubsamen et al. |
| 5,718,222 A | 2/1998 | Lloyd et al. |
| 5,724,957 A | 3/1998 | Rubsamen et al. |
| 5,725,756 A | 3/1998 | Subramaniam et al. |
| 5,733,572 A | 3/1998 | Unger et al. |
| 5,735,263 A | 4/1998 | Rubsamen et al. |
| 5,738,865 A | 4/1998 | Baichwal et al. |
| 5,743,250 A | 4/1998 | Gonda et al. |
| 5,743,251 A | 4/1998 | Howell et al. |
| 5,744,469 A | 4/1998 | Tran |
| 5,747,001 A | 5/1998 | Wiedmann et al. |
| 5,756,449 A | 5/1998 | Andersen et al. |
| 5,758,637 A | 6/1998 | Ivri et al. |
| 5,767,117 A | 6/1998 | Moskowitz et al. |
| 5,769,621 A | 6/1998 | Early et al. |
| 5,770,222 A | 6/1998 | Unger et al. |
| 5,771,882 A | 6/1998 | Psaros et al. |
| 5,776,928 A | 7/1998 | Beasley, Jr. |
| 5,804,212 A | 9/1998 | Illum |
| 5,809,997 A | 9/1998 | Wolf |
| 5,817,656 A | 10/1998 | Beasley, Jr. et al. |
| 5,819,756 A | 10/1998 | Mielordt |
| 5,823,178 A | 10/1998 | Lloyd et al. |
| 5,829,436 A | 11/1998 | Rubsamen et al. |
| 5,833,891 A | 11/1998 | Subramaniam et al. |
| 5,840,246 A | 11/1998 | Hammons et al. |
| 5,855,564 A | 1/1999 | Ruskewicz |
| 5,855,913 A | 1/1999 | Hanes et al. |
| 5,874,064 A | 2/1999 | Edwards et al. |
| 5,874,481 A | 2/1999 | Weers et al. |
| 5,875,776 A | 3/1999 | Vaghefi |
| 5,878,752 A | 3/1999 | Adams et al. |
| 5,884,620 A | 3/1999 | Gonda et al. |
| 5,890,908 A | 4/1999 | Lampotang et al. |
| 5,894,841 A | 4/1999 | Voges |
| 5,900,249 A | 5/1999 | Smith |
| 5,906,811 A | 5/1999 | Hersh |
| 5,907,075 A | 5/1999 | Subramaniam et al. |
| 5,910,301 A | 6/1999 | Farr et al. |
| 5,915,378 A | 6/1999 | Lloyd et al. |
| 5,918,595 A | 7/1999 | Olsson |
| 5,928,520 A | 7/1999 | Haumesser |
| 5,929,093 A | 7/1999 | Pang et al. |
| 5,934,272 A | 8/1999 | Lloyd et al. |
| 5,934,289 A | 8/1999 | Watkins et al. |
| 5,935,604 A | 8/1999 | Illum |
| 5,938,117 A | 8/1999 | Ivri |
| 5,939,100 A | 8/1999 | Albrechtsen et al. |
| 5,941,240 A | 8/1999 | Gonda et al. |
| 5,944,012 A | 8/1999 | Pera |
| 5,957,124 A | 9/1999 | Lloyd et al. |
| 5,960,792 A | 10/1999 | Lloyd et al. |
| 5,970,973 A | 10/1999 | Gonda et al. |
| 5,971,951 A | 10/1999 | Ruskewicz |
| 5,985,309 A | 11/1999 | Edwards et al. |
| 5,993,805 A | 11/1999 | Sutton et al. |
| 6,004,970 A | 12/1999 | O'Malley et al. |
| 6,008,214 A | 12/1999 | Kwon et al. |
| 6,008,216 A | 12/1999 | Chakrabarti et al. |
| 6,013,050 A | 1/2000 | Bellhouse et al. |
| 6,014,969 A | 1/2000 | Lloyd et al. |
| 6,014,970 A | 1/2000 | Ivri et al. |
| 6,041,777 A | 3/2000 | Faithfull et al. |
| 6,044,777 A | 4/2000 | Walsh |
| 6,048,550 A | 4/2000 | Chan et al. |
| 6,048,857 A | 4/2000 | Ellinwood, Jr. et al. |
| 6,050,260 A | 4/2000 | Daniell et al. |
| 6,051,257 A | 4/2000 | Kodas et al. |
| 6,051,566 A | 4/2000 | Bianco |
| RE36,744 E | 6/2000 | Goldberg |
| 6,089,857 A | 7/2000 | Matsuura et al. |
| 6,090,212 A | 7/2000 | Mahawili |
| 6,090,403 A | 7/2000 | Block et al. |
| 6,095,134 A | 8/2000 | Sievers et al. |
| 6,095,153 A | 8/2000 | Kessler et al. |
| 6,098,620 A | 8/2000 | Lloyd et al. |
| 6,102,036 A | 8/2000 | Slutsky et al. |
| 6,113,795 A | 9/2000 | Subramaniam et al. |
| 6,117,866 A | 9/2000 | Bondinell et al. |
| 6,125,853 A | 10/2000 | Susa et al. |
| 6,126,919 A | 10/2000 | Stefely et al. |
| 6,131,566 A | 10/2000 | Ashurst et al. |
| 6,131,570 A | 10/2000 | Schuster et al. |
| 6,133,327 A | 10/2000 | Kimura et al. |
| 6,135,369 A | 10/2000 | Prendergast et al. |
| 6,136,295 A | 10/2000 | Edwards et al. |
| 6,138,683 A | 10/2000 | Hersh et al. |
| 6,140,323 A | 10/2000 | Ellinwood, Jr. et al. |
| 6,143,277 A | 11/2000 | Ashurst et al. |
| 6,143,746 A | 11/2000 | Daugan et al. |
| 6,149,892 A | 11/2000 | Britto |
| 6,155,268 A | 12/2000 | Takeuchi |
| 6,158,431 A | 12/2000 | Poole |
| 6,167,880 B1 | 1/2001 | Gonda et al. |
| 6,211,171 B1 | 4/2001 | Sawynok et al. |
| 6,234,167 B1 | 5/2001 | Cox et al. |
| 6,241,969 B1 | 6/2001 | Saidi et al. |
| 6,250,298 B1 | 6/2001 | Gonda et al. |
| 6,255,334 B1 | 7/2001 | Sands |
| 6,263,872 B1 | 7/2001 | Schuster et al. |
| 6,264,922 B1 | 7/2001 | Wood et al. |
| 6,284,287 B1 | 9/2001 | Sarlikiotis et al. |
| 6,290,986 B1 | 9/2001 | Murdock et al. |
| 6,299,900 B1 | 10/2001 | Reed et al. |
| 6,300,710 B1 | 10/2001 | Nakamori |
| 6,306,431 B1 | 10/2001 | Zhang et al. |
| 6,313,176 B1 | 11/2001 | Ellinwood, Jr. et al. |
| 6,376,550 B1 | 4/2002 | Raber et al. |

(56) References Cited

U.S. PATENT DOCUMENTS

| | | |
|---|---|---|
| 6,408,854 B1 | 6/2002 | Gonda et al. |
| 6,413,930 B1 | 7/2002 | Ratti et al. |
| 6,420,351 B1 | 7/2002 | Tsai et al. |
| 6,431,166 B2 | 8/2002 | Gonda et al. |
| 6,443,152 B1 | 9/2002 | Lockhart et al. |
| 6,444,665 B1 | 9/2002 | Helton et al. |
| 6,461,591 B1 | 10/2002 | Keller et al. |
| 6,479,074 B2 | 11/2002 | Murdock et al. |
| 6,506,762 B1 | 1/2003 | Horvath et al. |
| 6,514,482 B1 | 2/2003 | Bartus et al. |
| 6,516,796 B1 | 2/2003 | Cox et al. |
| 6,591,839 B2 | 7/2003 | Meyer et al. |
| 6,632,047 B2 | 10/2003 | Vinegar et al. |
| 6,638,981 B2 | 10/2003 | Williams et al. |
| 6,682,716 B2 | 1/2004 | Hodges et al. |
| 6,701,922 B2 | 3/2004 | Hindle et al. |
| 6,716,415 B2 | 4/2004 | Rabinowitz et al. |
| 6,716,416 B2 | 4/2004 | Rabinowitz et al. |
| 6,716,417 B2 | 4/2004 | Rabinowitz et al. |
| 6,737,042 B2 | 5/2004 | Rabinowitz et al. |
| 6,737,043 B2 | 5/2004 | Rabinowitz et al. |
| 6,740,307 B2 | 5/2004 | Rabinowitz et al. |
| 6,740,308 B2 | 5/2004 | Rabinowitz et al. |
| 6,740,309 B2 | 5/2004 | Rabinowitz et al. |
| 6,743,415 B2 | 6/2004 | Rabinowitz et al. |
| 6,759,029 B2 | 7/2004 | Hale et al. |
| 6,772,756 B2 | 8/2004 | Shayan |
| 6,772,757 B2 | 8/2004 | Sprinkel, Jr. et al. |
| 6,776,978 B2 | 8/2004 | Rabinowitz et al. |
| 6,779,520 B2 | 8/2004 | Genova et al. |
| 6,780,399 B2 | 8/2004 | Rabinowitz et al. |
| 6,780,400 B2 | 8/2004 | Rabinowitz et al. |
| 6,783,753 B2 | 8/2004 | Rabinowitz et al. |
| 6,797,259 B2 | 9/2004 | Rabinowitz et al. |
| 6,803,031 B2 | 10/2004 | Rabinowitz et al. |
| 6,805,853 B2 | 10/2004 | Rabinowitz et al. |
| 6,805,854 B2 | 10/2004 | Hale et al. |
| 6,814,954 B2 | 11/2004 | Rabinowitz et al. |
| 6,814,955 B2 | 11/2004 | Rabinowitz et al. |
| 6,855,310 B2 | 2/2005 | Rabinowitz et al. |
| 6,884,408 B2 | 4/2005 | Rabinowitz et al. |
| 6,994,843 B2 | 2/2006 | Rabinowitz et al. |
| 7,005,121 B2 | 2/2006 | Rabinowitz et al. |
| 7,005,122 B2 | 2/2006 | Hale et al. |
| 7,008,615 B2 | 3/2006 | Rabinowitz et al. |
| 7,008,616 B2 | 3/2006 | Rabinowitz et al. |
| 7,011,819 B2 | 3/2006 | Hale et al. |
| 7,011,820 B2 | 3/2006 | Rabinowitz et al. |
| 7,014,840 B2 | 3/2006 | Hale et al. |
| 7,014,841 B2 | 3/2006 | Rabinowitz et al. |
| 7,018,619 B2 | 3/2006 | Rabinowitz et al. |
| 7,018,620 B2 | 3/2006 | Rabinowitz et al. |
| 7,018,621 B2 | 3/2006 | Hale et al. |
| 7,022,312 B2 | 4/2006 | Rabinowitz et al. |
| 7,029,658 B2 | 4/2006 | Rabinowitz et al. |
| 7,033,575 B2 | 4/2006 | Rabinowitz et al. |
| 7,040,314 B2 | 5/2006 | Nguyen et al. |
| 7,045,118 B2 | 5/2006 | Rabinowitz et al. |
| 7,045,119 B2 | 5/2006 | Rabinowitz et al. |
| 7,048,909 B2 | 5/2006 | Rabinowitz et al. |
| 7,052,679 B2 | 5/2006 | Rabinowitz et al. |
| 7,052,680 B2 | 5/2006 | Rabinowitz et al. |
| 7,060,254 B2 | 6/2006 | Rabinowitz et al. |
| 7,060,255 B2 | 6/2006 | Rabinowitz et al. |
| 7,063,830 B2 | 6/2006 | Rabinowitz et al. |
| 7,063,831 B2 | 6/2006 | Rabinowitz et al. |
| 7,063,832 B2 | 6/2006 | Rabinowitz et al. |
| 7,067,114 B2 | 6/2006 | Rabinowitz et al. |
| 7,070,761 B2 | 7/2006 | Rabinowitz et al. |
| 7,070,762 B2 | 7/2006 | Rabinowitz et al. |
| 7,070,763 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,070,766 B2 | 7/2006 | Rabinowitz et al. |
| 7,078,016 B2 | 7/2006 | Rabinowitz et al. |
| 7,078,017 B2 | 7/2006 | Rabinowitz et al. |
| 7,078,018 B2 | 7/2006 | Rabinowitz et al. |
| 7,078,019 B2 | 7/2006 | Rabinowitz et al. |
| 7,078,020 B2 | 7/2006 | Rabinowitz et al. |
| 7,087,216 B2 | 8/2006 | Rabinowitz et al. |
| 7,087,217 B2 | 8/2006 | Rabinowitz et al. |
| 7,087,218 B2 | 8/2006 | Rabinowitz et al. |
| 7,090,830 B2 | 8/2006 | Hale et al. |
| 7,094,392 B2 | 8/2006 | Rabinowitz et al. |
| 7,108,847 B2 | 9/2006 | Rabinowitz et al. |
| 7,115,250 B2 | 10/2006 | Rabinowitz et al. |
| 7,169,378 B2 | 1/2007 | Rabinowitz et al. |
| 7,402,777 B2 | 7/2008 | Ron et al. |
| 7,442,368 B2 | 10/2008 | Rabinowitz et al. |
| 7,445,768 B2 | 11/2008 | Rabinowitz et al. |
| 7,449,172 B2 | 11/2008 | Rabinowitz et al. |
| 7,449,173 B2 | 11/2008 | Rabinowitz et al. |
| 7,449,174 B2 | 11/2008 | Rabinowitz et al. |
| 7,449,175 B2 | 11/2008 | Rabinowitz et al. |
| 7,458,374 B2 | 12/2008 | Hale et al. |
| 7,465,435 B2 | 12/2008 | Rabinowitz et al. |
| 7,465,436 B2 | 12/2008 | Rabinowitz et al. |
| 7,465,437 B2 | 12/2008 | Rabinowitz et al. |
| 7,468,179 B2 | 12/2008 | Rabinowitz et al. |
| 7,470,421 B2 | 12/2008 | Rabinowitz et al. |
| 7,485,285 B2 | 2/2009 | Rabinowitz et al. |
| 7,488,469 B2 | 2/2009 | Rabinowitz et al. |
| 7,491,047 B2 | 2/2009 | Rabinowitz et al. |
| 7,498,019 B2 | 3/2009 | Hale et al. |
| 7,507,397 B2 | 3/2009 | Rabinowitz et al. |
| 7,507,398 B2 | 3/2009 | Rabinowitz et al. |
| 7,510,702 B2 | 3/2009 | Rabinowitz et al. |
| 7,513,781 B2 | 4/2009 | Galauner et al. |
| 7,524,484 B2 | 4/2009 | Rabinowitz et al. |
| 7,537,009 B2 | 5/2009 | Hale et al. |
| 7,540,286 B2 | 6/2009 | Cross et al. |
| 7,550,133 B2 | 6/2009 | Hale et al. |
| 7,581,540 B2 | 9/2009 | Hale et al. |
| 7,585,493 B2 | 9/2009 | Hale et al. |
| 7,601,337 B2 | 10/2009 | Rabinowitz et al. |
| 7,645,442 B2 | 1/2010 | Hale et al. |
| 7,766,013 B2 | 8/2010 | Wensley et al. |
| 7,834,295 B2 | 11/2010 | Sharma et al. |
| 7,913,688 B2 | 3/2011 | Cross et al. |
| 7,923,662 B2 | 4/2011 | Hale et al. |
| 7,942,147 B2 | 5/2011 | Hodges et al. |
| 7,981,401 B2 | 7/2011 | Every et al. |
| 7,987,846 B2 | 8/2011 | Hale et al. |
| 7,988,952 B2 | 8/2011 | Rabinowitz et al. |
| 8,003,080 B2 | 8/2011 | Rabinowitz et al. |
| 8,074,644 B2 | 12/2011 | Hale et al. |
| 8,173,107 B2 | 5/2012 | Rabinowitz et al. |
| 8,235,037 B2 | 8/2012 | Hale et al. |
| 8,288,372 B2 | 10/2012 | Hale et al. |
| 2001/0020147 A1 | 9/2001 | Staniforth et al. |
| 2001/0039262 A1 | 11/2001 | Venkataraman |
| 2002/0031480 A1 | 3/2002 | Peart et al. |
| 2002/0037828 A1 | 3/2002 | Wilson et al. |
| 2002/0058009 A1 | 5/2002 | Bartus et al. |
| 2002/0061281 A1 | 5/2002 | Osbakken et al. |
| 2002/0086852 A1 | 7/2002 | Cantor |
| 2002/0112723 A1 | 8/2002 | Schuster et al. |
| 2002/0117175 A1 | 8/2002 | Kottayil et al. |
| 2002/0176841 A1 | 11/2002 | Barker et al. |
| 2003/0004142 A1 | 1/2003 | Prior et al. |
| 2003/0032638 A1 | 2/2003 | Kim et al. |
| 2003/0051728 A1 | 3/2003 | Lloyd et al. |
| 2003/0118512 A1 | 6/2003 | Shen |
| 2003/0131843 A1 | 7/2003 | Lu |
| 2003/0138508 A1 | 7/2003 | Novack et al. |
| 2004/0016427 A1 | 1/2004 | Byron et al. |
| 2004/0096402 A1 | 5/2004 | Hodges et al. |
| 2004/0101481 A1 | 5/2004 | Hale et al. |
| 2004/0105818 A1 | 6/2004 | Every et al. |
| 2004/0234699 A1 | 11/2004 | Hale et al. |
| 2004/0234914 A1 | 11/2004 | Hale et al. |
| 2004/0234916 A1 | 11/2004 | Hale et al. |
| 2005/0034723 A1 | 2/2005 | Bennett et al. |
| 2005/0037506 A1 | 2/2005 | Hale et al. |

(56) References Cited

U.S. PATENT DOCUMENTS

| | | |
|---|---|---|
| 2005/0079166 A1 | 4/2005 | Damani et al. |
| 2005/0126562 A1 | 6/2005 | Rabinowitz et al. |
| 2005/0131739 A1 | 6/2005 | Rabinowitz et al. |
| 2006/0032496 A1 | 2/2006 | Hale et al. |
| 2006/0120962 A1 | 6/2006 | Rabinowitz et al. |
| 2006/0193788 A1 | 8/2006 | Hale et al. |
| 2006/0257329 A1 | 11/2006 | Rabinowitz et al. |
| 2007/0122353 A1 | 5/2007 | Hale et al. |
| 2007/0286816 A1 | 12/2007 | Hale et al. |
| 2008/0038363 A1 | 2/2008 | Zaffaroni et al. |
| 2008/0216828 A1 | 9/2008 | Wensley |
| 2008/0299048 A1 | 12/2008 | Hale et al. |
| 2008/0306285 A1 | 12/2008 | Hale et al. |
| 2009/0062254 A1 | 3/2009 | Hale et al. |
| 2009/0180968 A1 | 7/2009 | Hale et al. |
| 2009/0235926 A1 | 9/2009 | Cross |
| 2009/0258075 A1 | 10/2009 | Hale et al. |
| 2009/0301363 A1 | 12/2009 | Damani et al. |
| 2010/0006092 A1 | 1/2010 | Hale et al. |
| 2010/0055048 A1 | 3/2010 | Hale et al. |
| 2010/0065052 A1 | 3/2010 | Sharma et al. |
| 2010/0068155 A1 | 3/2010 | Lei et al. |
| 2010/0181387 A1 | 7/2010 | Zaffaroni et al. |
| 2010/0294268 A1 | 11/2010 | Wensley et al. |
| 2010/0300433 A1 | 12/2010 | Sharma et al. |
| 2011/0233043 A1 | 9/2011 | Cross et al. |
| 2011/0240013 A1 | 10/2011 | Hale et al. |
| 2011/0240014 A1 | 10/2011 | Bennett et al. |
| 2011/0240022 A1 | 10/2011 | Hodges et al. |
| 2011/0244020 A1 | 10/2011 | Hale et al. |
| 2011/0245493 A1 | 10/2011 | Rabinowitz et al. |
| 2011/0253135 A1 | 10/2011 | Hale et al. |
| 2012/0048963 A1 | 3/2012 | Sharma et al. |

FOREIGN PATENT DOCUMENTS

| | | |
|---|---|---|
| CN | 1176075 | 3/1998 |
| DE | 198 54 007 | 5/2000 |
| EP | 0 039 369 | 11/1981 |
| EP | 0 274 431 | 7/1988 |
| EP | 0 277 519 | 8/1988 |
| EP | 0 358 114 | 3/1990 |
| EP | 0 430 559 | 6/1991 |
| EP | 0 492 485 | 7/1992 |
| EP | 0 606 486 | 7/1994 |
| EP | 0 734 719 | 2/1996 |
| EP | 0 967 214 | 12/1999 |
| EP | 1 080 720 | 3/2001 |
| EP | 1 177 793 | 2/2002 |
| EP | 0 808 635 B1 | 7/2003 |
| FR | 921 852 A | 5/1947 |
| FR | 2 428 068 A | 1/1980 |
| GB | 502 761 | 1/1938 |
| GB | 903 866 | 8/1962 |
| GB | 1 366 041 | 9/1974 |
| GB | 2 108 390 | 5/1983 |
| GB | 2 122 903 | 1/1984 |
| HU | 200105 B | 10/1988 |
| HU | 2193292 | 6/1993 |
| WO | WO 85/00520 | 2/1985 |
| WO | WO 88/08304 | 11/1988 |
| WO | WO 90/02737 | 3/1990 |
| WO | WO 90/07333 | 7/1990 |
| WO | WO 91/07947 | 6/1991 |
| WO | WO 91/18525 | 12/1991 |
| WO | WO 92/05781 | 4/1992 |
| WO | WO 92/15353 | 9/1992 |
| WO | WO 92/19303 | 11/1992 |
| WO | WO 93/12823 | 7/1993 |
| WO | WO 94/09842 | 5/1994 |
| WO | WO 94/16717 | 8/1994 |
| WO | WO 94/16757 | 8/1994 |
| WO | WO 94/16759 | 8/1994 |
| WO | WO 94/17369 | 8/1994 |
| WO | WO 94/17370 | 8/1994 |
| WO | WO 94/27576 | 12/1994 |
| WO | WO 94/27653 | 12/1994 |
| WO | WO 95/31182 | 11/1995 |
| WO | WO 96/00069 | 1/1996 |
| WO | WO 96/00070 | 1/1996 |
| WO | WO 96/00071 | 1/1996 |
| WO | WO 96/09846 | 4/1996 |
| WO | WO 96/10663 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 96/31198 | 10/1996 |
| WO | WO 96/37198 | 11/1996 |
| WO | WO 97/16181 | 5/1997 |
| WO | WO 97/17948 | 5/1997 |
| WO | WO 97/23221 | 7/1997 |
| WO | WO 97/27804 | 8/1997 |
| WO | WO 97/31691 | 9/1997 |
| WO | WO 97/35562 | 10/1997 |
| WO | WO 97/35582 | 10/1997 |
| WO | WO 97/36574 | 10/1997 |
| WO | WO 97/40819 | 11/1997 |
| WO | WO 97/49690 | 12/1997 |
| WO | WO 98/02186 | 1/1998 |
| WO | WO 98/16205 | 4/1998 |
| WO | WO 98/22170 | 5/1998 |
| WO | WO 98/29110 | 7/1998 |
| WO | WO 98/31346 | 7/1998 |
| WO | WO 98/34595 | 8/1998 |
| WO | WO 98/36651 | 8/1998 |
| WO | WO 98/37896 | 9/1998 |
| WO | WO 99/04797 | 2/1999 |
| WO | WO 99/16419 | 4/1999 |
| WO | WO 99/24433 | 5/1999 |
| WO | WO 99/37347 | 7/1999 |
| WO | WO 99/37625 | 7/1999 |
| WO | WO 99/44664 | 9/1999 |
| WO | WO 99/55362 | 11/1999 |
| WO | WO 99/59710 | 11/1999 |
| WO | WO 99/64094 | 12/1999 |
| WO | WO 00/00176 | 1/2000 |
| WO | WO 00/00215 | 1/2000 |
| WO | WO 00/00244 | 1/2000 |
| WO | WO 00/19991 | 4/2000 |
| WO | WO 00/27359 | 5/2000 |
| WO | WO 00/27363 | 5/2000 |
| WO | WO 00/28979 | 5/2000 |
| WO | WO 00/29053 | 5/2000 |
| WO | WO 00/29167 | 5/2000 |
| WO | WO 00/35417 | 6/2000 |
| WO | WO 00/38618 | 7/2000 |
| WO | WO 00/44350 | 8/2000 |
| WO | WO 00/44730 | 8/2000 |
| WO | WO 00/47203 | 9/2000 |
| WO | WO 00/51491 | 9/2000 |
| WO | WO 00/64940 | 11/2000 |
| WO | WO 00/66084 | 11/2000 |
| WO | WO 00/66106 | 11/2000 |
| WO | WO 00/66206 | 11/2000 |
| WO | WO 00/72827 | 12/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/19528 | 3/2001 |
| WO | WO 01/29011 | 4/2001 |
| WO | WO 01/32144 | 5/2001 |
| WO | WO 01/41732 | 6/2001 |
| WO | WO 01/69136 | 9/2001 |
| WO | WO 01/80829 | 11/2001 |
| WO | WO 01/95903 | 12/2001 |
| WO | WO 02/00198 | 1/2002 |
| WO | WO 02/24158 | 3/2002 |
| WO | WO 02/056866 | 7/2002 |
| WO | WO 02/083119 | 10/2002 |
| WO | WO 02/098389 | 12/2002 |

(56) References Cited

FOREIGN PATENT DOCUMENTS

| WO | WO 02/102297 | 12/2002 |
|---|---|---|
| WO | WO 03/024456 | 3/2003 |
| WO | WO 03/037412 | 5/2003 |

OTHER PUBLICATIONS

Office Action mailed Jun. 3, 2004 with respect to U.S. Appl. No. 10/057,197.
Office Action mailed Jun. 5, 2007 with respect to U.S. Appl. No. 10/057,197.
Office Action mailed Sep. 21, 2006 with respect to U.S. Appl. No. 10/057,197.
Office Action mailed Dec. 15, 2003 with respect to U.S. Appl. No. 10/057,197.
Office Action mailed Feb. 27, 2004 with respect to U.S. Appl. No. 10/146,080.
Office Action mailed Mar. 20, 2007 with respect to U.S. Appl. No. 10/146,080.
Office Action mailed Jun. 5, 2006 with respect to U.S. Appl. No. 10/146,080.
Office Action mailed Aug. 25, 2005 with respect to U.S. Appl. No. 10/146,080.
Office Action mailed Dec. 28, 2007 with respect to U.S. Appl. No. 10/146,080.
Office Action mailed Feb. 12, 2007 with respect to U.S. Appl. No. 10/146,086.
Office Action mailed Oct. 30, 2007 with respect to U.S. Appl. No. 10/146,086.
Office Action mailed Dec. 13, 2005 with respect to U.S. Appl. No. 10/146,086.
Office Action mailed Feb. 16, 2007 with respect to U.S. Appl. No. 10/146,088.
Office Action mailed Sep. 28, 2007 with respect to U.S. Appl. No. 10/146,088.
Office Action mailed Nov. 21, 2007 with respect to U.S. Appl. No. 10/146,088.
Office Action mailed Aug. 13, 2003 with respect to U.S. Appl. No. 10/153,313.
Office Action mailed Mar. 08, 2005 with respect to U.S. Appl. No. 10/718,982.
Anderson, M.E. (1982). "Recent Advances in Methodology and Concepts for Characterizing Inhalation Pharmacokinetic Parameters in Animals and Man," Drug Metabolism Reviews. 13(5):799-826.
Anonymous, (Jun. 1998) Guidance for Industry: Stability testing of drug substances and products, U.S. Department of Health and Human Services, FDA, CDER, CBER , pp. 1-110.
Bennett, R. L. et al. (1981). "Patient-Controlled Analgesia: A New Concept of Postoperative Pain Relief," Annual Surg. 195(6):700-705.
Benowitz (1994). "Individual Differences in Nicotine Kinetics and Metabolism in Humans," NIDA Research Monography, 2 pages.
BP: Chemicals Products-Barrier Resins (1999). located at <http://www.bp.com/chemicals/products/product.asp> (visited on Aug. 2, 2001), 8 pages.
Brand, P. et al. (Jun. 2000). "Total Deposition of Therapeutic Particles During Spontaneous and Controlled Inhalations," Journal of Pharmaceutical Sciences. 89(6):724-731.
Campbell, Fiona A. et al. (2001) "Are cannabinoids an effective and safe treatment option in the management of pain? A qualitative systemic review," BMJ, 323 pp. 1-6.
Carroll, M.E. et al. (1990), "Cocaine-Base Smoking in Rhesus Monkey: Reinforcing and Physiological Effects," Psychopharmacology (Berl) 102:443-450.
Cichewicz, Diana L. et al. (May 1999) "Enhancement of mu opioid antinociception by oral DELTA 9—tetrahydrocannabinol: Dose response analysis and receptor identification" Journal of Pharmacology and Experimental Therapeutics vol. 289 (2): 859-867.
Clark, A. and Byron, P. (1986). "Dependence of Pulmonary Absorption Kinetics on Aerosol Particle Size," Z. Erkrank. 166:13-24.
Dallas, C. et al. (1983). "A Small Animal Model for Direct Respiratory and Hemodynamic Measurements in Toxicokinetic Studies of Volatile Chemicals," Devlopments in the Science and Practice of Toxicology. Hayes, A. W. et al. eds., Elsevier Science Publishers, New York. pp. 419-422.
Darquenne, C. et al. (1997). "Aerosol Dispersion in Human Lung: Comparison Between Numerical Simulations and Experiments for Bolus Tests," American Physiological Society. 966-974.
Database Biosis "Online!" Biosciences Information Service, Philadelphia, PA 1979, Knight, V. et al., "Amantadine aerosol in humans", database accession No. PREV 198069035552 abstract, & Antimicrobial Agents and Chemotherapy 16(5):572-578.
Database Biosis "Online!" Biosciences Information Service, Philadelphia, PA 1979, Wilson. S.Z. et al., "Amatadine Aerosol Particle A.erosol Generation and Delivery to Man" Database accession No. PREV198069008137, abstract & Proceedings of the Society for Experimental Biology and Medicine 161(3):350-354.
Database WPI, Section CH, Week 198941, Derwent Publications Ltd., London, GB; Class B07, AN 1989-297792 AP002230849 & JP 01 221313 (Nippon Create 1(K), Sep. 4, 1989, abstract.
Davies, C. N. et al. (May 1972). "Breathing of Half-Micron Aerosols," Journal of Applied Physiology. 32(5):591-600.
Dershwitz, M., M.D., et al. (Sep. 2000). "Pharmacokinetics and Pharmacodynamics of Inhaled versus Intravenous Morphine in Healthy Volunteers," Anesthesiology. 93(3): 619-628.
Drugs Approved by the FDA—Drug Name: Nicotrol Inhaler (2000) located at <http://www.centerwatch.com/patient/drugs/dru202.html> (Visited on Aug. 2, 2001), 2 pages.
Faris et al. (2002) "Current evidence supporting the role of diuretics in heart failure: a meta analysis of randomized controlled trials." International Journal of Cardiology vol. 82:149-158.
Feynman, R.P. et al. (1964). "Chapter 32: Refractive Index of Dense Materials" The Feyman Lectures on Physics: Mainly Electromagnetism and Matter. Addison-Wesley: Publishing Company, Inc., Reading, Massachusetts: pp. 32-1-32-13.
Finlay, W. H. (2001). "The Mechanics of Inhaled Pharmaceutical Aerosols", Academic Press: San Diego Formula 2.39. pp. 3-14 (Table of Contents). pp. v-viii.
Gleeson, et al. (1982) "Chlorpromazine Hyperalgesia Antagonizes Clonidine Analgesia, but Enhances Morphine Analgesia in Rats Tested in a Hot-Water Tail-Flick Paradigm" Psychopharmacology vol. 78: 141-146.
Gonda, I. (1991). "Particle Deposition in the Human Respiratory Tract,"Chapter 176, The Lung: Scientific Foundations. Crystal R.G. and West, J.B. (eds.), Raven Publishers, New York. pp. 2289-2294.
Graves, D. A. et al. (1983). "Patient-Controlled Analgesia," Annals of Internal Medicine. 99:360-366.
Hamon, et al. (1987) "Opioid Receptors and Neuropeptides in the CNS in Rats Treated Chronically with Amoxapine and Amitriptyline" Neuropharmacology vol. 26 No. 6: 531-539.
Hatsukami D., et al. (May 1990) "A Method for Delivery of Precise Doses of Smoked Cocaine-Base to Human " Pharmacology Biochemistry & Behavior. 36(1):1-7.
Heyder, J. et al. (1986). "Deposition of Particles in the Human Respiratory Tract in the Size Range 0.005-15 μm," J. Aerosol Sci. 17(5):811-822.
Hong et al. (2002) Respiratory Drug Delivery VIII:779-781.
Huizer, H. (1987). "Analytical Studies on Illicit Heron. V. Efficacy of Volitization During Heroin Smoking." Pharmaceutisch Weekblad Scientific Edition. 9(4):203-211.
Hurt, R. D., MD and Robertson, C. R., PhD, (Oct. 1998). "Prying Open the Door to the Tobacco Industry's Secrets About Nicotine: The Minnesota Tobacco Trial," JAMA 280(13):1173-1181.
Hwang, S. L. (Jun. 1999). "Artificial Nicotine Studied: R. J. Reynolds Seeks to Develop Drugs that Mimic Tobacco's Potent Effects on Brain," Wall Street Journal, 3 pages.
James, A.C. et al., (1991). "The Respiratory Tract Deposition Model Proposed by the ICRP Task Group," Radiation Protection Dosimetry, 38(1/3):159-165.
Kim, M. H. and Patel, D.V. (1994). "'BOP' As a Reagent for Mild and Efficient Preparation of Esters," Tet. Letters 35:5603-5606.

(56) References Cited

OTHER PUBLICATIONS

Lichtman, A. H. et al. (1996). "Inhalation Exposure to Volatilized Opioids Produces Antinociception in Mice," Journal of Pharmacology and Experimental Therapeutics. 279(1):69-76 XP-001118649.

Lichtman, A. H. et al. (2000). "Pharmacological Evaluation of Aerosolized Cannabinoids in Mice" European Journal of Pharmacology, vol. 399, No. 2-3: 141-149.

Lopez, K. (Jul. 1999). "UK Researcher Develops Nicotinic Drugs with R. J. Reynolds," located at <http://www.eurekalert.org/pub_releases/1999-07/UoKM-Urdn-260799.php> (visited on Oct. 1, 2002), 1 page.

Lynch, Mary E. (2001) "Antidepressants as analgesics: a review of randomized controlled trials" J. Psychiatry Neuroscience vol. 26: 30-36.

Magnusson et al. (2000) "The Involvement of Dopamine in Nociception: the role of D1 and D2 Receptors in the Dorsolateral Striatum." Brain Research vol. 855: 260-266.

Martin, B. R. and Lue, L. P. (May/Jun. 1989). "Pyrolysis and Volatilization of Cocaine," Journal of Analytical Toxicology 13:158-162.

Mattox, A.J. and Carroll, M.E. (1996). "Smoked Heroin Self-Administration in Rhesus Monkeys," Psychopharmacology 125:195-201.

McCormick, A.S.M., et al., "Bronchospasm During Inhalation of Nebulized Midazolam," British Journal of Anesthesia, vol. 80 (4), Apr. 1988, pp. 564-565 XP001119488.

McGee et al. (1979) "Phenotiazine Analgesia—Fact or Fantasy?" American Journal of Hospital Pharmacy vol. 36: 633-640.

Meng, Y. et al. (1997). "Inhalation Studies with Drugs of Abuse", NIDA Research Monogragh 173:201-224.

Meng, Y., et al. (1999). "Pharmacological effects of methamphetamine and other stimulants via inhalation exposure," Drug and Alcohol Dependence. 53:111-120.

Pankow, J. (Mar. 2000). ACS Conference—San Francisco—Mar. 26, 2000. Chemistry of Tobacco Smoke. pp. 1-8.

Pankow, J. F. et al. (1997). "Conversion of Nicotine in Tobacco Smoke to Its Volatile and Available Free-Base Form through the Action of Gaseous Ammonia," Environ. Sci. Technol. 31:2428-2433.

Pfeiffer, Ronald (1982) "Drugs for pain in the elderly" Geriatrics vol. 37 No. 2: 67-76.

Poochikian, G. and Bertha, C.M. (2000). "Inhalation Drug Product Excipient Controls: Significance and Pitfalls," Resp. Drug Deliv. VII: 109-115.

Rapoport et al. (1997) CNS Drugs 7(1):37-46.

Schreiber et al. (1999) "The Atypical Neuroleptics Clozapine and Olanzapine Differ Regarding Their Antinociceptive Mechanisms and Potency" Pharmacology Biochemistry and Behavior vol. 64 No. 1: 75-80.

ScienceDaily Magazine, (Jul. 1999). "University of Kentucky Researcher Develops Nicotinic Drugs with R. J. Reynolds," located at <http://www.sciencedaily.com/releases/1999/07/990728073542.htm.> (visited on Sep. 23, 2002), 2 pages.

Seeman, J. et al. (1999). "The Form of Nicotine in Tobacco. Thermal Transfer of Nicotine and Nicotine Acid Salts to Nicotine in the Gas Phase," J. Agric. Food Chem. 47(12):5133-5145.

Sekine, H. and Nakahara, Y. (1987). "Abuse of Smoking Methamphetamine Mixed with Tobacco: 1. Inhalation Efficiency and Pyrolysis Products of Methamphetamine," Journal of Forensic Science 32(5):1271-1280.

Streitwieser, A. and Heathcock, C. H. eds., (1981). Introduction to Organic Chemistry. Second edition, Macmillan Publishing Co., Inc., New York, pp. ix-xvi. (Table of Contents).

Tsantilis, S. et al. (2001). "Sintering Time for Silica Particle Growth," Aerosol Science and Technology 34:237-246.

Vapotronics, Inc. (1998) located at http://www.vapotronics.com.au/banner.htm., 11 pages, (visited on Jun. 5, 2000).

Vaughan, N.P. (1990). "The Generation of Monodisperse Fibres of Caffeine" J. Aerosol Sci. 21(3): 453-462.

Ward, M. E. MD, et al. (Dec. 1997). "Morphine Pharmacokinetics after Pulmonary Administration from a Novel Aerosol Delivery System," Clinical Pharmocology & Therapeutics 62(6):596-609.

Williams, S. (Feb. 1999). "Rhone-Poulenc Rorer Inc. and Targacept Inc. Announce Alliance to Develop New Drugs to Treat Alzheimer's and Parkinson's Diseases" located at http://www.rpr.rpna.com/ABOUT_RPR/pressrels/1999/990209-targa.html (last visited on Jan. 28, 2000) 1 page.

Wood, R.W. et al. (1996). "Methylecgonidine Coats the Crack Particle." Pharmacology Biochemistry & Behavior. 53(1):57-66.

Wood, R.W. et al. (1996). "Generation of Stable Test Atmospheres of Cocaine Base and Its Pyrolyzate, Methylecgonidine, and Demonstration of Their Biological Activity." Pharmacology Biochemistry & Behavior. 55(2):237-248.

U.S. Appl. No. 13/311,660, filed Dec. 6, 2011, Bennett et al.

U.S. Appl. No. 13/569,006, filed Aug. 7, 2012, Hale et al.

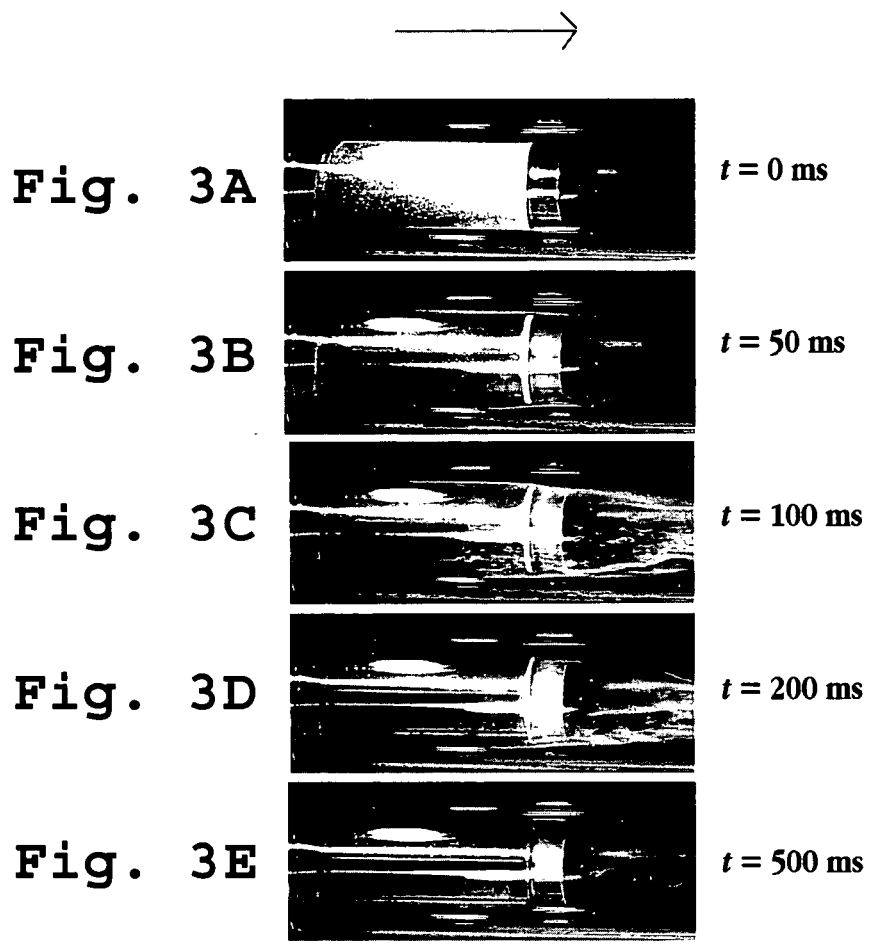
Fig. 3A  $t = 0$ ms
Fig. 3B  $t = 50$ ms
Fig. 3C  $t = 100$ ms
Fig. 3D  $t = 200$ ms
Fig. 3E  $t = 500$ ms
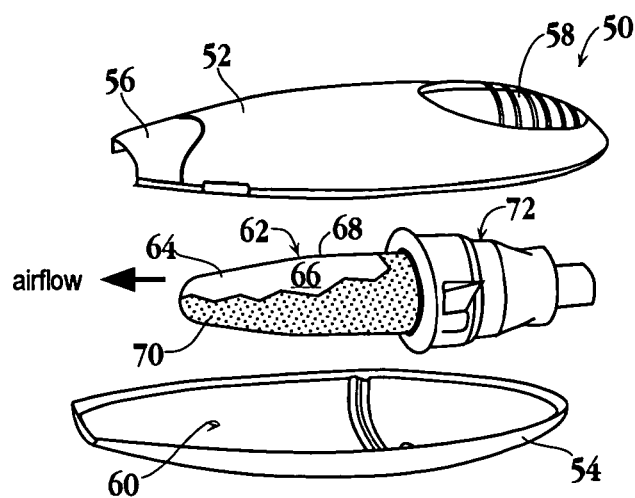
Fig. 2B

Fig. 23 t=0 msec t=50 msec t=100 msec t=200 msec

Fig. 25A  t=0 msec
Fig. 25B  t=50 msec
Fig. 25C  t=100 msec
Fig. 25D  t=200 msec t=0 msec t=50 msec t=100 msec t=200 msec t=300 msec

DRUG CONDENSATION AEROSOLS AND KITS

CROSS REFERENCE TO RELATED APPLICATIONS

The present application is a continuation of U.S. patent application Ser. No. 12/117,737, entitled "Drug Condensation Aerosols And Kits," filed Aug. 8, 2008. U.S. patent application Ser. No. 12/117,737, filed Aug. 8, 2008 is a continuation of U.S. patent application Ser. No. 11/504,419, entitled "Drug Condensation Aerosols and Kits", filed Aug. 15, 2006.

U.S. patent application Ser. No. 11/504,419, filed Aug. 15, 2006 is a continuation of U.S. patent application Ser. No. 10/718,982, entitled "Drug Condensation Aerosols and Kits", filed Nov. 20, 2003, U.S. Pat. No. 7,090,830, issued Aug. 15, 2006.

U.S. patent application Ser. No. 10/718,982, U.S. Pat. No. 7,090,830, is a continuation-in-part of application Ser. No. 10/057,197, filed Oct. 26, 2001, U.S. Pat. No. 7,766,013, issued Aug. 3, 2010, which claims benefit of Provisional Application No. 60/296,225, filed Jun. 5, 2001.

U.S. patent application Ser. No. 10/718,982, U.S. Pat. No. 7,090,830, is also a continuation-in-part of application Ser. No. 10/057,198, filed Oct. 26, 2001, which claims benefit of Provisional Application No. 60/296,225, filed Jun. 5, 2001.

U.S. patent application Ser. No. 10/718,982, U.S. Pat. No. 7,090,830, is also a continuation-in-part of application Ser. No. 10/146,080, filed May 13, 2002, U.S. Pat. No. 7,942,147, issued May 17, 2011, which is a continuation-in-part of application Ser. No. 10/057,198, filed Oct. 26, 2001, which claims the benefit of Provisional Application No. 60/296,225, filed Jun. 5, 2001.

U.S. patent application Ser. No. 10/718,982, U.S. Pat. No. 7,090,830, is also a continuation-in-part of application Ser. No. 10/146,086, filed May 13, 2002, U.S. Pat. No. 7,458,374, issued Dec. 2, 2008.

U.S. patent application Ser. No. 10/718,982, U.S. Pat. No. 7,090,830, is also a continuation-in-part of application Ser. No. 10/146,088, filed May 13, 2002, U.S. Pat. No. 7,537,009, issued May 26, 2009, which is a continuation-in-part of patent application Ser. No. 10/057,198, filed Oct. 26, 2001, which claims the benefit of Provisional Application No. 60/296,225, filed Jun. 5, 2001.

U.S. patent application Ser. No. 10/718,982, U.S. Pat. No. 7,090,830, is also a continuation-in-part of application Ser. No. 10/146,515, filed May 13, 2002, U.S. Pat. No. 6,682,716, issued Jan. 27, 2004, which is a continuation-in-part of patent application Ser. No. 10/057,198, filed Oct. 26, 2001, which claims the benefit of Provisional Application No. 60/296,225, filed Jun. 5, 2001.

U.S. patent application Ser. No. 10/718,982, U.S. Pat. No. 7,090,830, is also a continuation-in-part of application Ser. No. 10/146,516, filed May 13, 2002, U.S. Pat. No. 6,737,042, issued May 18, 2004, which claims the benefit of Provisional Application No. 60/294,203, filed May 24, 2001, and also claims the benefit of Provisional Application No. 60/317,479, filed Sep. 5, 2001.

U.S. patent application Ser. No. 10/718,982, U.S. Pat. No. 7,090,830, is also a continuation-in-part of application Ser. No. 10/150,056, filed May 15, 2002, U.S. Pat. No. 6,805,853, issued Oct. 19, 2004, which claims the benefit of Provisional Application No. 60/345,882, filed Nov. 9, 2001.

U.S. patent application Ser. No. 10/718,982, U.S. Pat. No. 7,090,830, is also a continuation-in-part of application Ser. No. 10/150,267, filed May 15, 2002, U.S. Pat. No. 6,797,259, issued Sep. 28, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/150,268, filed May 15, 2002, U.S. Pat. No. 6,780,399, issued Aug. 24, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/150,591, filed May 17, 2002, U.S. Pat. No. 6,780,400, issued Aug. 24, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/150,857, filed May 17, 2002, U.S. Pat. No. 6,716,415, issued Apr. 6, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/151,596, filed May 16, 2002, U.S. Pat. No. 6,855,310, issued Feb. 15, 2005, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/151,626, filed May 16, 2002, U.S. Pat. No. 6,783,753, issued Aug. 31, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/152,639, filed May 20, 2002, U.S. Pat. No. 6,716,416, issued Apr. 6, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/152,640, filed May 20, 2002, U.S. Pat. No. 6,743,415, issued Jun. 1, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/152,652, filed May 20, 2002, U.S. Pat. No. 6,740,307, issued May 25, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/153,139, filed May 20, 2002, U.S. Pat. No. 6,814,954, issued Nov. 9, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/153,311, filed May 21, 2002, U.S. Pat. No. 6,884,408, issued Apr. 26, 2005, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/153,313, filed May 21, 2002, which claims the benefit of Provisional Application No. 60/294,203, filed May 24, 2001, and of Provisional Application No. 60/317,479, filed Sep. 5, 2001, and of Provisional Application No. 60/345,145, filed Nov. 9, 2001.

U.S. patent application Ser. No. 10/718,982, U.S. Pat. No. 7,090,830, is also a continuation-in-part of application Ser. No. 10/153,831, filed May 21, 2002, U.S. Pat. No. 6,740,308, issued May 25, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/153,839, filed May 21, 2002, U.S. Pat. No. 6,776,978, issued Aug. 17, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/154,594, filed May 23, 2002, U.S. Pat. No. 6,740,309, issued May 25, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/154,765, filed May 23, 2002, U.S. Pat. No. 6,814,955, issued Nov. 9, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/155,097, filed May 23, 2002, U.S. Pat. No. 6,716,417, issued Apr. 6, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/155,373, filed May 22, 2002, U.S. Pat. No. 6,737,043, issued May 18, 2004, which claims the benefit of Provisional Application No. 60/294,203, filed May 24, 2001, and of Provisional Application No. 60/317,479, filed Sep. 5, 2001, and of Provisional Application No. 60/345,876, filed Nov. 9, 2001.

U.S. patent application Ser. No. 10/718,982, U.S. Pat. No. 7,090,830, is also a continuation-in-part of application Ser. No. 10/155,621, filed May 22, 2002, U.S. Pat. No. 6,759,029, issued Jul. 6, 2004, which claims the benefit of Provisional Application No. 60/294,203, filed May 24, 2001, and of Provisional Application No. 60/317,479, filed Sep. 5, 2001, and of Provisional Application No. 60/332,280, filed Nov. 21, 2001, and of Provisional Application No. 60/336,218, filed Oct. 30, 2001.

U.S. patent application Ser. No. 10/718,982, U.S. Pat. No. 7,090,830, is also a continuation-in-part of application Ser. No. 10/155,703, filed May 22, 2002, U.S. Pat. No. 6,803,031, issued Oct. 12, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/155,705, filed May 22, 2002, U.S. Pat. No. 6,805,854, issued Oct. 19, 2004, which claims the benefit of Provisional Application No. 60/294,203, filed May 24, 2001, and of Provisional Application No. 60/317,479, filed Sep. 5, 2001.

U.S. patent application Ser. No. 10/718,982, U.S. Pat. No. 7,090,830, is also a continuation-in-part of application Ser. No. 10/280,315, filed Oct. 25, 2002, which claims the benefit of Provisional Application No. 60/335,049, filed Oct. 30, 2001, and of Provisional Application No. 60/371,457, filed Apr. 9, 2002.

U.S. patent application Ser. No. 10/718,982, U.S. Pat. No. 7,090,830, is also a continuation-in-part of application Ser. No. 10/302,010, filed Nov. 21, 2002, U.S. Pat. No. 7,078,016, issued Jul. 18, 2006, which claims the benefit of Provisional Application No. 60/332,279, filed Nov. 21, 2001.

U.S. patent application Ser. No. 10/718,982, U.S. Pat. No. 7,090,830, is also a continuation-in-part of application Ser. No. 10/302,614, filed Nov. 21, 2002, which claims the benefit of Provisional Application No. 60/332,165, filed Nov. 21, 2001.

U.S. patent application Ser. No. 10/718,982, U.S. Pat. No. 7,090,830, is also a continuation-in-part of application Ser. No. 10/322,227, filed Dec. 17, 2002, which claims the benefit of Provisional Application No. 60/342,066, filed Dec. 18, 2001, and of Provisional Application No. 60/412,068, filed Sep. 18, 2002.

U.S. patent application Ser. No. 10/718,982, U.S. Pat. No. 7,090,830, is also a continuation-in-part of application Ser. No. 10/633,877 filed Aug. 4, 2003, U.S. Pat. No. 7,585,493, issued Sep. 8, 2009.

U.S. patent application Ser. No. 10/718,982, U.S. Pat. No. 7,090,830, is also a continuation-in-part of application Ser. No. 10/633,876 filed Aug. 4, 2003, U.S. Pat. No. 7,645,442, issued Jan. 12, 2010.

All of the applications cited above are incorporated by reference in their entirety. Any disclaimer that may have occurred during the prosecution of the above-referenced application(s) is hereby expressly rescinded, and reconsideration of all relevant art is respectfully requested.

FIELD OF THE INVENTION

The present invention relates generally to the field of drug aerosols and kits for delivering drug aerosols. More specifically, the invention relates to a condensation drug aerosol where the drug itself is vaporized.

BACKGROUND

There are a number of drug compositions commercially available for the treatment of disease. These drugs are most commonly delivered as an oral dosage form (e.g. as a pill, capsule, or tablet), or delivered intravenously. Disadvantages of oral dosage forms include a delay in the onset of activity and loss of drug therapeutic effect due to hepatic first-pass metabolism. Intravenous delivery, while typically more effective than oral delivery, is often painful and inconvenient. Thus other dosage forms and routes of administration with improved properties are desirable.

One such alternative is inhalation therapy. Many preclinical and clinical studies with inhaled compounds have demonstrated that efficacy can be achieved both within the lungs and systemically. Moreover, there are many advantages associated with pulmonary delivery including rapid onset, the convenience of patient self-administration, the potential for reduced drug side-effects, ease of delivery by inhalation, the elimination of needles, and the like. Yet, in spite of these advantages, pulmonary delivery through inhalation therapy has played a relatively minor role in the administration of therapeutic agents when compared to more traditional drug administration routes of oral delivery and delivery via injection.

The role of inhalation therapy in the health care field has remained limited mainly to treatment of asthma, in part due to a set of problems unique to the development of inhalable drug formulations, especially formulations for systemic delivery by inhalation. Inhalation aerosols from dry powder inhalers, nebulizers, and pressurized metered dose inhalers typically include excipients or solvents to increase stability or deliverability of these drugs in an aerosol form. Additionally, control of the particle size of these drug aerosols is challenging and depends on the method used to form the aerosol and the other excipients added.

For example, when using dry powder inhalers (DPI's), the need to mill the drug to obtain an acceptable particle size for delivery to the lungs is problematic. Some mills used for micronization are known to produce heat, which can cause degradation of the drug if prolonged, and tend to shed metallic particles as contaminants. Moreover, as dry powder formulations are prone to aggregation and low flowability which can result in diminished efficiency, scrupulous attention is required during milling, blending, powder flow, filling and even administration to ensure that the dry powder aerosols are reliably delivered and have the proper particle size distribution for delivery to the lungs.

Nebulizers generate an aerosol from a liquid, some by breakup of a liquid jet and some by ultrasonic vibration of the liquid with or without a nozzle. All liquid aerosol devices must overcome the problems associated with formulation of the compound into a stable liquid state. Liquid formulations must be prepared and stored under aseptic or sterile conditions since they can harbor microorganisms. This necessitates the use of preservatives or unit dose packaging. Additionally solvents, detergents and other agents are used to stabilize the drug formulation.

Pressurized metered dose inhalers, or pMDIs, are an additional class of aerosol dispensing devices. pMDI's package the compound in a canister under pressure with a solvent and propellant mixture, usually chlorofluorocarbons (CFC's), or hydrofluoroalkanes (HFA's). Upon being dispensed a jet of the mixture is ejected through a valve and nozzle and the propellant "flashes off" leaving an aerosol of the compound. With pMDI's particle size is hard to control and has poor reproducibility leading to uneven and unpredictable bioavailability. Moreover, due to the high speed ejection of the aerosol from the nozzle, pMDIs deliver drug inefficiently as much of the drug impacts ballistically on the tongue, mouth and throat and never gets to the lung.

Thus, there remains a need for methods to prepare aerosols that are readily deliverable and have minimal formulation issues. One such method is to deliver drugs via vaporization.

When using vaporization to form an aerosol, controlling a compound's degradation and anticipating the energies which activate thermal degradation are typically very difficult. Activation energies of these reactions depend on molecular structures, energy transfer mechanisms, transitory configurations of the reacting molecular complexes, and the effects of neighboring molecules. Thus, while vaporization followed by condensation of the vapor to form an aerosol provides a possible mechanism to eliminate the need for costly formulations, which include excipients and other materials that are likely to change the pharmcokinetics and bioavailability of a drug, the challenge of using this technique for generating drug aerosols resides in the ability to control thermal degradation during the vaporization step.

The present invention overcomes the foregoing discussed disadvantages and problems with other inhalation technologies and provides a mechanism to control thermal degradation during vaporization making it possible to produce pure aerosols of organic compounds without the need for excipients or other additives, including solvents, wherein the particle size is stable and selectable.

SUMMARY

In one aspect, the invention provides novel composition for delivery of a drug comprising a condensation aerosol formed by volatilizing a heat stable drug composition under conditions effective to produce a heated vapor of said drug composition and condensing the heated vapor of the drug composition to form condensation aerosol particles, wherein said condensation aerosol particles are characterized by less than 10% drug degradation products, and wherein the aerosol MMAD is less than 3 microns.

In some variations, the aerosol comprises at least 50% by weight of drug condensation particles. In other variations the aerosol comprises at least 90% or 95% by weight of the drug condensation particles. Similarly, in some variations, the aerosol is substantially free of thermal degradation products, and in some variations, the condensation aerosol has a MMAD in the range of 1-3 µm. In certain embodiments, the particles have an MMAD of less than 5 microns, preferably less than 3 microns. Preferably, the particles have a mass median aerodynamic diameter of from 0.2 to 5 microns, or most preferably from 0.2 to 3 microns. Also, in some variations the molecular weight of the compound is typically between 200 and 700. Typically, the aerosol comprises a therapeutically effective amount of drug and in some variations may comprise pharmaceutically acceptable excipients. In some variations, the carrier gas is air. In some variations, other gases or a combination of various gases may be used.

In another aspect of the invention, the invention provides compositions for inhalation therapy, comprising an aerosol of vaporized drug condensed into particles, characterized by less than 5% drug degradation products, and wherein said aerosol has a mass median aerodynamic diameter between 1-3 microns.

In some variations of the aerosol compositions, the carrier gas is a non-propellant, non-organic solvent carrier gas. In other variations, the aerosol is substantially free of organic solvents and propellants.

In yet other embodiments, aerosols of a therapeutic drug are provided that contain less than 5% drug degradation products, and a mixture of a carrier gas and condensation particles, formed by condensation of a vapor of the drug in said carrier gas; where the MMAD of the aerosol increases over time, within the size range of 0.01 to 3 microns as said vapor cools by contact with the carrier gas.

In some variations, the aerosol comprises at least 50% by weight of drug condensation particles. In other variations the aerosol comprises at least 90% or 95% by weight of the drug condensation particles. In some variations, the MMAD of the aerosol is less than 1 micron and increases over time. Also, in some variations the molecular weight of the compound is typically between 200 and 700. In other variations, the compound has a molecular weight of greater than 350 and is heat stable. Typically, the aerosol comprises a therapeutically effective amount of drug and in some variations may comprise pharmaceutically acceptable excipients. In some variations, the carrier gas is air. In some variations, other gases or a combination of various gases may be used.

The condensation aerosols of the various embodiments are typically formed by preparing a film containing a drug composition of a desired thickness on a heat-conductive and impermeable substrate and heating said substrate to vaporize said film, and cooling said vapor thereby producing aerosol particles containing said drug composition. Rapid heating in combination with the gas flow helps reduce the amount of decomposition. Thus, a heat source is used that typically heats the substrate to a temperature of greater than 200° C., preferably at least 250° C., more preferably at least 300° C. or 350° C. and produces substantially complete volatilization of the drug composition from the substrate within a period of 2 seconds, preferably, within 1 second, and more preferably, within 0.5 seconds.

Typically, the gas flow rate over the vaporizing compound is between about 4 and 50 L/minute.

The film thickness is such that an aerosol formed by vaporizing the compound by heating the substrate and condensing the vaporized compound contains 10% by weight or less drug-degradation product. The use of thin films allows a more rapid rate of vaporization and hence, generally, less thermal drug degradation. Typically, the film has a thickness between 0.05 and 20 microns. In some variations, the film has a thickness between 0.5 and 5 microns. The selected area of the substrate surface expanse is such as to yield an effective human therapeutic dose of the drug aerosol.

Exemplary compounds for use in the invention, and corresponding film thickness ranges are:

alprazolam, film thickness between 0.1 and 10 μm;
amoxapine, film thickness between 2 and 20 μm;
atropine, film thickness between 0.1 and 10 μm;
bumetanide film thickness between 0.1 and 5 μm;
buprenorphine, film thickness between 0.05 and 10 μm;
butorphanol, film thickness between 0.1 and 10 μm;
clomipramine, film thickness between 1 and 8 μm;
donepezil, film thickness between 1 and 10 μm;
hydromorphone, film thickness between 0.05 and 10 μm;
loxapine, film thickness between 1 and 20 μm;
midazolam, film thickness between 0.05 and 20 μm;
morphine, film thickness between 0.2 and 10 μm;
nalbuphine, film thickness between 0.2 and 5 μm;
naratriptan, film thickness between 0.2 and 5 μm;
olanzapine, film thickness between 1 and 20 μm;
paroxetine, film thickness between 1 and 20 μm;
pramipexole, film thickness between 0.05 and 10 μm;
prochlorperazine, film thickness between 0.1 and 20 μm;
quetiapine, film thickness between 1 and 20 μm;
rizatriptan, film thickness between 0.2 and 20 μm;
sertraline, film thickness between 1 and 20 μm;
sibutramine, film thickness between 0.5 and 2 μm;
sildenafil, film thickness between 0.2 and 3 μm;
sumatriptan, film thickness between 0.2 and 6 μm;
tadalafil, film thickness between 0.2 and 5 μm;
vardenafil, film thickness between 0.1 and 2 μm;
venlafaxine, film thickness between 2 and 20 μm;
zolpidem, film thickness between 0.1 and 10 μm;
apomorphine HCl, film thickness between 0.1 and 5 μm;
celecoxib, film thickness between 2 and 20 μm;
ciclesonide, film thickness between 0.05 and 5 μm;
eletriptan, film thickness between 0.2 and 20 μm;
parecoxib, film thickness between 0.5 and 2 μm;
valdecoxib, film thickness between 0.5 and 10 μm;
fentanyl, film thickness between 0.05 and 5 μm;
citalopram, film thickness between 1 and 20 μm;
escitalopram, film thickness between 0.2 and 20 μm;
clonazepam, film thickness between 0.05 and 8 μm;
oxymorphone, film thickness between 0.1 and 10 μm;
albuterol, film thickness between 0.2 and 2 μm;
sufentanyl, film thickness between 0.05 and 5 μm; and
remifentanyl, film thickness between 0.05 and 5 μm.

In a related aspect, the invention includes kits for delivering a drug condensation aerosol that typically comprises a composition devoid of solvents and excipients and comprising a heat stable drug, and a device for forming and delivering via inhalation a condensation aerosol. The device for forming a drug aerosol typically comprises an element configured to heat the composition to form a vapor, an element allowing the vapor to condense to form a condensation aerosol, and an element permitting a user to inhale the condensation aerosol. Typically, the element configured to heat the composition comprises a heat-conductive substrate and formed on the substrate is typically a drug composition film containing a therapeutically effective dose of a drug when the drug is administered in an aerosol form. A heat source in the device is operable to supply heat to the substrate to produce a substrate temperature, typically that is greater than 300° C., to substantially volatilize the drug composition film from the substrate in a period of 2 seconds or less, more preferably, in a period of 500 milliseconds or less. The device may further comprise features such as breath-actuation or lockout elements.

In yet another aspect of the invention kits are provided for delivering a drug aerosol comprising a thin film of a drug composition and a device for dispensing said film as a condensation aerosol. Typically, the film thickness is between 0.5 and 20 microns. The film can comprise pharmaceutically acceptable excipients and is typically heated at a rate so as to substantially volatilize the film in 500 milliseconds or less.

These and other objects and features of the invention will be more fully appreciated when the following detailed description of the invention is read in conjunction with the accompanying drawings.

BRIEF DESCRIPTION OF THE DRAWINGS

FIGS. 1A-1B are cross-sectional views of general embodiments of a drug-supply article in accordance with the invention;

FIG. 2A is a perspective view of a drug-delivery device that incorporates a drug-supply article;

FIG. 2B shows another drug-delivery device that incorporates a drug-supply article, where the device components are shown in unassembled form;

FIGS. 3A-3E are high-speed photographs showing the generation of aerosol particles from a drug-supply unit;

FIGS. 4A-4B are plots of substrate temperature increase, measured in still air with a thin thermocouple (Omega, Model CO2-K), as a function of time. The substrate in FIG. 4A was heated resistively by connection to a capacitor charged to 13.5 Volts (lower line), 15 Volts (middle line), and 16 Volts (upper line); the substrate in FIG. 4B was heated resistively by discharge of a capacitor at 16 Volts;

FIGS. 5A-5B are plots of substrate temperature, in ° C., as a function of time, in seconds, for a hollow stainless steel cylindrical substrate heated resistively by connection to a capacitor charged to 21 Volts, where FIG. 5A shows the temperature profile over a 4 second time period and FIG. 5B is a detail showing the temperature profile over the first second of heating;

FIG. 6 is plot showing purity of thermal vapor as a function of drug film thickness, in micrometers, for the drug atropine free base;

FIG. 7 is plot showing purity of thermal vapor as a function of drug film thickness, in micrometers, for donepezil free base;

FIG. 8 is plot showing purity of thermal vapor as a function of drug film thickness, in micrometers, for hydromorphone free base;

FIG. 9 is plot showing purity of thermal vapor as a function of drug film thickness, in micrometers, for buprenorphine free base;

Figures 10, 11:
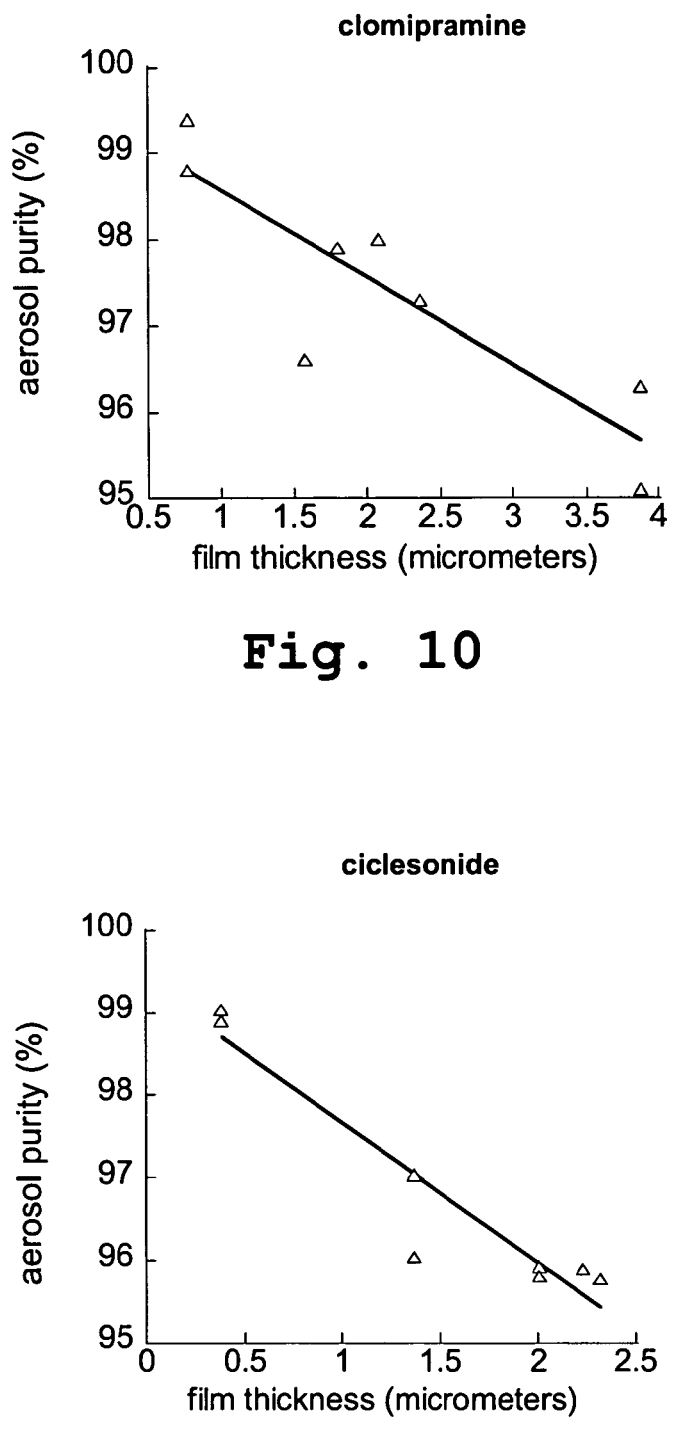

FIG. 10 is plot showing purity of thermal vapor as a function of drug film thickness, in micrometers, for clomipramine free base;

FIG. 11 is plot showing purity of thermal vapor as a function of drug film thickness, in micrometers, for ciclesonide;

FIG. 18 is plot showing purity of thermal vapor as a function of drug film thickness, in micrometers, for prochlorperazine free base;

FIG. 19 is plot showing purity of thermal vapor as a function of drug film thickness, in micrometers, for zolpidem free base;

FIG. 22 is plot showing purity of thermal vapor as a function of drug film thickness, in micrometers, for sildenafil free base;

FIG. 23 is plot showing purity of thermal vapor as a function of drug film thickness, in micrometers, for albuterol free base;

Figure 26A:
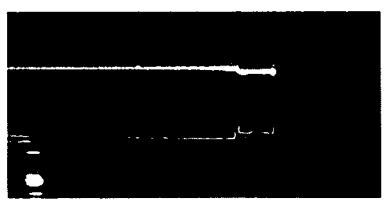
Figure 26B:
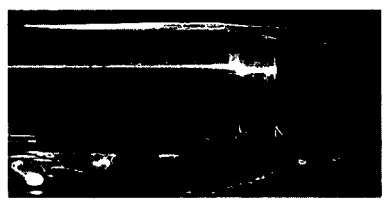
Figure 26C:
Figure 26D:
Figure 26E:

FIGS. 25A-25D are high speed photographs showing the generation of a thermal vapor of disopyramide from a film of drug coated on a substrate drug-supply unit, where the photographs are taken at prior to substrate heating (t=0 ms, FIG. 25A) and during substrate heating at times of 50 milliseconds (FIG. 25B), 100 milliseconds (FIG. 25C), and 200 milliseconds (FIG. 25D); and FIGS. 26A-26E are high speed photographs showing the generation of a thermal vapor of buprenorphine from a film of drug coated on a substrate drug-supply unit, where the photographs are taken at prior to substrate heating (t=0 ms, FIG. 26A) and during substrate heating at times of 50 milliseconds (FIG. 26B), 100 milliseconds (FIG. 26C), 200 milliseconds (FIG. 26D), and 300 milliseconds (FIG. 26E).

Figure 27:
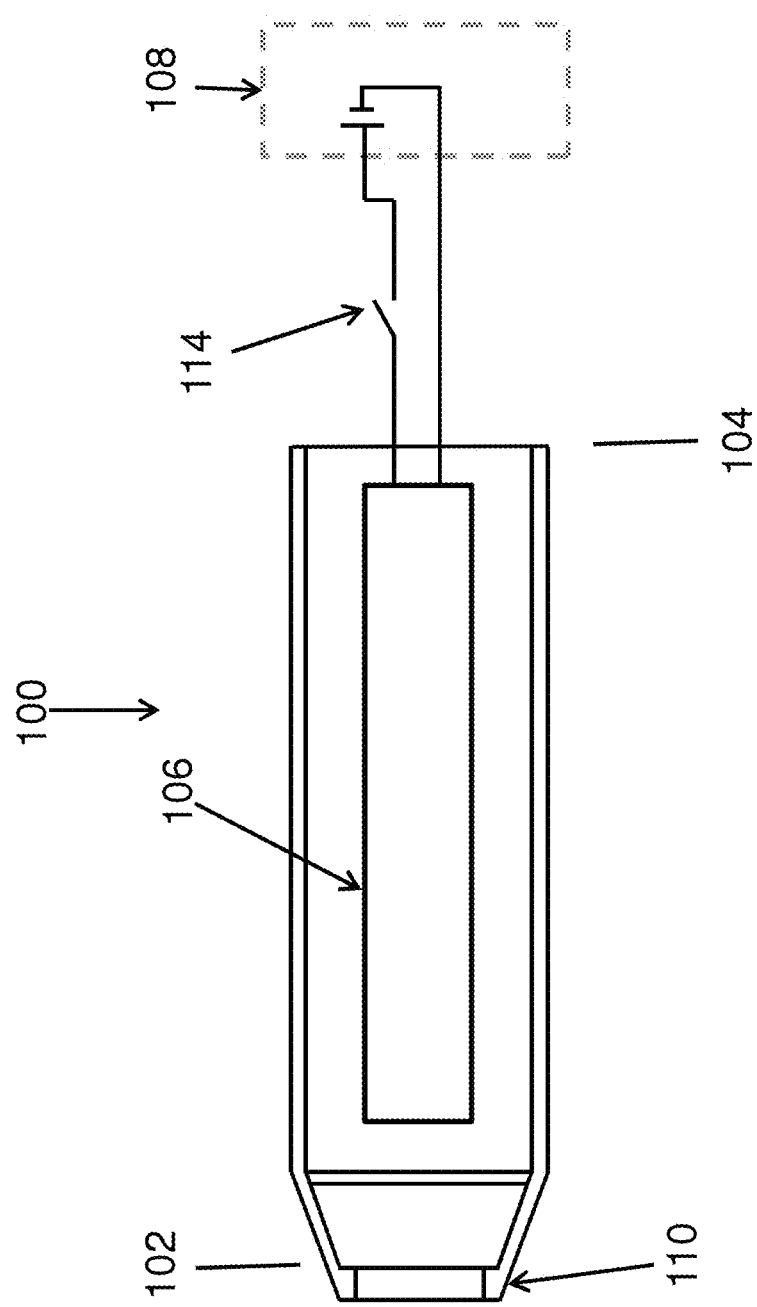

FIG. 27 is an illustration of an exemplary device that may be used to form and administer the aerosols described herein.

DETAILED DESCRIPTION

Definitions

As defined herein, the following terms shall have the following meanings when reference is made to them throughout the specification.

"Aerodynamic diameter" of a given particle refers to the diameter of a sp an aerodynamic diameter larger than the MMAD and half by particles with an aerodynamic diameter smaller than the MMAD.

"Number concentration" refers to the number of particles per unit volume of aerosol.

"Purity" as used herein, with respect to the aerosol purity, means the fraction of drug composition in the aerosol/the fraction of drug composition in the aerosol plus drug degradation products. Thus purity is relative with regard to the purity of the starting material. For example, when the starting drug or drug composition used for substrate coating contained detectable impurities, the reported purity of the aerosol does not include those impurities present in the starting material that were also found in the aerosol, e.g., in certain cases if the starting material contained a 1% impurity and the aerosol was found to contain the identical 1% impurity, the aerosol purity may nevertheless be reported as >99% pure, reflecting the fact that the detectable 1% purity was not produced during the vaporization-condensation aerosol generation process.

"Settling velocity" refers to the terminal velocity of an aerosol particle undergoing gravitational settling in air.

"Support" refers to a material on which the composition is adhered, typically as a coating or thin film. The term "support" and "substrate" are used herein interchangeably.

"Substantially free of" means that the material, compound, aerosol, etc., being described is at least 95% free of the other component from which it is substantially free.

"Typical patient tidal volume" refers to 1 L for an adult patient and 15 mL/kg for a pediatric patient.

"Therapeutically effective amount" means the amount required to achieve a therapeutic effect. The therapeutic effect could be any therapeutic effect ranging from prevention, symptom amelioration, symptom treatment, to disease termination or cure.

"Thermal stability ratio" or "TSR" means the % purity/(100%−% purity) if the % purity is <99.9%, and 1000 if the % purity is ≥99.9%. For example, a respiratory drug vaporizing at 90% purity would have a TSR of 9. An example of how to determine whether a respiratory drug is heat stable is provided in Example 237.

"4 µm thermal stability ratio" or "4TSR" means the TSR of a drug determined by heating a drug-comprising film of about 4 microns in thickness under conditions sufficient to vaporize at least 50% of the drug in the film, collecting the resulting aerosol, determining the purity of the aerosol, and using the purity to compute the TSR. In such vaporization, generally the about 4-micron thick drug film is heated to around 350° C. but not less than 200° C. for around 1 second to vaporize at least 50% of the drug in the film.

"1.5 µm thermal stability ratio" or "1.5TSR" means the TSR of a drug determined by heating a drug-comprising film of about 1.5 microns in thickness under conditions sufficient to vaporize at least 50% of the drug in the film, collecting the resulting aerosol, determining the purity of the aerosol, and using the purity to compute the TSR. In such vaporization, generally the about 1.5-micron thick drug film is heated to around 350° C. but not less than 200° C. for around 1 second to vaporize at least 50% of the drug in the film.

"0.5 µm thermal stability ratio" or "0.5TSR" means the TSR of a drug determined by heating a drug-comprising film of about 0.5 microns in thickness under conditions sufficient to vaporize at least 50% of the drug in the film, collecting the resulting aerosol, determining the purity of the aerosol, and using the purity to compute the TSR. In such vaporization, generally the about 0.5-micron thick drug film is heated to around 350° C. but not less than 200° C. for around 1 second to vaporize at least 50% of the drug in the film.

"Vapor" refers to a gas, and "vapor phase" refers to a gas phase. The term "thermal vapor" refers to a vapor phase, aerosol, or mixture of aerosol-vapor phases, formed preferably by heating.

Aerosol Composition

The compositions described herein typically comprise at least one drug compound. The drug compositions may comprise other compounds as well. For example, the composition may comprise a mixture of drug compounds, a mixture of a drug compound and a pharmaceutically acceptable excipient, or a mixture of a drug compound with other compounds having useful or desirable properties. The composition may comprise a pure drug compound as well. In preferred embodiments, the composition consists essentially of pure drug and contains no propellants or solvents.

Any suitable drug compound may be used. Drugs that can be used include, for example but not limitation, drugs of one of the following classes: anesthetics, anticonvulsants, antidepressants, antidiabetic agents, antidotes, antiemetics, antihistamines, anti-infective agents, antineoplastics, antiparkisonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

Typically, where the drug is an anesthetic, it is selected from one of the following compounds: ketamine and lidocaine.

Typically, where the drug is an anticonvulsant, it is selected from one of the following classes: GABA analogs, tiagabine, vigabatrin; barbiturates such as pentobarbital; benzodiazepines such as clonazepam; hydantoins such as phenyloin; phenyltriazines such as lamotrigine; miscellaneous anticonvulsants such as carbamazepine, topiramate, valproic acid, and zonisamide.

Typically, where the drug is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

Typically, where the drug is an antidiabetic agent, it is selected from one of the following compounds: pioglitazone, rosiglitazone, and troglitazone.

Typically, where the drug is an antidote, it is selected from one of the following compounds: edrophonium chloride, flumazenil, deferoxamine, nalmefene, naloxone, and naltrexone.

Typically, where the drug is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

Typically, where the drug is an antihistamine, it is selected from one of the following compounds: astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

Typically, where the drug is an anti-infective agent, it is selected from one of the following classes: antivirals such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefmetazole, cefazolin, cephalexin, cefoperazone, cefoxitin, cephacetrile, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

Typically, where the drug is an anti-neoplastic agent, it is selected from one of the following compounds: droloxifene, tamoxifen, and toremifene.

Typically, where the drug is an antiparkisonian drug, it is selected from one of the following compounds: amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Typically, where the drug is an antirheumatic agent, it is selected from one of the following compounds: diclofenac, hydroxychloroquine and methotrexate.

Typically, where the drug is an antipsychotic, it is selected from one of the following compounds: acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine, and zuclopenthixol.

Typically, where the drug is an anxiolytic, it is selected from one of the following compounds: alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

Typically, where the drug is an appetite stimulant, it is dronabinol.

Typically, where the drug is an appetite suppressant, it is selected from one of the following compounds: fenfluramine, phentermine and sibutramine.

Typically, where the drug is a blood modifier, it is selected from one of the following compounds: cilostazol and dipyridamol.

Typically, where the drug is a cardiovascular agent, it is selected from one of the following compounds: benazepril, captopril, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocamide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazem, nifedipine, verapamil, spironolactone, bumetanide, ethacrynic acid, furosemide, torsemide, amiloride, triamterene, and metolazone.

Typically, where the drug is a central nervous system stimulant, it is selected from one of the following compounds: amphetamine, brucine, caffeine, dexfenfluramine, dextroamphetamine, ephedrine, fenfluramine, mazindol, methyphenidate, pemoline, phentermine, sibutramine, and modafinil.

Typically, where the drug is a drug for Alzheimer's disease management, it is selected from one of the following compounds: donepezil, galanthamine and tacrin.

Typically, where the drug is a drug for cystic fibrosis management, it is selected from one of the following compounds: CPX, IBMX, XAC and analogues; 4-phenylbutyric acid; genistein and analogous isoflavones; and milrinone.

Typically, where the drug is a diagnostic agent, it is selected from one of the following compounds: adenosine and aminohippuric acid.

Typically, where the drug is a dietary supplement, it is selected from one of the following compounds: melatonin and vitamin-E.

Typically, where the drug is a drug for erectile dysfunction, it is selected from one of the following compounds: tadalafil, sildenafil, vardenafil, apomorphine, apomorphine diacetate, phentolamine, and yohimbine.

Typically, where the drug is a gastrointestinal agent, it is selected from one of the following compounds: loperamide, atropine, hyoscyamine, famotidine, lansoprazole, omeprazole, and rebeprazole.

Typically, where the drug is a hormone, it is selected from one of the following compounds: testosterone, estradiol, and cortisone.

Typically, where the drug is a drug for the treatment of alcoholism, it is selected from one of the following compounds: naloxone, naltrexone, and disulfuram.

Typically, where the drug is a drug for the treatment of addiction it is buprenorphine.

Typically, where the drug is an immunosupressive, it is selected from one of the following compounds: mycophenolic acid, cyclosporin, azathioprine, tacrolimus, and rapamycin.

Typically, where the drug is a mast cell stabilizer, it is selected from one of the following compounds: cromolyn, pemirolast, and nedocromil.

Typically, where the drug is a drug for migraine headache, it is selected from one of the following compounds: almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the drug is a motion sickness product, it is selected from one of the following compounds: diphenhydramine, promethazine, and scopolamine.

Typically, where the drug is a drug for multiple sclerosis management, it is selected from one of the following compounds: bencyclane, methylprednisolone, mitoxantrone, and prednisolone.

Typically, where the drug is a muscle relaxant, it is selected from one of the following compounds: baclofen, chlorzoxazone, cyclobenzaprine, methocarbamol, orphenadrine, quinine, and tizanidine.

Typically, where the drug is a nonsteroidal anti-inflammatory, it is selected from one of the following compounds: aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Typically, where the drug is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Typically, where the drug is another analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the drug is an opthalmic preparation, it is selected from one of the following compounds: ketotifen and betaxolol.

Typically, where the drug is an osteoporosis preparation, it is selected from one of the following compounds: alendronate, estradiol, estropitate, risedronate and raloxifene.

Typically, where the drug is a prostaglandin, it is selected from one of the following compounds: epoprostanol, dinoprostone, misoprostol, and alprostadil.

Typically, where the drug is a respiratory agent, it is selected from one of the following compounds: albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, and pirfenidone Typically, where the drug is a sedative and hypnotic, it is selected from one of the following compounds: butalbital, chlordiazepoxide, diazepam, estazolam, flunitrazepam, flurazepam, lorazepam, midazolam, temazepam, triazolam, zaleplon, zolpidem, and zopiclone.

Typically, where the drug is a skin and mucous membrane agent, it is selected from one of the following compounds: isotretinoin, bergapten and methoxsalen.

Typically, where the drug is a smoking cessation aid, it is selected from one of the following compounds: nicotine and varenicline.

Typically, where the drug is a Tourette's syndrome agent, it is pimozide.

Typically, where the drug is a urinary tract agent, it is selected from one of the following compounds: tolteridine, darifenicin, propantheline bromide, and oxybutynin.

Typically, where the drug is a vertigo agent, it is selected from one of the following compounds: betahistine and meclizine.

In general, we have found that suitable drug have properties that make them acceptable candidates for use with the devices and methods herein described. For example, the drug compound is typically one that is, or can be made to be, vaporizable. Typically, the drug is a heat stable drug. Exemplary drugs include acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenyloin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocamide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol- 3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, and triamcinolone acetonide and pharmaceutically acceptable analogs and equivalents thereof.

The drug may be one that when vaporized from a film on an impermeable surface of a heat conductive substrate, the aerosol exhibits an increasing level of drug composition degradation products with increasing film thickness. Examples include but are not limited to the following drugs, and associated ranges of film thicknesses:

alprazolam, film thickness between 0.1 and 10 μm;
amoxapine, film thickness between 2 and 20 μm;
atropine, film thickness between 0.1 and 10 μm;
bumetanide film thickness between 0.1 and 5 μm;
buprenorphine, film thickness between 0.05 and 10 μm;
butorphanol, film thickness between 0.1 and 10 μm;
clomipramine, film thickness between 1 and 8 μm;
donepezil, film thickness between 1 and 10 μm;
hydromorphone, film thickness between 0.05 and 10 μm;
loxapine, film thickness between 1 and 20 μm;
midazolam, film thickness between 0.05 and 20 μm;
morphine, film thickness between 0.2 and 10 μm;
nalbuphine, film thickness between 0.2 and 5 μm;
naratriptan, film thickness between 0.2 and 5 μm;
olanzapine, film thickness between 1 and 20 μm;
paroxetine, film thickness between 1 and 20 μm;
prochlorperazine, film thickness between 0.1 and 20 μm;
pramipexole, film thickness between 0.05 and 10 μm;
quetiapine, film thickness between 1 and 20 μm;
rizatriptan, film thickness between 0.2 and 20 μm;
sertraline, film thickness between 1 and 20 μm;
sibutramine, film thickness between 0.5 and 2 μm;
sildenafil, film thickness between 0.2 and 3 μm;
sumatriptan, film thickness between 0.2 and 6 μm;
tadalafil, film thickness between 0.2 and 5 μm;
vardenafil, film thickness between 0.1 and 2 μm;
venlafaxine, film thickness between 2 and 20 μm;
zolpidem, film thickness between 0.1 and 10 μm;
apomorphine HCl, film thickness between 0.1 and 5 μm;
celecoxib, film thickness between 2 and 20 μm;
ciclesonide, film thickness between 0.05 and 5 μm;
eletriptan, film thickness between 0.2 and 20 μm;
parecoxib, film thickness between 0.5 and 2 μm;
valdecoxib, film thickness between 0.5 and 10 μm;
fentanyl, film thickness between 0.05 and 5 μm;
citalopram, film thickness between 1 and 20 μm;
escitalopram, film thickness between 0.2 and 20 μm;
clonazepam, film thickness between 0.05 and 8 μm;
oxymorphone, film thickness between 0.1 and 10 μm;
albuterol, film thickness between 0.2 and 2 μm;
sufentanyl, film thickness between 0.05 and 5 μm; and
remifentanyl, film thickness between 0.05 and 5 μm.

Typically, the drugs of use in the invention have a molecular weight in the range of about 150-700, preferably in the range of about 200-700, more preferably in the range of 250-600, still more preferably in the range of about 250-500. In some variations, the drugs have a molecular weight in the range 350-600 and in others the drugs have a molecular weigh in the range of about 300-450. In other variations, where the drug is a heat stable drug, the drug can have a molecular weight of 350 or greater.

Typically, the compound is in its ester, free acid, or its free-base form. However, it is not without possibility that the compound will be vaporizable from its salt form. Indeed, a variety of pharmaceutically acceptable salts are suitable for aerosolization. Illustrative salts include, without limitation, the following: hydrochloric acid, hydrobromic acid, acetic acid, maleic acid, formic acid, and fumaric acid salts. Salt forms can be purchased commercially, or can be obtained from their corresponding free acid or free base forms using well known methods in the art.

Suitable pharmaceutically acceptable excipients may be volatile or nonvolatile. Volatile excipients, when heated, are concurrently volatilized, aerosolized and inhaled with the drug. Classes of such excipients are known in the art and include, without limitation, gaseous, supercritical fluid, liquid and solid solvents. The following is a list of exemplary carriers within these classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Additionally, pharmaceutically acceptable carriers, surfactants, enhancers, and inorganic compounds may be included in the composition. Examples of such materials are known in the art.

In some variations, the aerosols are substantially free of organic solvents and propellants. Additionally, water is typically not added as a solvent for the drug, although water from the atmosphere may be incorporated in the aerosol during formation, in particular, while passing air over the film and during the cooling process. In other variations, the aerosols are completely devoid of organic solvents and propellants. In yet other variations, the aerosols are completely devoid of organic solvents, propellants, and any excipients. These aerosols comprise only pure drug, less than 10% drug degradation products, and a carrier gas, which is typically air.

Typically, the drug has a decomposition index less than 0.15. Preferably, the drug has a decomposition index less than 0.10. More preferably, the drug has a decomposition index less than 0.05. Most preferably, the drug has a decomposition index less than 0.025

In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations, the condensation aerosol particles comprise less than 10% by weight of a thermal degradation product. In other variations, the condensation drug aerosol particles comprise less than 5%, 1%, 0.5%, 0.1%, or 0.03% by weight of a thermal degradation product.

In certain embodiments of the invention, the drug aerosol has a purity of between 90% and 99.8%, or between 93% and 99.7%, or between 95% and 99.5%, or between 96.5% and 99.2%.

Typically, the aerosol has a number concentration greater than $10^6$ particles/mL. In other variations, the aerosol has a number concentration greater than $10^7$ particles/mL. In yet other variations, the aerosol has a number concentration greater than $10^8$ particles/mL, greater than $10^9$ particles/mL, greater than $10^{10}$ particles/mL, or greater than $10^{11}$ particles/mL.

The gas of the aerosol typically is air. Other gases, however, can be used, in particular inert gases, such as argon, nitrogen, helium, and the like. The gas can also include vapor of the composition that has not yet condensed to form particles. Typically, the gas does not include propellants or vaporized organic solvents. In some variations, the condensation aerosol comprises at least 5% by weight of condensation drug aerosol particles. In other variations, the aerosol comprises at least 10%, 20%, 30%, 40%, 50%, 60%, or 75% by weight of condensation drug aerosol particles. In still other variations, the aerosol comprises at least 95%, 99%, or 99.5% by weight of condensation aerosol particles.

In some variations the condensation drug aerosol has a MMAD in the range of about 1-3 μm. In some variations the geometric standard deviation around the MMAD of the condensation drug aerosol particles is less than 3.0. In other variations, the geometric standard deviation around the MMAD of the condensation drug aerosol particles is less than 2.5, or less than 2.0.

In certain embodiments of the invention, the drug aerosol comprises one or more drugs having a 4TSR of at least 5 or 10, a 1.5TSR of at least 7 or 14, or a 0.5TSR of at least 9 or 18. In other embodiments of the invention, the drug aerosol comprises one or more drugs having a 4TSR of between 5 and 100 or between 10 and 50, a 1.5TSR of between 7 and 200 or between 14 and 100, or a 0.5TSR of between 9 and 900 or between 18 and 300.

Formation of Condensation Aerosols

Any suitable method may be used to form the condensation aerosols described herein. One such method involves the heating of a composition to form a vapor, followed by cooling of the vapor so that it forms an aerosol (i.e., a condensation aerosol).

Typically, the composition is coated on a substrate, and then the substrate is heated to vaporize the composition. The substrate may be of any geometry and be of a variety of different sizes. It is often desirable that the substrate provide a large surface to volume ratio (e.g., greater than 100 per meter) and a large surface to mass ratio (e.g., greater than 1 $cm^2$ per gram). The substrate can have more than one surface A substrate of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials may be used to construct the substrate. Typically, the substrates are heat-conductive and include metals, such as aluminum, iron, copper, stainless steel, and the like, alloys, ceramics, and filled polymers. In one variation, the substrate is stainless steel. Combinations of materials and coated variants of materials may be used as well.

When it is desirable to use aluminum as a substrate, aluminum foil is a suitable material. Examples of alumina and silicon based materials BCR171 (an alumina of defined surface area greater than 2 $m^2/g$ from Aldrich, St. Louis, Mo.) and a silicon wafer as used in the semiconductor industry.

Typically it is desirable that the substrate have relatively few, or substantially no, surface irregularities. Although a variety of supports may be used, supports that have an impermeable surface, or an impermeable surface coating, are typically desirable. Illustrative examples of such supports include metal foils, smooth metal surfaces, nonporous ceramics, and the like. Alternatively, or in addition, to preferred substrates having an impermeable surface, the substrate surface expanse is characterized by a contiguous surface area of greater than 1 $mm^2$, preferably 10 $mm^2$, more preferable 50 $mm^2$ and still more preferably 100 $mm^2$, and a material density of greater than 0.5 g/cc. In contrast, non-preferred substrates typically have a substrate density of less than 0.5 g/cc, such as, for example, yarn, felts and foam, or have a surface area of less than 1 $mm^2$/particle such as, for example small alumina particles, and other inorganic particles, as it is difficult on these types of surfaces to generate therapeutic quantities of a drug aerosol with less than 10% drug degradation via vaporization.

Figure 4A:
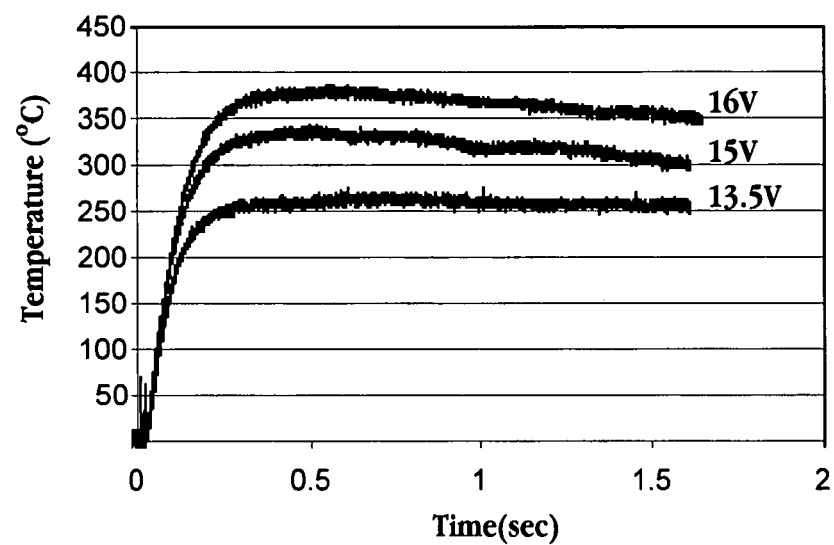

In one variation of the invention, a stainless steel foil substrate was employed. For example, stainless steel was employed for drugs tested according to Method B and was resistively heated by placing the substrate between a pair of electrodes connected to a capacitor. FIG. 4A is a plot of substrate temperature increase, measured in still air with a thin thermocouple (Omega, Model CO2-K), as a function of time, in seconds, for a stainless steel foil substrate resistively heated by charging the capacitor to 13.5 V (lower line), 15 V (middle line), and 16 V (upper line). When charged with 13.5 V, the substrate temperature increase was about 250° C. within about 200-300 milliseconds. As the capacitor voltage increased, the peak temperature of the substrate also increased. Charging the capacitor to 16V heated the foil substrate temperature about 375° C. in 200-300 milliseconds (to a maximum temperature of about 400° C.).

Figure 4B:
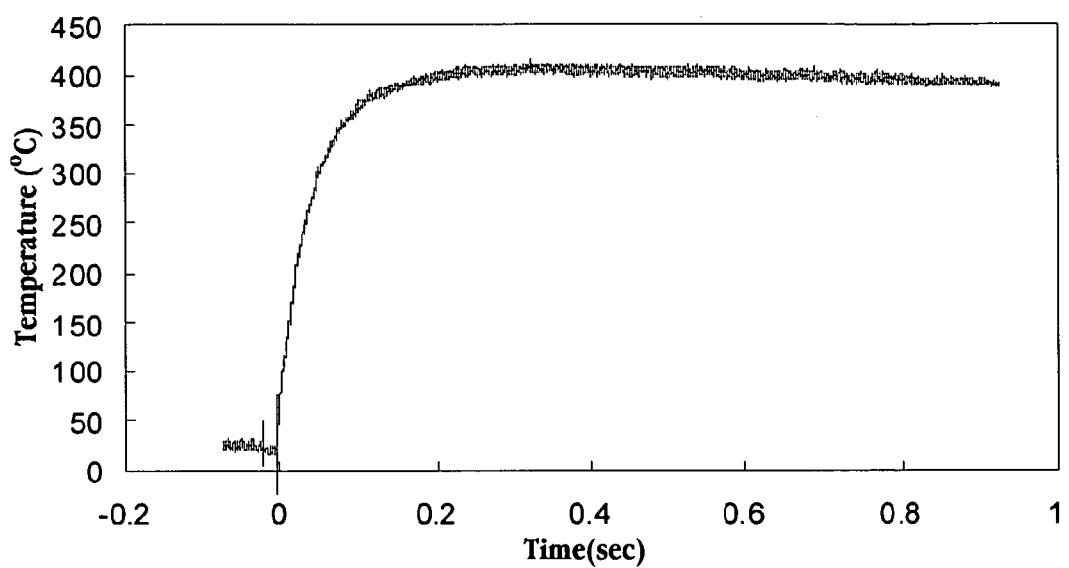

FIG. 4B shows the time-temperature relationship for a stainless steel foil substrate having a thickness of 0.005 inches. The foil substrate was heated by charging a capacitor, connected to the substrate through electrodes, to 16 V. The substrate reached its peak temperature of 400° C. in about 200 milliseconds, and maintained that temperature for the 1 second testing period.

Figure 5A:
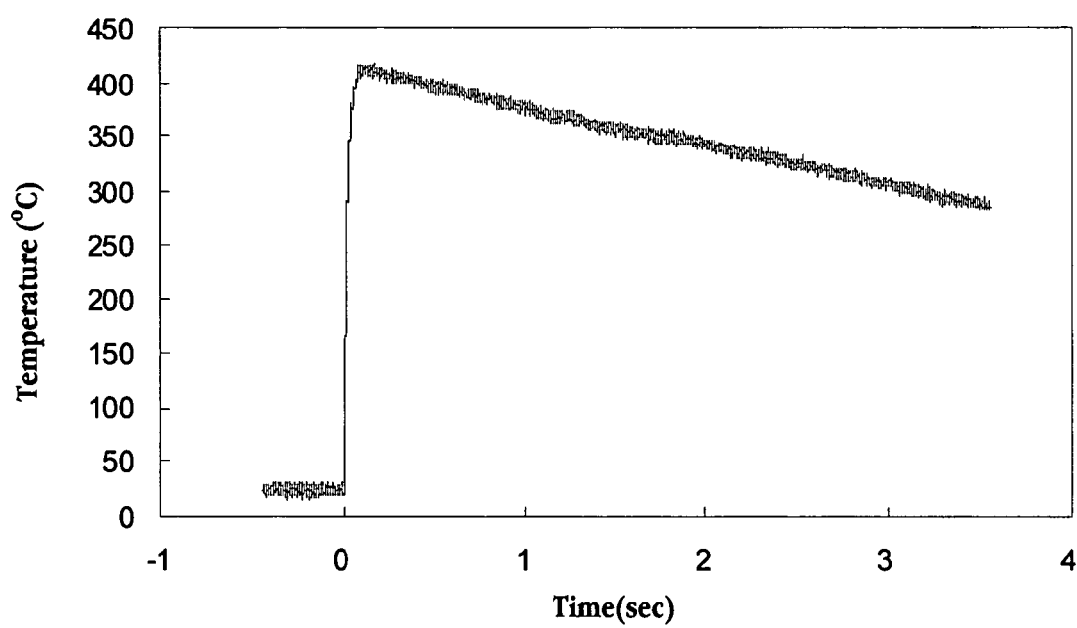
Figure 5B:
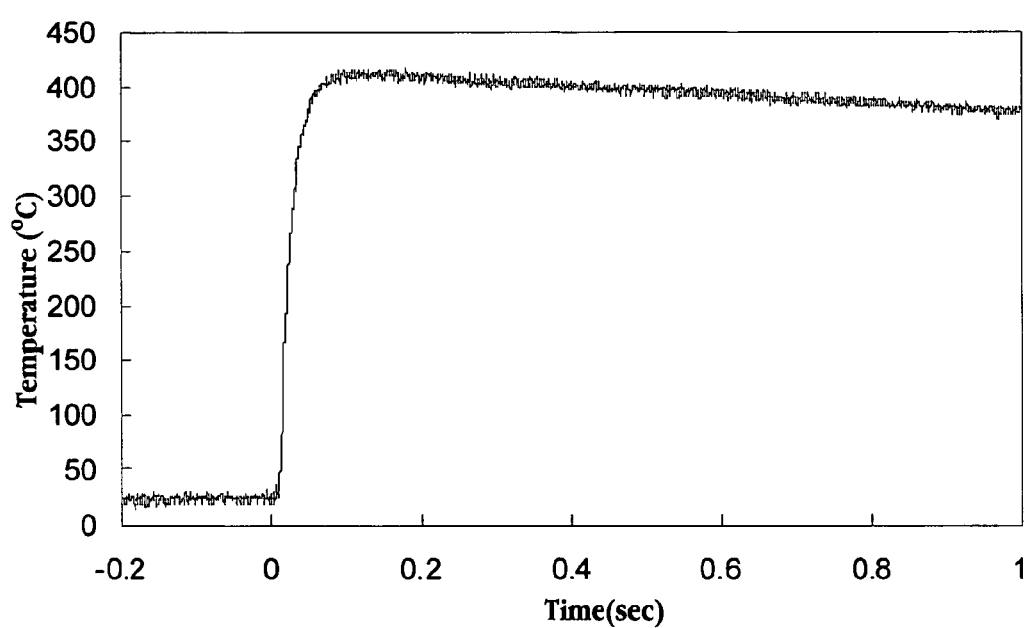

In Methods D and E, a hollow, stainless steel tube is used as the drug-film substrate. The cylindrical tube in Method D had a diameter of 13 mm and a length of 34 mm. The cylindrical tube in Method E had a diameter of 7.6 mm and a length of 51 mm. In Method D, the substrate was connected to two 1 Farad capacitors wired in parallel, whereas in Method E, the substrate was connected to two capacitors (a 1 Farad and a 0.5 Farad) wired in parallel. FIGS. 5A-5B show substrate temperature as a function of time, for the cylindrical substrate of Method D. FIG. 5B shows a detail of the first 1 second of heating.

In other variations, aluminum foil is used as a substrate for testing drug, for example, as described in Methods C, F, and G.

The composition is typically coated on the solid support in the form of a film. The film may be coated on the solid support using any suitable method. The method suitable for coating is often dependent upon the physical properties of the compound and the desired film thickness. One exemplary method of coating a composition on a solid support is by preparing a solution of compound (alone or in combination with other desirable compounds) in a suitable solvent, applying the solution to the exterior surface of the solid support, and then removing the solvent (e.g., via evaporation, etc.) thereby leaving a film on the support surface.

Common solvents include methanol, dichloromethane, methyl ethyl ketone, diethyl ether, 3:1 chloroform:methanol mixture, 1:1 dichloromethane:methyl ethyl ketone mixture, dimethylformamide, and deionized water. In some instances (e.g., when triamterene is used), it is desirable to use a solvent such as formic acid. Sonication may also be used as necessary to dissolve the compound.

The composition may also be coated on the solid support by dipping the support into a composition solution, or by spraying, brushing or otherwise applying the solution to the support. Alternatively, a melt of the drug can be prepared and applied to the support. For drugs that are liquids at room temperature, thickening agents can be mixed with the drug to permit application of a solid drug film.

The film can be of varying thickness depending on the compound and the maximum amount of thermal degradation desired. In one method, the heating of the composition involves heating a thin film of the composition having a thickness between about 0.05 µm-20 µm to form a vapor. In yet other variations, the composition has a film thickness between about 0.5 µm-10 µm. Most typically, the film thickness vaporized is between 0.5 µm-5 µm.

The support on which the film of the composition is coated can be heated by a variety of means to vaporize the composition. Exemplary methods of heating include the passage of current through an electrical resistance element, absorption of electromagnetic radiation (e.g., microwave or laser light) and exothermic chemical reactions (e.g., exothermic solvation, hydration of pyrophoric materials, and oxidation of combustible materials). Heating of the substrate by conductive heating is also suitable. One exemplary heating source is described in U.S. patent application for SELF-CONTAINED HEATING UNIT AND DRUG-SUPPLY UNIT EMPLOYING SAME, U.S. Ser. No. 60/472,697 filed May 21, 2003. The description of the exemplary heating source disclosed therein, is hereby incorporated by reference.

Heat sources typically supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. Suitable heat sources include resistive heating devices which are supplied current at a rate sufficient to achieve rapid heating, e.g., to a substrate temperature of at least 200° C., 250° C., 300° C., or 350° C. preferably within 50-500 ms, more preferably in the range of 50-200 ms. Heat sources or devices that contain a chemically reactive material which undergoes an exothermic reaction upon actuation, e.g., by a spark or heat element, such as flashbulb type heaters of the type described in several examples, and the heating source described in the above-cited U.S. patent application for SELF-CONTAINED HEATING UNIT AND DRUG-SUPPLY UNIT EMPLOYING SAME, are also suitable. In particular, heat sources that generate heat by exothermic reaction, where the chemical "load" of the source is consumed in a period of between 50-500 msec or less are generally suitable, assuming good thermal coupling between the heat source and substrate.

When heating the thin film of the composition, to avoid decomposition, it is desirable that the vaporized compound should transition rapidly from the heated surface or surrounding heated gas to a cooler environment. This may be accomplished not only by the rapid heating of the substrate, but also by the use of a flow of gas across the surface of the substrate. While a vaporized compound from a surface may transition through Brownian motion or diffusion, the temporal duration of this transition may be impacted by the extent of the region of elevated temperature at the surface, which is established by the velocity gradient of gases over the surface and the physical shape of surface. Thus decomposition can be controlled by providing a flow of gas to create a high velocity gradient (a rapid increase in velocity gradient near the surface), which results in minimization of the hot gas region above the heated surface and decreases the time of transition of the vaporized compound to a cooler environment, and/or by use of a smoother substrate surface to facilitate the transition of the hot gases from the heated surface, by precluding entrapment of the hot gases and compound vapor in, for example, depressions, pockets or pores on the surface. Typical gas-flow rates used to minimize such decomposition and to generate a desired particle size are in the range of 4-50 L/minute The aerosol particles for administration can typically be formed using any of the describe methods at a rate of greater than $10^8$ inhalable particles per second. In some variations, the aerosol particles for administration are formed at a rate of greater than $10^9$ or $10^{10}$ inhalable particles per second. Similarly, with respect to aerosol formation (i.e., the mass of aerosolized particulate matter produced by a delivery device per unit time) the aerosol may be formed at a rate greater than 0.25 mg/second, greater than 0.5 mg/second, or greater than 1 or 2 mg/second. Further, with respect to aerosol formation, focusing on the drug aerosol formation rate (i.e., the rate of drug compound released in aerosol form by a delivery device per unit time), the drug may be aerosolized at a rate greater per unit time, greater than 0.1 mg drug per second, greater than 0.5 mg drug per second, or greater than 1 or 2 mg drug per second.

In some variations, the drug condensation aerosols are formed from compositions that provide at least 5% by weight of drug condensation aerosol particles. In other variations, the aerosols are formed from compositions that provide at least 10%, 20%, 30%, 40%, 50%, 60%, or 75% by weight of drug condensation aerosol particles. In still other variations, the aerosols are formed from compositions that provide at least 95%, 99%, or 99.5% by weight of drug condensation aerosol particles.

In some variations, the drug condensation aerosol particles when formed comprise less than 10% by weight of a thermal degradation product. In other variations, the drug condensation aerosol particles when formed comprise less than 5%, 1%, 0.5%, 0.1%, or 0.03% by weight of a thermal degradation product.

In some variations the drug condensation aerosols are produced in a gas stream at a rate such that the resultant aerosols have a MMAD in the range of about 1-3 µm. In some variations the geometric standard deviation around the MMAD of the drug condensation aerosol particles is less than 3.0. In other variations, the geometric standard deviation around the MMAD of the drug condensation aerosol particles is less than 2.5, or less than 2.0.

Delivery Devices

The delivery devices described herein for administering a condensation drug aerosol typically comprise an element for heating the composition to form a vapor and an element allowing the vapor to cool, thereby forming a condensation aerosol. These aerosols are generally delivered via inhalation to lungs of a patient, for local or systemic treatment. Alternatively, however, the condensation aerosols of the invention can be produced in an air stream, for application of drug-aerosol particles to a target site. For example, a stream of air carrying drug-aerosol particles can be applied to treat an acute or chronic skin condition, can be applied during surgery at the incision site, or can be applied to an open wound. The delivery device may be combined with a composition comprising a drug in unit dose form for use as a kit.

One suitable device for inhalation is illustrated in FIG. 27. Delivery device 100 has a proximal end 102 and a distal end 104, a solid support 106, a power source 108, and a mouthpiece 110. In this depiction, solid support 106 also comprises a heating module. A composition is deposited on solid support 106. Upon activation of a user activated switch 114, power source 108 initiates heating of heating module (e.g., through ignition of combustible fuel or passage of current through a resistive heating element, etc.).

The composition vaporizes and condenses to form a condensation aerosol prior to reaching the mouthpiece 110 at the proximal end of the device 102. Air flow traveling from the device distal end 104 to the mouthpiece 110 carries the condensation aerosol to the mouthpiece 110, where it is inhaled by a user.

The devices described herein may additionally contain a variety of components to facilitate aerosol delivery. For instance, the device may include any component known in the art to control the timing of drug aerosolization relative to inhalation (e.g., breath-actuation). Similarly, the device may include a component to provide feedback to patients on the rate and/or volume of inhalation, or a component to prevent excessive use (i.e., "lockout" feature). In addition, the device may further include a component to prevent use by unauthorized individuals, and a component to record dosing histories. These components may be used alone, or in combination with other components.

The element that allows cooling may be of any configuration. For example, it may be an inert passageway linking the heating means to the inhalation means. Similarly, the element permitting inhalation by a user may be of any configuration. For example, it may be an exit portal that forms a connection between the cooling element and the user's respiratory system.

Figure 2A:
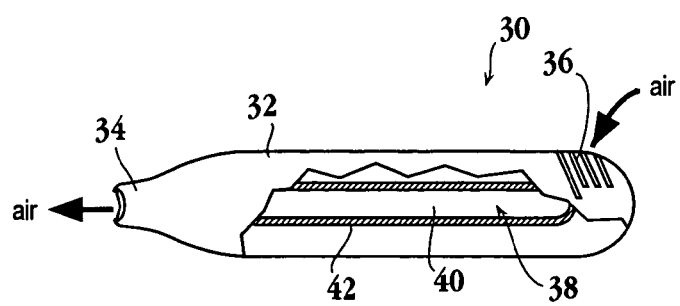

Other suitable devices for use with the aerosols described herein are shown in FIGS. 2A and 2B. As shown in FIG. 2A, there is a device 30 comprising an element for heating a composition to form a vapor, an element allowing the vapor to cool, thereby forming a condensation aerosol, and an element permitting a user to inhale the aerosol. Device 30 also comprises a housing 32 with a tapered end 34 for insertion into the mouth of a user. On the end opposite tapered end 34, the housing has one or more openings, such as slots 36, for air intake when a user places the device in the mouth and inhales a breath. Within housing 32 is a drug supply article 38, visible in the cut-away portion of the figure. Drug supply article 38 includes a substrate 40 coated on its external surface with a film 42 of a therapeutic drug to be delivered to the user.

Typically, the drug supply article 38 is heated to a temperature sufficient to vaporize all or a portion of the film 42, so that the composition forms a vapor that becomes entrained in a stream of air during inhalation. As noted above, heating of the drug supply article 38 may be accomplished using, for example, an electrically-resistive wire embedded or inserted into the substrate and connected to a battery disposed in the housing. The heating can be actuated, for example, with a button on the housing or via breath actuation, as is known in the art.

FIG. 2B shows another device that may be used to form and deliver the aerosols described herein. The device, 50 comprises an element for heating a composition to form a vapor, an element allowing the vapor to cool, thereby forming a condensation aerosol, and an element permitting a user to inhale the aerosol. The device also comprises an upper external housing member 52 and a lower external housing member 54 that fit together.

Shown in the depiction of FIG. 2B, the downstream end of each housing member is gently tapered for insertion into a user's mouth, as best seen on upper housing member 52 at downstream end 56. The upstream end of the upper and lower housing members are slotted, as seen best in the figure in the upper housing member at 58, to provide for air intake when a user inhales. The upper and lower housing members when fitted together define a chamber 60. Positioned within chamber 60 is a drug supply unit 62, shown in a partial cut-away view.

As shown in FIG. 2B, the drug supply unit has a tapered substantially cylindrical substrate 64. However, as described above the solid support may be of any desirable configuration. At least a portion of the surface 68 of the substrate 64 is coated with a composition film 66. Visible in the cut-away portion of the drug-supply unit is an interior region 70 of the substrate containing a substance suitable to generate heat. The substance can be a solid chemical fuel, chemical reagents that mix exothermically, electrically resistive wire, etc. A power supply source, if needed for heating, and any necessary valving for the inhalation device may be contained in end piece 72. In one variation of the devices used, the device includes a drug composition delivery article composed of the substrate, a film of the selected drug composition on the substrate surface, and a heat source for supplying heat to the substrate at a rate effective to heat the substrate to a temperature greater than 200° C. or in other embodiments to a temperature greater than 250° C., 300° C. or 350° C., and to produce substantially complete volatilization of the drug composition within a period of 2 seconds or less.

Figure 1A:
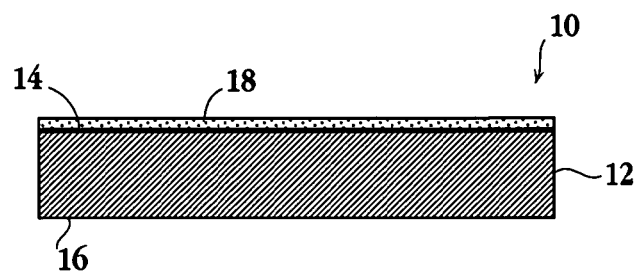
Figure 1B:
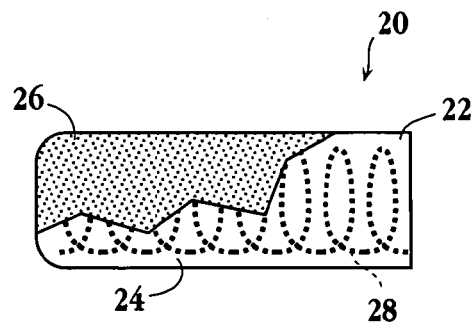

FIGS. 1A and 1B provide exploded views of other drug supply articles that may be used in combination with the devices described herein. As shown in FIG. 1A, there is a drug supply article comprising a heat conducting substrate 10 having a composition coating 18 at least a portion of the upper surface 14. While the coating 18 is shown on upper surface 14 in FIG. 1A, it should be understood that it need not be so. Indeed, the coating may be placed on any suitable surface, such as surfaces 16 and 12. Various methods of coatings are known in the art and/or have been described above.

FIG. 1B provides a perspective, cut-away view of another drug supply article 20 that may be used with the methods and devices herein described. As shown there, the article 20 comprises a cylinder-shaped substrate 22. This substrate may be formed from a heat-conductive material, for example. The exterior surface 24 of substrate 22 is coated with a composition 26. As shown in the cut-away portion, there is a heating element 28 disposed in the substrate. The substrate can be hollow with a heating element inserted into the hollow space or solid with a heating element incorporated into the substrate.

The illustrative heating element shown in FIG. 1B is shown as an electrical resistive wire that produces heat when a current flows through it, but as noted above, a number of different heating methods and corresponding devices are acceptable. For example, acceptable heat sources can supply heat to the drug supply article at rates that rapidly achieve a temperature sufficient to completely vaporize the composition from the support surface. For example, heat sources that achieve a temperature of 200° C. to 500° C. or more within a period of 2 seconds are typical, although it should be appreciated that the temperature chosen will be dependent upon the vaporization properties of the composition, but is typically heated to a temperature of at least about 200° C., preferably of at least about 250° C., more preferably at least about 300° C. or 350° C. Heating the substrate produces a drug composition vapor that in the presence of the flowing gas generates aerosol particles in the desired size range. The presence of the gas flow is generally prior to, simultaneous with, or subsequent to heating the substrate. In one embodiment, the substrate is heated for a period of less than about 1 second, and more preferably for less than about 500 milliseconds, still more preferably for less than about 200 milliseconds. The drug-aerosol particles are inhaled by a subject for delivery to the lung.

FIGS. 3A-3E are high speed photographs showing the generation of aerosol particles from a drug-supply unit. FIG. 3A shows a heat-conductive substrate about 2 cm in length coated with a film of drug. The drug-coated substrate was placed in a chamber through which a stream of air was flowing in an upstream-to-downstream direction (from left to right in FIG. 3) at rate of about 15 L/min. The substrate was electrically heated and the progression of drug vaporization monitored by real-time photography. FIGS. 3B-3E show the sequence of drug vaporization and aerosol generation at time intervals of 50 milliseconds (msec), 100 msec, 200 msec, and 500 msec, respectively. The white cloud of drug-aerosol particles formed from the drug vapor entrained in the flowing air is visible in the photographs. Complete vaporization of the drug film was achieved by 500 msec.

The device may also include a gas-flow control valve disposed upstream of the solid support, for limiting gas-flow rate through the condensation region. The gas-flow valve may, for example, include an inlet port communicating with the chamber, and a deformable flap adapted to divert or restrict airflow away from the port increasingly, with increasing pressure drop across the valve. Similarly, the gas-flow valve may include an actuation switch. In this variation, the valve movement would be in response to an air pressure differential across the valve, which for example, could function to close the switch. The gas-flow valve may also include an orifice designed to limit airflow rate into the chamber.

The device may also include a bypass valve communicating with the chamber downstream of the unit for offsetting the decrease in airflow produced by the gas-flow control valve, as the user draws air into the chamber. In this way, the bypass valve could cooperate with the gas-control valve to control the flow through the condensation region of the chamber as well as the total amount of air being drawn through the device. Thus the total volumetric airflow through the device in this variation would be the sum of the volumetric airflow rate through the gas-control valve and the volumetric airflow rate through the bypass valve.

The gas control valve could, for example, function to limit air drawn into the device to a preselected level, e.g., 15 L/minute. In this way, airflow for producing particles of a desired size may be preselected and produced. For example, once this selected airflow level is reached, additional air drawn into the device would create a pressure drop across the bypass valve, which in turn would accommodate airflow through the bypass valve into the downstream end of the device adjacent the user's mouth. Thus, the user senses a full breath being drawn in, with the two valves distributing the total airflow between desired airflow rate and bypass airflow rate.

These valves may be used to control the gas velocity through the condensation region of the chamber and hence to control the particle size of the aerosol particles produced. Typically, the faster the airflow, the smaller the particles are. Thus, to achieve smaller or larger particles, the gas velocity through the condensation region of the chamber may be altered by modifying the gas-flow control valve to increase or decrease the volumetric airflow rate. For example, to produce condensation particles in the size range of about 1-3.5 μm MMAD, a chamber having substantially smooth-surfaced walls would have a selected gas-flow rate in the range of 4-50 L/minute.

Additionally, as will be appreciated by one of skill in the art, particle size may be altered by modifying the cross-section of the chamber condensation region to increase or decrease linear gas velocity for a given volumetric flow rate, and/or the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface. Particle size is discussed in more detail below. Additionally, the drug supply units disclosed herein can also be used to generate a drug vapor that can readily be mixed with gas to produce an aerosol for topical delivery, typically by a spray nozzle, to a topical site for a variety of treatment regimens, including acute or chronic treatment of a skin condition, administration of a drug to an incision site during surgery or to an open wound. Rapid vaporization of the drug film occurs with minimal thermal decomposition of the drug.

Drug Composition Film Thickness

Typically, the drug composition film coated on the solid support has a thickness of between about 0.05-20 μm, and typically a thickness between 0.1-15 μm. More typically, the thickness is between about 0.2-10 μm; even more typically, the thickness is between about 0.5-10 μm, and most typically, the thickness is between about 0.5-5 μm. The desirable film thickness for any given drug composition is typically determined by an iterative process in which the desired yield and purity of the condensation aerosol composition are selected or known.

For example, if the purity of the particles is less than that which is desired, or if the percent yield is less than that which is desired, the thickness of the drug film is adjusted to a thickness different from the initial film thickness. The purity and yield are then determined at the adjusted film thickness, and this process is repeated until the desired purity and yield are achieved. After selection of an appropriate film thickness, the area of substrate required to provide a therapeutically effective dose is determined. Generally, the film thickness for a given drug composition is such that drug-aerosol particles, formed by vaporizing the drug composition by heating the substrate and entraining the vapor in a gas stream, have (i) 10% by weight or less drug-degradation product, more preferably 5% by weight or less, most preferably 2.5% by weight or less and (ii) at least 50% of the total amount of drug composition contained in the film. The area of the substrate on which the drug composition film is formed is selected to achieve an effective human therapeutic dose of the drug aerosol as is described further below. Examples of how film thickness affects purity were conducted in support of the invention and are described below. A variety of drugs were deposited on a heat-conductive, impermeable substrate and the substrate was heated to a temperature sufficient to generate a thermal vapor. Purity of drug-aerosol particles in the thermal vapor was determined by a suitable analytical method. Three different substrate materials were used in the studies: stainless steel foil, aluminum foil, and a stainless steel cylinder. Methods B-G below detail the procedures for forming a drug film on each substrate and the method of heating each substrate.

In Examples 1-236 below, a substrate containing a drug film of a certain thickness was prepared. To determine the thickness of the drug film, one method that can be used is to determine the area of the substrate and calculate drug film thickness using the following relationship:

$$\text{film thickness (cm)} = \text{drug mass (g)} / [\text{drug density (g/cm}^3) \times \text{substrate area (cm}^2)]$$

The drug mass can be determined by weighing the substrate before and after formation of the drug film or by extracting the drug and measuring the amount analytically. Drug density can be experimentally determined by a variety of techniques, known by those of skill in the art or found in the literature or in reference texts, such as in the CRC. An assumption of unit density is acceptable if an actual drug density is not known.

Figures 6, 7:
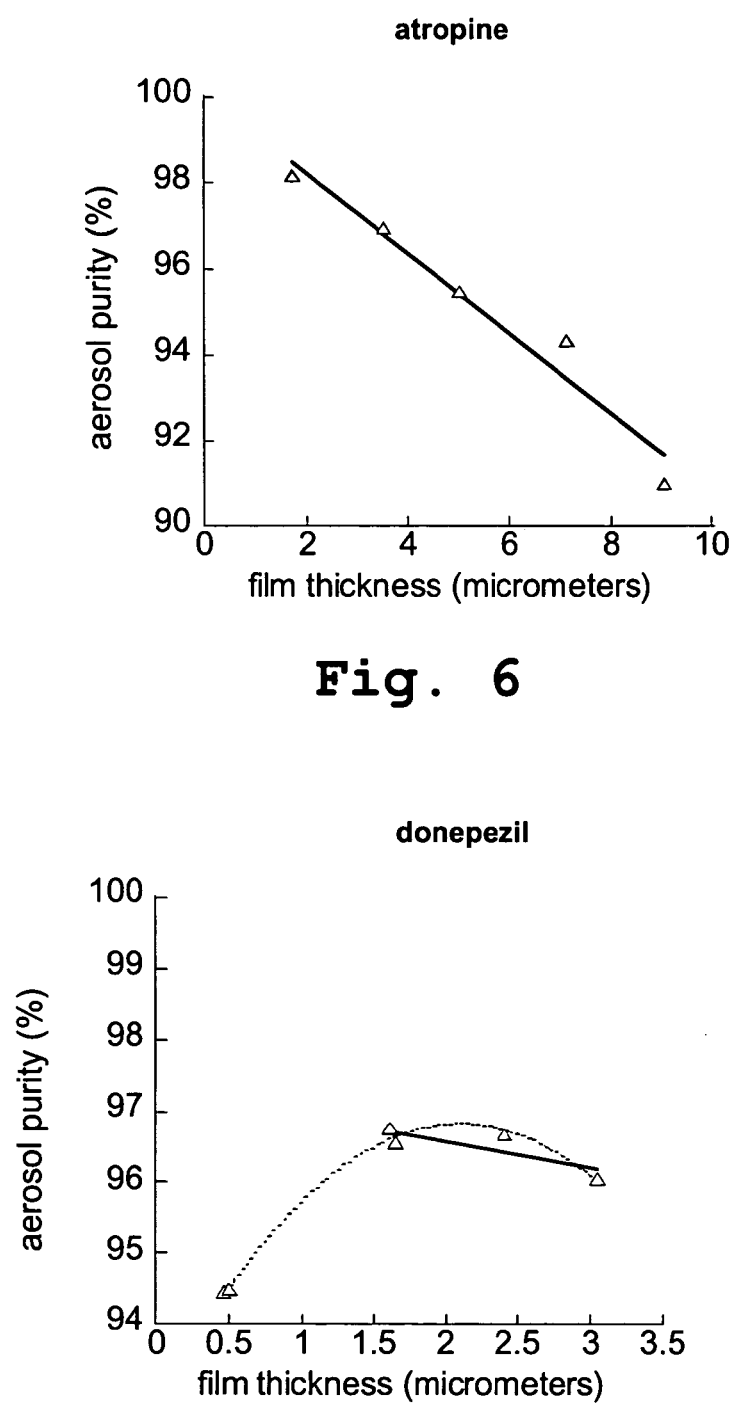

In the studies reported in the Examples, the substrate having a drug film of known thickness was heated to a temperature sufficient to generate a thermal vapor. All or a portion of the thermal vapor was recovered and analyzed for presence of drug-degradation products, to determine purity of the aerosol particles in the thermal vapor. Several drugs are discussed here as merely exemplary of the studies reported in Examples 1-236. Example 10 describes preparation of a drug-supply article containing atropine, a muscarinic antagonist. Substrates containing films of atropine ranging in thickness from between about 1.7 µm to about 9.0 µm were prepared. The stainless steel substrates were heated and the purity of the drug-aerosol particles in the thermal vapor generated from each substrate was determined. FIG. 6 shows the results, where drug aerosol purity as a function of drug film thickness is plotted. There is a clear relationship between film thickness and aerosol particle purity, where as the film thickness decreases, the purity increases. An atropine film having a thickness of 9.0 µm produced a thermal vapor having a purity of 91%; an atropine film having a thickness of 1.7 µm produced a thermal vapor having a purity of 98%.

Hydromorphone, an analgesic, was also tested, as described in Example 66. Substrates having a drug film thickness of between about 0.7 µm to about 2.7 µm were prepared and heated to generate a thermal vapor. Purity of the aerosol particles improved as the thickness of the drug film on the substrate decreased.

Figures 22, 23:
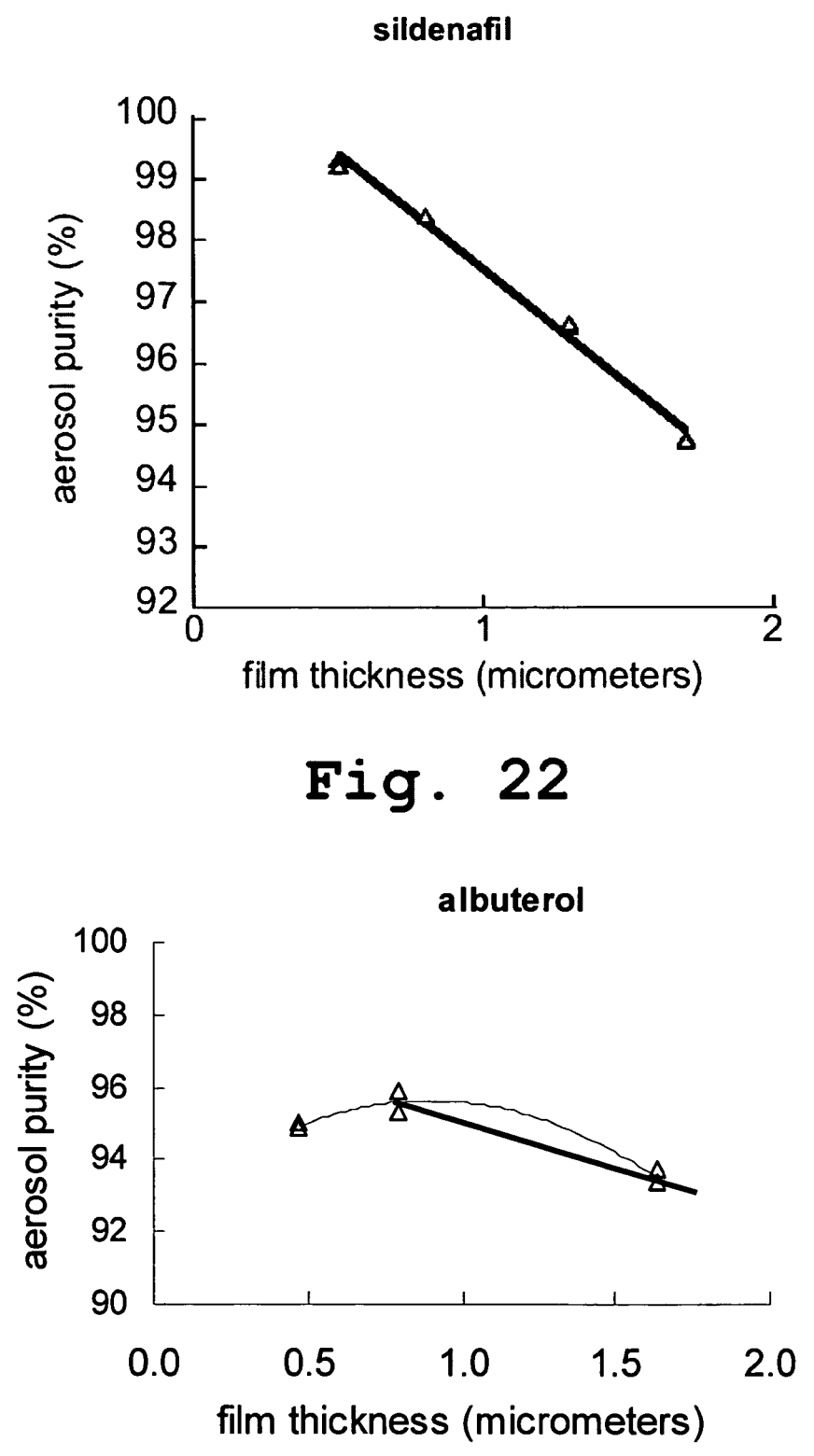

FIG. 7 shows the relationship between drug film thickness and aerosol-purity for donepezil. As described in Example 44, donepezil was coated onto foil substrates to film thicknesses ranging from about 0.5 µm to about 3.2 µm. Purity of the aerosol particles from each of the films on the substrates was analyzed. At drug film thicknesses of 1.5 µm to 3.2 µm, purity of the aerosol particles improved as thickness of the drug film on the substrate decreased, similar to the trend found for atropine and hydromorphone. In contrast, at less than 1.5 µm thickness, purity of the aerosol particles worsened as thickness of the drug film on the substrate decreased. A similar pattern was also observed for albuterol, as described in Example 3, with aerosol particles purity peaking for films of approximately 1 µm, and decreasing for both thinner and thicker films as shown in FIG. 23.

FIGS. 9-23 present data for aerosol purity as a function of film thickness for the following compounds: buprenorphine (Example 16), clomipramine (Example 28), ciclesonide (Example 26), midazolam (Example 100), nalbuphine (Example 103), naratriptan (Example 106), olanzapine (Example 109), quetiapine (Example 127), tadalafil (Example 140), prochlorperazine (Example 122), zolpidem (Example 163), fentanyl (Example 57), alprazolam (Example 4), sildenafil (Example 134), and albuterol (Example 3).

In FIGS. 6-23, the general relationship between increasing aerosol purity with decreasing film thickness is apparent; however the extent to which aerosol purity varies with a change in film thickness varies for each drug composition. For example, aerosol purity of sildenafil (FIG. 22) exhibited a strong dependence on film thickness, where films about 0.5 µm in thickness had a purity of greater than 99% and films of about 1.6 µm in thickness had a purity of between 94-95%. In contrast, for midazolam (FIG. 12), increasing the film thickness from approximately 1.2 µm to approximately 5.8 µm resulted in a decrease in aerosol particle purity from greater than 99.9% to approximately 99.5%, a smaller change in particle purity despite a larger increase in film thickness compared with the sildenafil example. Moreover, as was discussed above, the inverse relationship between film thickness and purity of aerosolized drug observed for many compounds in the thickness range less than about 20 µm does not necessarily apply at the thinnest film thicknesses that were tested. Some compounds, such as illustrated by donepezil (FIG. 7) show a rather pronounced decrease in purity at film thicknesses both below and above an optimal film thickness, in this case, above and below about 2 µm film thicknesses.

One way to express the dependence of aerosol purity on film thickness is by the slope of the line from a plot of aerosol purity against film thickness. For compounds such as donepezil (FIG. 7), the slope of the line is taken from the maximum point in the curve towards the higher film thickness. Table 1, discussed below, shows the slope of the line for the curves shown in FIGS. 6-23. Particularly preferred compounds for delivery by the various embodiments of the present invention are compounds with a substantial (i.e., highly negative) slope of the line on the aerosol purity versus thickness plot, e.g., a slope more negative than −0.1% purity per micron and more preferably −0.5% purity per micron.

In addition to selection of a drug film thickness that provides aerosol particles containing 10% or less drug-degradation product (i.e., an aerosol particle purity of 90% or more), the film thickness is selected such that at least about 50% of the total amount of drug composition contained in the film is vaporized when the substrate is heated to a temperature sufficient to vaporize the film. In the studies described herein, the percentage of drug film vaporized was determined by quantifying (primarily by HPLC or weight) the mass of drug composition collected upon vaporization or alternatively by the amount of substrate mass decrease. The mass of drug composition collected after vaporization and condensation was compared with the starting mass of the drug composition film that was determined prior to vaporization to determine a percent yield, also referred to herein as a percent emitted. This value is indicated in many of the Examples set forth below. For example, in Example 1 a film having a thickness of 1.1 µm was formed from the drug acebutolol, a beta-adrenergic blocking agent. The mass coated on the substrate was 0.89 mg and the mass of drug collected in the thermal vapor was 0.53 mg, to give a 59.6 percent yield. After vaporization, the substrate and the testing chamber were washed to recover any remaining drug. The total drug recovered from the test apparatus, including the emitted thermal vapor, was 0.81 mg, to give a 91% total recovery. In another example, midazolam was coated onto an impermeable substrate, as described in Example 100. A drug film having a thickness of 9 µm was formed. Heating of the substrate generated a thermal vapor containing drug aerosol particles having a purity of 99.5%. The fraction of drug film collected on the filter, i.e., the percent yield, was 57.9%. After vaporization, the substrate and the testing chamber were washed to recover any remaining drug. The total drug recovered from the test apparatus and the filter was 5.06 mg, to give a 94.2% total recovery.

In the examples, the following drugs were vaporized and condensed to generate condensation aerosol having a purity of 90% or greater: acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenyloin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocamide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, and triamcinolone acetonide.

Of these compounds, the following drugs were vaporized from thin films and formed condensation aerosols having greater than 95% purity: acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenyloin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocamide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, and temazepam.

Drugs, exemplified in the Examples below, which formed condensation aerosols from a thin film having a purity of 98% or greater were the following: acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenyloin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocamide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, and zonisamide.

To obtain higher purity aerosols one can coat a lesser amount of drug, yielding a thinner film to heat, or alternatively use the same amount of drug but a larger surface area. Generally, except for, as discussed above, extremely thin thickness of drug film, a linear decrease in film thickness is associated with a linear decrease in impurities. Thus for the drug composition where the aerosol exhibits an increasing level of drug degradation products with increasing film thicknesses, particularly at a thickness of greater than 0.05-20 microns, the film thickness on the substrate will typically be between 0.05 and 20 microns, e.g., the maximum or near-maximum thickness within this range that allows formation of a particle aerosol with drug degradation less than 5%. Other drugs may show less than 5-10% degradation even at film thicknesses greater than 20 microns. For these compounds, a film thickness greater than 20 microns, e.g., 20-50 microns, may be selected, particularly where a relatively large drug dose is desired. In addition, to adjusting film thickness other modifications can be made to improve the purity or yield of the aerosol generated. One such method involves the use of an altered form of the drug, such as, for example but not limitation, use of a prodrug, or a free base, free acid or salt form of the drug. As demonstrated in various Examples below, modifying the form of the drug can impact the purity and or yield of the aerosol obtained. Although not always the case, the free base or free acid form of the drug as opposed to the salt, generally results in either a higher purity or yield of the resultant aerosol. Thus, in a preferred embodiment of the invention, the free base and free acid forms of the drugs are used.

Another approach contemplates generation of drug-aerosol particles having a desired level of drug composition purity by forming the thermal vapor under a controlled atmosphere of an inert gas, such as argon, nitrogen, helium, and the like. Various Examples below show that a change in purity can be observed upon changing the gas under which vaporization occurs.

Examples 166-233 correspond to studies conducted on drugs that when deposited as a thin film on a substrate produced a thermal vapor having a drug purity of less than about 90% but greater than about 60% or where the percent yield was less than about 50%. Purity of the thermal vapor of many of these drugs would be improved by using one or more of the approaches discussed above.

Once a desired purity and yield have been achieved or can be estimated from a graph of aerosol purity versus film thickness and the corresponding film thickness determined, the area of substrate required to provide a therapeutically effective dose is determined Substrate Area As noted above, the surface area of the substrate surface area is selected such that it is sufficient to yield a therapeutically effective dose. The amount of drug to provide a therapeutic dose is generally known in the art and is discussed more below. The required dosage and selected film thickness, discussed above, dictate the minimum required substrate area in accord with the following relationship:

$$\text{film thickness (cm)} \times \text{drug density (g/cm}^3\text{)} \times \text{substrate area (cm}^2\text{)} = \text{dose (g)}$$

OR $$\text{Substrate area (cm}^2\text{)} = \text{dose (g)} / [\text{film thickness (cm)} \times \text{drug density (g/cm}^3\text{)}]$$

The drug mass can be determined by weighing the substrate before and after formation of the drug film or by extracting the drug and measuring the amount analytically. Drug density can be determined experimentally by a variety of well known techniques, or may be found in the literature or in reference texts, such as in the CRC. An assumption of unit density is acceptable if an actual drug density is not known.

To prepare a drug supply article comprised of a drug film on a heat-conductive substrate that is capable of administering an effective human therapeutic dose, the minimum substrate surface area is determined using the relationships described above to determine a substrate area for a selected film thickness that will yield a therapeutic dose of drug aerosol. Table 1 shows a calculated substrate surface area for a variety of drugs on which an aerosol purity-film thickness profile was constructed.

TABLE 1

| Drug | Typical Dose (mg) | Preferred Film Thickness (μm) | Calculated Substrate Surface Area (cm²) | Slope of Line on aerosol purity vs. thickness plot (% purity/micron) |
|---|---|---|---|---|
| Albuterol | 0.2 | 0.1-10 | 0.2-20 | −0.64 (FIG. 23) |
| Alprazolam | 0.25 | 0.1-10 | 0.25-25 | −0.44 (FIG. 21) |
| Amoxapine | 25 | 2-20 | 12.5-125 | |
| Atropine | 0.4 | 0.1-10 | 0.4-40 | −0.93 (FIG. 6) |
| Bumetanide | 0.5 | 0.1-5 | 1-50 | |
| Buprenorphine | 0.3 | 0.05-10 | 0.3-60 | −0.63 (FIG. 9) |
| Butorphanol | 1 | 0.1-10 | 1-100 | |
| Clomipramine | 50 | 1-8 | 62-500 | −1.0 (FIG. 10) |
| Donepezil | 5 | 1-10 | 5-50 | −0.38 (FIG. 7) |
| Hydromorphone | 2 | 0.05-10 | 2-400 | −0.55 (FIG. 8) |
| Loxapine | 10 | 1-20 | 5-100 | |
| Midazolam | 1 | 0.05-20 | 0.5-200 | −0.083 (FIG. 12) |
| Morphine | 5 | 0.2-10 | 5-250 | |
| Nalbuphine | 5 | 0.2-5 | 10-250 | −1.12 (FIG. 13) |
| Naratriptan | 1 | 0.2-5 | 2-50 | −1.42 (FIG. 14) |
| Olanzapine | 10 | 1-20 | 5-100 | −0.16 (FIG. 15) |
| Paroxetine | 20 | 1-20 | 10-200 | |
| Prochlorperazine | 5 | 0.1-20 | 2.5-500 | −0.11 (FIG. 18) |
| Quetiapine | 50 | 1-20 | 25-500 | −0.18 (FIG. 16) |
| Rizatriptan | 3 | 0.2-20 | 1.5-150 | |
| Sertraline | 25 | 1-20 | 12.5-250 | |
| Sibutramine | 10 | 0.5-2 | 50-200 | |

TABLE 1-continued

| Drug | Typical Dose (mg) | Preferred Film Thickness (μm) | Calculated Substrate Surface Area (cm$^2$) | Slope of Line on aerosol purity vs. thickness plot (% purity/micron) |
|---|---|---|---|---|
| Sildenafil | 6 | 0.2-3 | 20-300 | −3.76 (FIG. 22) |
| Sumatriptan | 3 | 0.2-6 | 5-150 | |
| Tadalafil | 3 | 0.2-5 | 6-150 | −1.52 (FIG. 17) |
| Testosterone | 3 | 0.2-20 | 1.5-150 | |
| Vardenafil | 3 | 0.1-2 | 15-300 | |
| Venlafaxine | 50 | 2-20 | 25-250 | |
| Zolpidem | 5 | 0.1-10 | 5-500 | −0.88 (FIG. 19) |
| Apomorphine HCl | 2 | 0.1-5 | 4-200 | |
| Celecoxib | 50 | 2-20 | 25-250 | |
| Ciclesonide | 0.2 | 0.05-5 | 0.4-40 | −1.70 (FIG. 11) |
| Fentanyl | 0.05 | 0.05-5 | 0.1-10 | |
| Eletriptan | 3 | 0.2-20 | 1.5-150 | |
| Parecoxib | 10 | 0.5-2 | 50-200 | |
| Valdecoxib | 10 | 0.5-10 | 10-200 | |

In some variations, the selected substrate surface area is between about 0.05-500 cm$^2$. In others, the surface area is between about 0.05 and 300 cm$^2$. Typically the surface area is between 0.5 and 250 cm$^2$. Particularly, preferred substrate surface areas, are between 0.5 and 100 cm$^2$.

The actual dose of drug delivered, i.e., the percent yield or percent emitted, from the drug-supply article will depend on, along with other factors, the percent of drug film that is vaporized upon heating the substrate. Thus, for drug films that yield upon heating 100% of the drug film and aerosol particles that have a 100% drug purity, the relationship between dose, thickness, and area given above correlates directly to the dose provided to the user. As the percent yield and/or particle purity decrease, adjustments in the substrate area can be made as needed to provide the desired dose. Also, as one of skill in the art will recognize, larger substrate areas other than the minimum calculated area for a particular film thickness can be used to deliver a therapeutically effective dose of the drug. Moreover as can be appreciated by one of skill in art, the film need not coat the complete surface area if a selected surface area exceeds the minimum required for delivering a therapeutic dose from a selected film thickness.

Dosage of Drug Containing Aerosols

The dose of a drug compound or compounds in aerosol form is generally no greater than twice the standard dose of the drug given orally. Typically, it will be equal to or less than 100% of the standard oral dose. Preferably, it will be less than 80%, and more preferably less than 40%, and most preferably less than 20% of the standard oral dose. For medications currently given intravenously, the drug dose in the aerosol will generally be similar to or less than the standard intravenous dose. Preferably it will be less than 200%, more preferably less than 100%, and most preferably less than 50% of the standard intravenous dose. Oral and/or intravenous doses for most drugs are readily available in the Physicians Desk Reference.

A dosage of a drug-containing aerosol may be administered in a single inhalation or may be administered in more than one inhalation, such as a series of inhalations. Where the drug is administered as a series of inhalations, the inhalations are typically taken within an hour or less (dosage equals sum of inhaled amounts). When the drug is administered as a series of inhalations, a different amount may be delivered in each inhalation.

The dose of a drug delivered in the aerosol refers to a unit dose amount that is generated by heating of the drug under defined conditions, cooling the ensuing vapor, and delivering the resultant aerosol. A "unit dose amount" is the total amount of drug in a given volume of inhaled aerosol. The unit dose amount may be determined by collecting the aerosol and analyzing its composition as described herein, and comparing the results of analysis of the aerosol to those of a series of reference standards containing known amounts of the drug. The amount of drug or drugs required in the starting composition for delivery as a aerosol depends on the amount of drug or drugs entering the thermal vapor phase when heated (i.e., the dose produced by the starting drug or drugs), the bioavailability of the aerosol drug or drugs, the volume of patient inhalation, and the potency of the aerosol drug or drugs as a function of plasma drug concentration.

One can determine the appropriate dose of a drug-containing aerosol to treat a particular condition using methods such as animal experiments and a dose-finding (Phase I/II) clinical trial. These experiments may also be used to evaluate possible pulmonary toxicity of the aerosol. One animal experiment involves measuring plasma concentrations of drug in an animal after its exposure to the aerosol. Mammals such as dogs or primates are typically used in such studies, since their respiratory systems are similar to that of a human and they typically provide accurate extrapolation of test results to humans. Initial dose levels for testing in humans are generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered. The actual effective amount of drug for a particular patient can vary according to the specific drug or combination thereof being utilized, the particular composition formulated, the mode of administration and the age, weight, and condition of the patient and severity of the episode being treated.

Particle Size

Efficient aerosol delivery to the lungs requires that the particles have certain penetration and settling or diffusional characteristics. Deposition in the deep lungs occurs by gravitational settling and requires particles to have an effective settling size, defined as mass median aerodynamic diameter (MMAD), typically between 1-3.5 μm. For smaller particles, deposition to the deep lung occurs by a diffusional process that requires having a particle size in the 10-100 nm, typically 20-100 nm range. Particle sizes in the range between 0.1-1.0 μm, however, are generally too small to settle onto the lung wall and too massive to diffuse to the wall in a timely manner. These types of particles are typically removed from the lung by exhalation, and thus are generally not used to treat disease. Therefore, an inhalation drug-delivery device for deep lung delivery should produce an aerosol having particles in one of these two size ranges, preferably between about 1-3 μm MMAD. Typically, in order to produce particles having a desired MMAD, gas or air is passed over the solid support at a certain flow rate.

During the condensation stage the MMAD of the aerosol is increasing over time. Typically, in variations of the invention, the MMAD increases within the size range of 0.01-3 microns as the vapor condenses as it cools by contact with the carrier gas then further increases as the aerosol particles collide with each other and coagulate into larger particles. Most typically, the MMAD grows from <0.5 micron to >1 micron in less than 1 second. Thus typically, immediately after condensing into particles, the condensation aerosol MMAD doubles at least once per second, often at least 2, 4, 8, or 20 times per second. In other variations, the MMAD increases within the size range of 0.1-3 microns.

Typically, the higher the flow rate, the smaller the particles that are formed. Therefore, in order to achieve smaller or larger particles, the flow rate through the condensation region of the delivery device may be altered. A desired particle size is achieved by mixing a compound in its vapor-state into a volume of a carrier gas, in a ratio such that the desired particle size is achieved when the number concentration of the mixture reaches approximately $10^9$ particles/mL. The particle growth at this number concentration is then slow enough to consider the particle size to be "stable" in the context of a single deep inhalation. This may be done, for example, by modifying a gas-flow control valve to increase or decrease the volumetric airflow rate. To illustrate, condensation particles in the size range 1-3.5 μm MMAD may be produced by selecting the gas-flow rate to be in a range of 4-50 L/minute, preferably in the range of 5-30 L/min.

Additionally, as will be appreciated by one of skill in the art, particle size may also be altered by modifying the cross-section of the chamber condensation region to increase or decrease linear gas velocity for a given volumetric flow rate. In addition, particle size may also be altered by the presence or absence of structures that produce turbulence within the chamber. Thus, for example to produce condensation particles in the size range 10-100 nm MMAD, the chamber may provide gas-flow barriers for creating air turbulence within the condensation chamber. These barriers are typically placed within a few thousandths of an inch from the substrate surface.

Analysis of Drug Containing Aerosols

Purity of a drug-containing aerosol may be determined using a number of different methods. It should be noted that when the term "purity" is used, it refers to the percentage of aerosol minus the percent byproduct produced in its formation. Byproducts for example, are those unwanted products produced during vaporization. For example, byproducts include thermal degradation products as well as any unwanted metabolites of the active compound or compounds. Examples of suitable methods for determining aerosol purity are described in Sekine et al., *Journal of Forensic Science* 32:1271-1280 (1987) and in Martin et al., *Journal of Analytic Toxicology* 13:158-162 (1989).

One suitable method involves the use of a trap. In this method, the aerosol is collected in a trap in order to determine the percent or fraction of byproduct. Any suitable trap may be used. Suitable traps include filters, glass wool, impingers, solvent traps, cold traps, and the like. Filters are often most desirable. The trap is then typically extracted with a solvent, e.g. acetonitrile, and the extract subjected to analysis by any of a variety of analytical methods known in the art, for example, gas, liquid, and high performance liquid chromatography particularly useful.

The gas or liquid chromatography method typically includes a detector system, such as a mass spectrometry detector or an ultraviolet absorption detector. Ideally, the detector system allows determination of the quantity of the components of the drug composition and of the byproduct, by weight. This is achieved in practice by measuring the signal obtained upon analysis of one or more known mass(es) of components of the drug composition or byproduct (standards) and then comparing the signal obtained upon analysis of the aerosol to that obtained upon analysis of the standard(s), an approach well known in the art.

In many cases, the structure of a byproduct may not be known or a standard for it may not be available. In such cases, one may calculate the weight fraction of the byproduct by assuming it has an identical response coefficient (e.g. for ultraviolet absorption detection, identical extinction coefficient) to the drug component or components in the drug composition. When conducting such analysis, byproducts present in less than a very small fraction of the drug compound, e.g. less than 0.1% or 0.03% of the drug compound, are typically excluded. Because of the frequent necessity to assume an identical response coefficient between drug and byproduct in calculating a weight percentage of byproduct, it is often more desirable to use an analytical approach in which such an assumption has a high probability of validity. In this respect, high performance liquid chromatography with detection by absorption of ultraviolet light at 225 nm is typically desirable. UV absorption at 250 nm may be used for detection of compounds in cases where the compound absorbs more strongly at 250 nm or for other reasons one skilled in the art would consider detection at 250 nm the most appropriate means of estimating purity by weight using HPLC analysis. In certain cases where analysis of the drug by UV are not viable, other analytical tools such as GC/MS or LC/MS may be used to determine purity.

It is possible that modifying the form of the drug may impact the purity of the aerosol obtained. Although not always the case, the free base or free acid form of the drug as opposed to the salt, generally results in either a higher purity or yield of the resultant aerosol. Therefore, in certain circumstances, it may be more desirable to use the free base or free acid forms of the compounds used. Similarly, it is possible that changing the gas under which vaporization of the composition occurs may also impact the purity.

Other Analytical Methods

Particle size distribution of a drug-containing aerosol may be determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density may be determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2 liters.

Inhalable aerosol drug mass density may be determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the inhalation volume of an inhaling patient, typically about 2 liters. The amount of active drug compound collected in the chamber is determined by extracting the chamber, conducting chromatographic analysis of the extract and comparing the results of the chromatographic analysis to those of a standard containing known amounts of drug.

Inhalable aerosol particle density may be determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size may be determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi * D^3 * \phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation may be determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation may be determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation may be determined, for example, by delivering a drug-containing aerosol into a confined chamber via an inhalation device over a set period of time (e.g., 3 s). Where the aerosol is a pure drug, the amount of drug collected in the chamber is measured as described above. The rate of drug aerosol formation is equal to the amount of drug collected in the chamber divided by the duration of the collection time. Where the drug-containing aerosol comprises a pharmaceutically acceptable excipient, multiplying the rate of aerosol formation by the percentage of drug in the aerosol provides the rate of drug aerosol formation.

Kits

In an embodiment of the invention, a kit is provided for use by a healthcare provider, or more preferably a patient. The kit for delivering a condensation aerosol typically comprises a composition comprising a drug, and a device for forming a condensation aerosol. The composition is typically void of solvents and excipients and generally comprises a heat stable drug. The device for forming a condensation aerosol typically comprises an element configured to heat the composition to form a vapor, an element allowing the vapor to condense to form a condensation aerosol, and an element permitting a user to inhale the condensation aerosol. The device in the kit may further comprise features such as breath-actuation or lockout elements. An exemplary kit will provide a hand-held aerosol delivery device and at least one dose.

In another embodiment, kits for delivering a drug aerosol comprising a thin film of a drug composition and a device for dispensing said film as a condensation aerosol are provided. The composition may contain pharmaceutical excipients. The device for dispensing said film of a drug composition as an aerosol comprises an element configured to heat the film to form a vapor, and an element allowing the vapor to condense to form a condensation aerosol.

In the kits of the invention, the composition is typically coated as a thin film, generally at a thickness between about 0.5-20 microns, on a substrate which is heated by a heat source. Heat sources typically supply heat to the substrate at a rate that achieves a substrate temperature of at least 200° C., preferably at least 250° C., or more preferably at least 300° C. or 350° C., and produces substantially complete volatilization of the drug composition from the substrate within a period of 2 seconds, preferably, within 1 second, or more preferably within 0.5 seconds. To prevent drug degradation, it is preferable that the heat source does not heat the substrate to temperature greater than 600° C. while the drug film is on the substrate to prevent. More preferably, the heat source does not heat the substrate in to temperatures in excess of 500° C.

The kit of the invention can be comprised of various combinations of drugs and drug delivery devices. In some embodiments the device may also be present with another drug. The other drug may be administered orally or topically. Generally, instructions for use are included in the kits.

Utility

As can be appreciated from the above examples showing generation of a pure drug condensation aerosol, from thin films (i.e. 0.05-20 μm) of the drug, the invention finds use in the medical field in compositions and kits for delivery of a drug. Thus, the invention includes, in one aspect, condensation aerosols.

These aerosols can be used for treating a variety of disease states and/or intermittent and acute conditions where rapid systemic absorption and therapeutic effect are highly desirable. Typically the methods of treatment comprise the step of administering a therapeutically effective amount of a drug condensation aerosol to a person with a condition or disease. Typically the step of administering the drug condensation aerosol comprises the step of administering an orally inhalable drug condensation aerosol to the person with the condition. The drug condensation aerosol may be administered in a single inhalation, or in more than one inhalation, as described above.

The drug condensation aerosol may comprise a drug composition as described above. The drug composition typically is a "heat stable drug". In some variations, the condensation aerosol comprises at least one drug selected from the group consisting of acebutolol, acetaminophen, alprazolam, amantadine, amitriptyline, apomorphine diacetate, apomorphine hydrochloride, atropine, azatadine, betahistine, brompheniramine, bumetanide, buprenorphine, bupropion hydrochloride, butalbital, butorphanol, carbinoxamine maleate, celecoxib, chlordiazepoxide, chlorpheniramine, chlorzoxazone, ciclesonide, citalopram, clomipramine, clonazepam, clozapine, codeine, cyclobenzaprine, cyproheptadine, dapsone, diazepam, diclofenac ethyl ester, diflunisal, disopyramide, doxepin, estradiol, ephedrine, estazolam, ethacrynic acid, fenfluramine, fenoprofen, flecainide, flunitrazepam, galanthamine, granisetron, haloperidol, hydromorphone, hydroxychloroquine, ibuprofen, imipramine, indomethacin ethyl ester, indomethacin methyl ester, isocarboxazid, ketamine, ketoprofen, ketoprofen ethyl ester, ketoprofen methyl ester, ketorolac ethyl ester, ketorolac methyl ester, ketotifen, lamotrigine, lidocaine, loperamide, loratadine, loxapine, maprotiline, memantine, meperidine, metaproterenol, methoxsalen, metoprolol, mexiletine HCl, midazolam, mirtazapine, morphine, nalbuphine, naloxone, naproxen, naratriptan, nortriptyline, olanzapine, orphenadrine, oxycodone, paroxetine, pergolide, phenyloin, pindolol, piribedil, pramipexole, procainamide, prochloperazine, propafenone, propranolol, pyrilamine, quetiapine, quinidine, rizatriptan, ropinirole, sertraline, selegiline, sildenafil, spironolactone, tacrine, tadalafil, terbutaline, testosterone, thalidomide, theophylline, tocamide, toremifene, trazodone, triazolam, trifluoperazine, valproic acid, venlafaxine, vitamin E, zaleplon, zotepine, amoxapine, atenolol, benztropine, caffeine, doxylamine, estradiol 17-acetate, flurazepam, flurbiprofen, hydroxyzine, ibutilide, indomethacin norcholine ester, ketorolac norcholine ester, melatonin, metoclopramide, nabumetone, perphenazine, protriptyline HCl, quinine, triamterene, trimipramine, zonisamide, bergapten, chlorpromazine, colchicine, diltiazem, donepezil, eletriptan, estradiol-3,17-diacetate, efavirenz, esmolol, fentanyl, flunisolide, fluoxetine, hyoscyamine, indomethacin, isotretinoin, linezolid, meclizine, paracoxib, pioglitazone, rofecoxib, sumatriptan, tolterodine, tramadol, tranylcypromine, trimipramine maleate, valdecoxib, vardenafil, verapamil, zolmitriptan, zolpidem, zopiclone, bromazepam, buspirone, cinnarizine, dipyridamole, naltrexone, sotalol, telmisartan, temazepam, albuterol, apomorphine hydrochloride diacetate, carbinoxamine, clonidine, diphenhydramine, thambutol, fluticasone proprionate, fluconazole, lovastatin, lorazepam N,O-diacetyl, methadone, nefazodone, oxybutynin, promazine, promethazine, sibutramine, tamoxifen, tolfenamic acid, aripiprazole, astemizole, benazepril, clemastine, estradiol 17-heptanoate, fluphenazine, protriptyline, ethambutal, frovatriptan, pyrilamine maleate, scopolamine, and triamcinolone acetonide. In other variations, the drug is selected from the group consisting of alprazolam, amoxapine, apomorphine hydrochloride, atropine, bumetanide, buprenorphine, butorphanol, celecoxib, ciclesonide, clomipramine, donepezil, eletriptan, fentanyl, hydromorphone, loxapine, midazolam, morphine, nalbuphine, naratriptan, olanzapine, parecoxib, paroxetine, prochlorperazine, quetiapine, sertraline, sibutramine, sildenafil, sumatriptan, tadalafil, valdecoxib, vardenafil, venlafaxine, and zolpidem. In some variations, the drug condensation aerosol has a MMAD in the range of about 1-3 µm.

In another aspect of the invention, kits are provided that include a drug composition and a condensation aerosol delivery device for production of a thermal vapor that contains drug-aerosol particles. The drug delivery article in the device includes a substrate coated with a film of a drug composition to be delivered to a subject, preferably a human subject. The thickness of the drug composition film is selected such that upon vaporizing the film by heating the substrate to a temperature sufficient to vaporize at least 50% of the drug composition film, typically to a temperature of at least about 200° C., preferably at least about 250° C., more preferably at least about 300° C. or 350° C., a thermal vapor is generated that has 10% or less drug-degradation product. The area of the substrate is selected to provide a therapeutic dose, and is readily determined based on the equations discussed above.

EXAMPLES

The following examples further illustrate the invention described herein and are in no way intended to limit the scope of the invention.

Materials

Solvents were of reagent grade or better and purchased commercially.

Unless stated otherwise, the drug free base or free acid form was used in the Examples.

Methods

Preparation of Drug-Coating Solution

Drug was dissolved in an appropriate solvent. Common solvent choices included methanol, dichloromethane, methyl ethyl ketone, diethyl ether, 3:1 chloroform:methanol mixture, 1:1 dichloromethane:methyl ethyl ketone mixture, dimethylformamide, and deionized water. Sonication and/or heat were used as necessary to dissolve the compound. The drug concentration was typically between 50-200 mg/mL.

Preparation of Drug-Coated Stainless Steel Foil Substrate

Strips of clean 304 stainless steel foil (0.0125 cm thick, Thin Metal Sales) having dimensions 1.3 cm by 7.0 cm were dip-coated with a drug solution as prepared according to Method A. The foil was then partially dipped three times into solvent to rinse drug off of the last 2-3 cm of the dipped end of the foil. Alternatively, the drug coating from this area was carefully scraped off with a razor blade. The final coated area was between 2.0-2.5 cm by 1.3 cm on both sides of the foil, for a total area of between 5.2-6.5 $cm^2$ Foils were prepared as stated above and then some were extracted with methanol or acetonitrile as standards. The amount of drug was determined from quantitative HPLC analysis. Using the known drug-coated surface area, the thickness was then obtained by:

$$\text{film thickness (cm)}=\text{drug mass (g)}/[\text{drug density } (g/cm^3)\times\text{substrate area } (cm^2).$$

If the drug density is not known, a value of 1 $g/cm^3$ is assumed. The film thickness in microns is obtained by multiplying the film thickness in cm by 10,000. After drying, the drug-coated foil was placed into a volatilization chamber constructed of a Delrin® block (the airway) and brass bars, which served as electrodes. The dimensions of the airway were 1.3 cm high by 2.6 cm wide by 8.9 cm long. The drug-coated foil was placed into the volatilization chamber such that the drug-coated section was between the two sets of electrodes. After securing the top of the volatilization chamber, the electrodes were connected to a 1 Farad capacitor (Phoenix Gold). The back of the volatilization chamber was connected to a two micron Teflon® filter (Savillex) and filter housing, which were in turn connected to the house vacuum. Sufficient airflow was initiated (typically 30 L/min=1.5 m/sec), at which point the capacitor was charged with a power supply, typically to between 14-17 Volts. The circuit was closed with a switch, causing the drug-coated foil to resistively heat to temperatures of about 280-430° C. (as measured with an infrared camera (FLIR Thermacam SC3000)), in about 200 milliseconds. (For comparison purposes, see FIG. 4A, thermocouple measurement in still air.) After the drug had vaporized, airflow was stopped and the Teflon® filter was extracted with acetonitrile. Drug extracted from the filter was analyzed generally by HPLC UV absorbance generally at 225 nm using a gradient method aimed at detection of impurities to determine percent purity. Also, the extracted drug was quantified to determine a percent yield, based on the mass of drug initially coated onto the substrate. A percent recovery was determined by quantifying any drug remaining on the substrate and chamber walls, adding this to the quantity of drug recovered in the filter and comparing it to the mass of drug initially coated onto the substrate.

Preparation of Drug-Coated Aluminum Foil Substrate

A substrate of aluminum foil (10 cm×5.5 cm; 0.0005 inches thick) was precleaned with acetone. A solution of drug in a minimal amount of solvent was coated onto the foil substrate to cover an area of approximately 7-8 cm×2.5 cm. The solvent was allowed to evaporate. The coated foil was wrapped around a 300 watt halogen tube (Feit Electric Company, Pico Rivera, Calif.), which was inserted into a glass tube sealed at one end with a rubber stopper. Sixty volts of alternating current (driven by line power controlled by a Variac) were run through the bulb for 5-15 seconds, or in some studies 90 V for 3.5-6 seconds, to generate a thermal vapor (including aerosol) which was collected on the glass tube walls. In some studies, the system was flushed through with argon prior to volatilization. The material collected on the glass tube walls was recovered and the following determinations were made: (1) the amount emitted, (2) the percent emitted, and (3) the purity of the aerosol by reverse-phase HPLC analysis with detection typically by absorption of 225 nm light. The initial drug mass was found by weighing the aluminum foil substrate prior to and after drug coating. The drug coating thickness was calculated in the same manner as described in Method B.

Preparation of Drug-Coated Stainless Steel Cylindrical Substrate

A hollow stainless steel cylinder with thin walls, typically 0.12 mm wall thickness, a diameter of 13 mm, and a length of 34 mm was cleaned in dichloromethane, methanol, and acetone, then dried, and fired at least once to remove any residual volatile material and to thermally passivate the stainless steel surface. The substrate was then dip-coated with a drug coating solution (prepared as disclosed in Method A). The dip-coating was done using a computerized dip-coating machine to produce a thin layer of drug on the outside of the substrate surface. The substrate was lowered into the drug solution and then removed from the solvent at a rate of typically 5-25 cm/sec. (To coat larger amounts of material on the substrate, the substrate was removed more rapidly from the solvent or the solution used was more concentrated.) The substrate was then allowed to dry for 30 minutes inside a fume hood. If either dimethylformamide (DMF) or a water mixture was used as a dip-coating solvent, the substrate was vacuum dried inside a desiccator for a minimum of one hour. The drug-coated portion of the cylinder generally has a surface area of 8 $cm^2$. By assuming a unit density for the drug, the initial drug coating thickness was calculated. The amount of drug coated onto the substrates was determined in the same manner as that described in Method B: the substrates were coated, then extracted with methanol or acetonitrile and analyzed with quantitative HPLC methods, to determine the mass of drug coated onto the substrate.

The drug-coated substrate was placed in a surrounding glass tube connected at the exit end via Tygon® tubing to a filter holder fitted with a Teflon® filter (Savillex). The junction of the tubing and the filter was sealed with paraffin film. The substrate was placed in a fitting for connection to two 1 Farad capacitors wired in parallel and controlled by a high current relay. The capacitors were charged by a separate power source to about 18-22 Volts and most of the power was channeled to the substrate by closing a switch and allowing the capacitors to discharge into the substrate. The substrate was heated to a temperature of between about 300-500° C.

(see FIGS. 5A & 5B) in about 100 milliseconds. The heating process was done under an airflow of 15 L/min, which swept the vaporized drug aerosol into a 2 micron Teflon® filter.

After volatilization, the aerosol captured on the filter was recovered for quantification and analysis. The quantity of material recovered in the filter was used to determine a percent yield, based on the mass of drug coated onto the substrate. The material recovered in the filter was also analyzed generally by HPLC UV absorbance at typically 225 nm using a gradient method aimed at detection of impurities, to determine purity of the thermal vapor. Any material deposited on the glass sleeve or remaining on the substrate was also recovered and quantified to determine a percent total recovery ((mass of drug in filter+mass of drug remaining on substrate and glass sleeve)/mass of drug coated onto substrate). For compounds without UV absorption GC/MS or LC/MS was used to determine purity and to quantify the recovery. Some samples were further analyzed by LC/MS to confirm the molecular weight of the drug and any degradants.

Preparation of Drug-Coated Stainless Steel Cylindrical Substrate

A hollow stainless steel cylinder like that described in Example D was prepared, except the cylinder diameter was 7.6 mm and the length was 51 mm. A film of a selected drug was applied as described in Example D.

Energy for substrate heating and drug vaporization was supplied by two capacitors (1 Farad and 0.5 Farad) connected in parallel, charged to 20.5 Volts. The airway, airflow, and other parts of the electrical set up were as described in Example D. The substrate was heated to a temperature of about 420° C. in about 50 milliseconds. After drug film vaporization, percent yield, percent recovery, and purity analysis were done as described in Example D.

Preparation of Drug-Coated Aluminum Foil Substrate

A solution of drug (prepared as described in Method A) was coated onto a substrate of aluminum foil (5 $cm^2$-150 $cm^2$; 0.0005 inches thick). In some studies, the drug was in a minimal amount of solvent, which was allowed to evaporate. The coated foil was inserted into a glass tube in a furnace (tube furnace). A glass wool plug was placed in the tube adjacent to the foil sheet and an air flow of 2 L/min was applied. The furnace was heated to 200-550° C. for 30, 60, or 120 seconds. The material collected on the glass wool plug was recovered and analyzed by reverse-phase HPLC analysis with detection typically by absorption of 225 nm light or GC/MS to determine the purity of the aerosol.

Preparation of Drug-Coated Aluminum Foil Substrate

A substrate of aluminum foil (3.5 cm×7 cm; 0.0005 inches thick) was precleaned with acetone. A solution of drug in a minimal amount of solvent was coated onto the foil substrate. The solvent was allowed to evaporate. The coated foil was wrapped around a 300 watt halogen tube (Feit Electric Company, Pico Rivera, Calif.), which was inserted into a T-shaped glass tube sealed at two ends with parafilm. The parafilm was punctured with ten to fifteen needles for air flow. The third opening was connected to a 1 liter, 3-neck glass flask. The glass flask was further connected to a piston capable of drawing 1.1 liters of air through the flask. Ninety volts of alternating current (driven by line power controlled by a Variac) was run through the bulb for 6-7 seconds to generate a thermal vapor (including aerosol) which was drawn into the 1 liter flask. The aerosol was allowed to sediment onto the walls of the 1 liter flask for 30 minutes. The material collected on the flask walls was recovered and the following determinations were made: (1) the amount emitted, (2) the percent emitted, and (3) the purity of the aerosol by reverse-phase HPLC analysis with detection by typically by absorption of 225 nm light. Additionally, any material remaining on the substrate was collected and quantified.

Example 1

Acebutolol (MW 336, melting point 123° C., oral dose 400 mg), a beta-adrenergic blocker (cardiovascular agent), was coated on a stainless steel cylinder (8 cm$^2$) according to Method D. 0.89 mg of drug was applied to the substrate, for a calculated drug film thickness of 1.1 µm. The substrate was heated as described in Method D at 20.5 V and purity of the drug-aerosol particles was determined to be 98.9%. 0.53 mg was recovered from the filter after vaporization, for a percent yield of 59.6%. A total mass of 0.81 mg was recovered from the test apparatus and substrate, for a total recovery of 91%. High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 130 milliseconds. Generation of the thermal vapor was complete by 500 milliseconds.

Example 2

Acetaminophen (MW 151, melting point 171° C., oral dose 650 mg), an analgesic agent, was coated on an aluminum foil substrate (20 cm$^2$) according to Method C. 2.90 mg of drug was applied to the substrate, for a calculated thickness of the drug film of 1.5 µm. The substrate was heated under argon as described in Method C at 60 V for 6 seconds. The purity of the drug-aerosol particles were determined to be >99.5%. 1.9 mg was recovered from the glass tube walls after vaporization, for a percent yield of 65.5%.

Example 3

Albuterol (MW 239, melting point 158° C., oral dose 0.18 mg), a bronchodilator, was coated onto six stainless steel foil substrates (5 cm$^2$) according to Method B. The calculated thickness of the drug film on each substrate ranged from about 0.5 µm to about 1.6 µm. The substrates were heated as described in Method B by charging the capacitors to 15 V. Purity of the drug-aerosol particles from each substrate was determined and the results are shown in FIG. 23.

Albuterol was also coated on a stainless steel cylinder (8 cm$^2$) according to Method D. 1.20 mg of drug was applied to the substrate, for a calculated drug film thickness of 1.5 µm. The substrate was heated as described in Method D by charging the capacitors to 20.5 V. The purity of the drug-aerosol particles was determined to be 94.4%. 0.69 mg was recovered from the filter after vaporization, for a percent yield of 57.2%. A total mass of 0.9 mg was recovered from the test apparatus and substrate, for a total recovery of 73.5%.

Example 4

Figure 21:
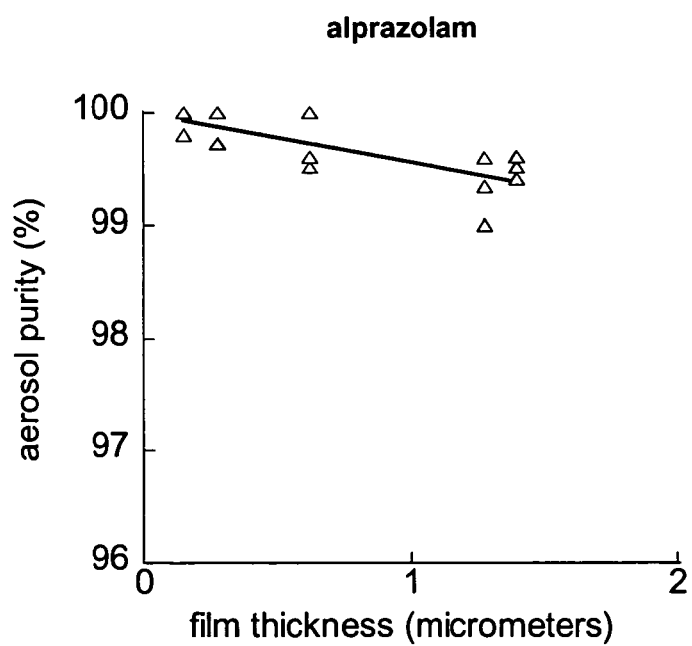
FIG. 21 is plot showing purity of thermal vapor as a function of drug film thickness, in micrometers, for alprazolam free base.
Figure 24A:
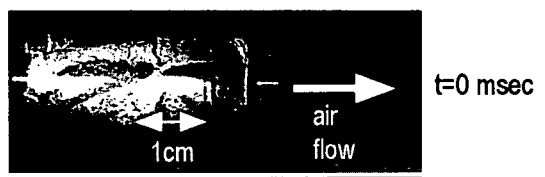
FIGS. 24A-24D are high speed photographs showing the generation of a thermal vapor of phenyloin from a film of drug coated on a substrate drug-supply unit, where the photographs are taken prior to substrate heating (t=0 ms, FIG. 24A) and during substrate heating at times of 50 milliseconds (FIG. 24B), 100 milliseconds (FIG. 24C), and 200 milliseconds (FIG. 24D)
Figure 24B:
Figure 24C:
Figure 24D:

Alprazolam (MW 309, melting point 229° C., oral dose 0.25 mg), an anti-anxiety agent (Xanax®), was coated onto 13 stainless steel cylinder substrates (8 cm$^2$) according to Method D. The calculated thickness of the drug film on each substrate ranged from about 0.1 µm to about 1.4 µm. The substrates were heated as described in Method D by charging the capacitors to 20.5 V. Purity of the drug-aerosol particles from each substrate was determined and the results are shown in FIG. 21.

Another substrate (stainless steel cylinder, 8 cm$^2$) was coated with 0.92 mg of drug, for a calculated drug film thickness of 1.2 µm. The substrate was heated as described in Method D by charging the capacitors to 22.5 V. Purity of the drug-aerosol particles was 99.8%. 0.61 mg was recovered from the filter after vaporization, for a percent yield of 66.2%. A total mass of 0.92 mg was recovered from the test apparatus and substrate, for a total recovery of 100%.

Alprazolam was also coated on an aluminum foil substrate (28.8 cm$^2$) according to Method C. 2.6 mg of the drug was coated on the substrate for a calculated thickness of the drug film of 0.9 µm. The substrate was heated substantially as described in Method C at 75 V for 6 seconds. The purity of the drug-aerosol particles was determined to be 99.9%.

High speed photographs were taken as the drug-coated substrate according to Method D was heated to monitor visually formation of a thermal vapor. The photographs showed that a thermal vapor was initially visible ~35 milliseconds after heating was initiated, with the majority of the thermal vapor formed by 100 milliseconds. Generation of the thermal vapor was complete by 400 milliseconds.

Example 5

Amantadine (MW 151, melting point 192° C., oral dose 100 mg), a dopaminergic agent and an anti-infective agent, was coated on an aluminum foil substrate (20 cm$^2$) according to Method C. A mass of 1.6 mg was coated onto the substrate and the calculated thickness of the drug film was 0.8 µm. The substrate was heated as described in Method C at 90 V for 4 seconds. The purity of the drug-aerosol particles was determined to be 100%. 1.5 mg was recovered from the glass tube walls after vaporization, for a percent yield of 93.8%.

Example 6

Amitriptyline (MW 277, oral dose 50 mg), a tricyclic antidepressant, was coated on a piece of aluminum foil (20 cm$^2$) according to Method C. The calculated thickness of the drug film was 5.2 µm. The substrate was heated as described in Method C at 90 V for 5 seconds. The purity of the drug-aerosol particles was determined to be 98.4%. 5.3 mg was recovered from the glass tube walls after vaporization, for a percent yield of 51.5%.

Amitriptyline was also coated on an identical substrate to a thickness of 1.1 µm. The substrate was heated as described in Method C under an argon atmosphere at 90 V for 3.5 seconds. The purity of the drug-aerosol particles was determined to be 99.3%. 1.4 mg was recovered from the glass tube walls after vaporization, for a percent yield of 63.6%.

Example 7

Apomorphine diacetate (MW 351), a dopaminergic agent used as an anti-Parkinsonian drug, was coated on a piece of aluminum foil (20 cm$^2$) according to Method C. The calculated thickness of the drug film was 1.1 µm. The substrate was heated as described in Method C at 90 V for 3 seconds. The purity of the drug-aerosol particles was determined to be 96.9%. 2 mg was recovered from the glass tube walls after vaporization, for a percent yield of 90.9%.

Example 8

The hydrochloride salt form of apomorphine was also tested. Apomorphine hydrochloride (MW 304) was coated on a stainless steel foil (6 cm$^2$) according to Method B. 0.68 mg of drug was applied to the substrate, for a calculated drug film thickness of 1.1 µm. The substrate was heated as described in Method B by charging the capacitor to 15 V. The purity of the drug-aerosol particles was determined to be 98.1%. 0.6 mg was recovered from the filter after vaporization, for a percent yield of 88.2%. A total mass of 0.68 mg was recovered from the test apparatus and substrate, for a total recovery of 100%.

Example 9

The hydrochloride diacetate salt of apomorphine was also tested (MW 388). Apomorphine hydrochloride diacetate was coated on a piece of aluminum foil (20 cm$^2$) according to Method C. The calculated thickness of the drug film was 1.0 µm. The substrate was heated as described in Method C at 90 V for 3 second. purity of the drug-aerosol particles was determined to be 94.0%. 1.65 mg was recovered from the glass tube walls after vaporization, for a percent yield of 86.8%.

Example 10

Atropine (MW 289, melting point 116° C., oral dose 0.4 mg), an muscarinic antagonist, was coated on five stainless steel cylinder substrates (8 cm$^2$) according to Method D. The calculated thickness of the drug films ranged from about 1.7 µm to 9.0 µm. The substrate was heated as described in Method D by charging the capacitors to 19 or 22 V. Purity of the drug-aerosol particles from each substrate was determined. The results are shown in FIG. 6. For the substrate having a drug film thickness of 1.7 µm, 1.43 mg of drug was applied to the substrate. After volatilization of drug from this substrate with a capacitor charged to 22 V, 0.95 mg was recovered from the filter, for a percent yield of 66.6%. The purity of the drug aerosol recovered from the filter was found to be 98.5%. A total mass of 1.4 mg was recovered from the test apparatus and substrate, for a total recovery of 98.2%.

High speed photographs were taken as the drug-coated substrate was heated to monitor visually formation of a thermal vapor. The photographs showed that a thermal vapor was initially visible 28 milliseconds after heating was initiated, with the majority of the thermal vapor formed by 90 milliseconds. Generation of the thermal vapor was complete by 140 milliseconds.

Example 11

Azatadine (MW 290, melting point 126° C., oral dose 1 mg), an antihistamine, was coated on an aluminum foil substrate (20 cm$^2$) according to Method C. 5.70 mg of drug was applied to the substrate, for a calculated thickness of the drug film of 2.9 µm. The substrate was heated as described in Method C at 60 V for 6 seconds. The purity of the drug-aerosol particles was determined to be 99.6%. 2.8 mg was recovered from the glass tube walls after vaporization, for a percent yield of 49.1%. Another azatadine-coated substrate was prepared according to Method G. The substrate was heated as described in Method G at 60 V for 6 seconds under an argon atmosphere. The purity of the drug-aerosol particles was determined to be 99.6%. The percent yield of the aerosol was 62%.

Example 12

Bergapten (MW 216, melting point 188° C., oral dose 35 mg), an anti-psoriatic agent, was coated on a stainless steel cylinder (8 cm$^2$) according to Method D. 1.06 mg of drug was applied to the substrate, for a calculated drug film thickness of 1.3 µm. The substrate was heated as described in Method D by charging the capacitors to 20.5 V. The purity of the drug-aerosol particles was determined to be 97.8%. 0.72 mg was recovered from the filter after vaporization, for a percent yield of 67.9%. A total mass of 1.0 mg was recovered from the test apparatus and substrate, for a total recovery of 98.1%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 85 milliseconds. Generation of the thermal vapor was complete by 140 milliseconds.

Example 13

Betahistine (MW 136, melting point <25° C., oral dose 8 mg), a vertigo agent, was coated on a metal substrate according to Method F and heated to 300° C. to form drug-aerosol particles. Purity of the drug-aerosol particles was determined to be 99.3%. 17.54 mg was recovered from the glass wool after vaporization, for a percent yield of 58.5%.

Example 14

Brompheniramine (MW 319, melting point <25° C., oral dose 4 mg), an anti-histamine agent, was coated on an aluminum foil substrate (20 cm$^2$) according to Method C. 4.50 mg of drug was applied to the substrate, for a calculated thickness of the drug film of 2.3 µm. The substrate was heated as described in Method C at 60 V for 8 seconds. The purity of the drug-aerosol particles was determined to be 99.8%. 3.12 mg was recovered from the glass tube walls after vaporization, for a percent yield of 69.3%. An identical substrate with the same thickness of brompheniramine (4.5 mg drug applied to substrate) was heated under an argon atmosphere at 60 V for 8 seconds. The purity of the drug-aerosol particles was determined to be 99.9%. 3.3 mg was recovered from the glass tube walls after vaporization, for a percent yield of 73.3%.

The maleate salt form of the drug was also tested. Brompheniramine maleate (MW 435, melting point 134° C., oral dose 2 mg) was coated onto an aluminum foil substrate (20 cm$^2$) according to Method C. The calculated thickness of the drug film was 2.8 µm. The substrate was heated as described in Method C at 60 V for 7 seconds. The purity of the drug-aerosol particles was determined to be 99.6%. 3.4 mg was recovered from the glass tube walls after vaporization, for a percent yield of 60.7%. An identical substrate with a 3.2 µm brompheniramine maleate film was heated under an argon atmosphere at 60 V for 7 seconds. The purity of the drug-aerosol particles was determined to be 100%. 3.2 mg was recovered from the glass tube walls after vaporization, for a percent yield of 50%.

Example 15

Bumetanide (MW 364, melting point 231° C., oral dose 0.5 mg), a cardiovascular agent and diuretic, was coated on a stainless steel cylinder (8 cm$^2$) according to Method D. 1.09 mg of drug was applied to the substrate, for a calculated drug film thickness of 1.3 µm. The substrate was heated as described in Method D by charging the capacitors to 20.5 V. The purity of the drug-aerosol particles was determined to be 98.4%. 0.56 mg was recovered from the filter after vaporization, for a percent yield of 51.4%. A total mass of 0.9 mg was recovered from the test apparatus and substrate, for a total recovery of 82.6%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 300 milliseconds. Generation of the thermal vapor was complete by 1200 milliseconds.

Example 16

Buprenorphine (MW 468, melting point 209° C., oral dose 0.3 mg), an analgesic narcotic, was coated on a piece of aluminum foil (20 cm$^2$) according to Method C. The calculated thickness of the drug film was 0.7 µm. The substrate was heated as described in Method C at 60 V for 5 seconds. The purity of the drug-aerosol particles was determined to be 98%. 1.34 mg was recovered from the glass tube walls after vaporization, for a percent yield of 95.7%.

Figure 9:
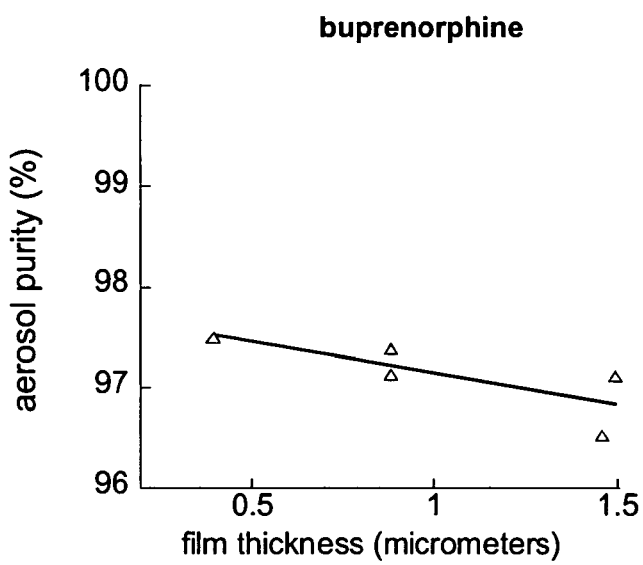
Figure 12:
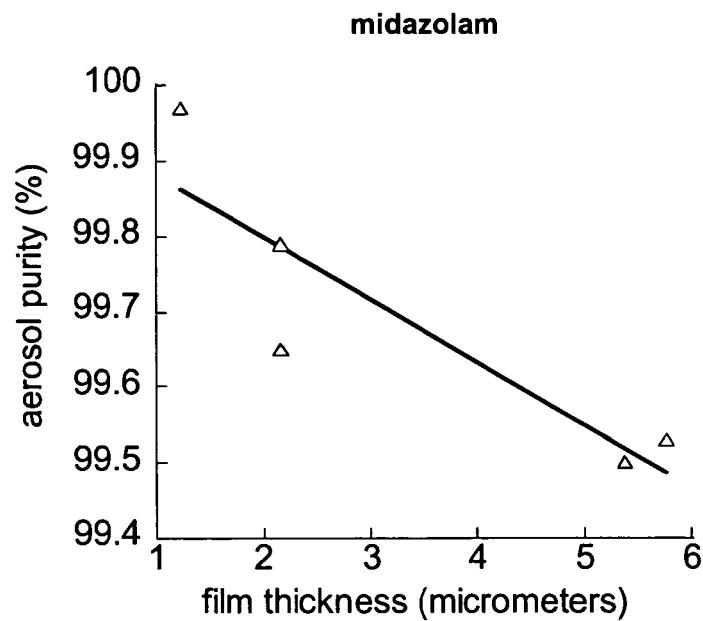
FIG. 12 is plot showing purity of thermal vapor as a function of drug film thickness, in micrometers, for midazolam free base.
Figure 13:
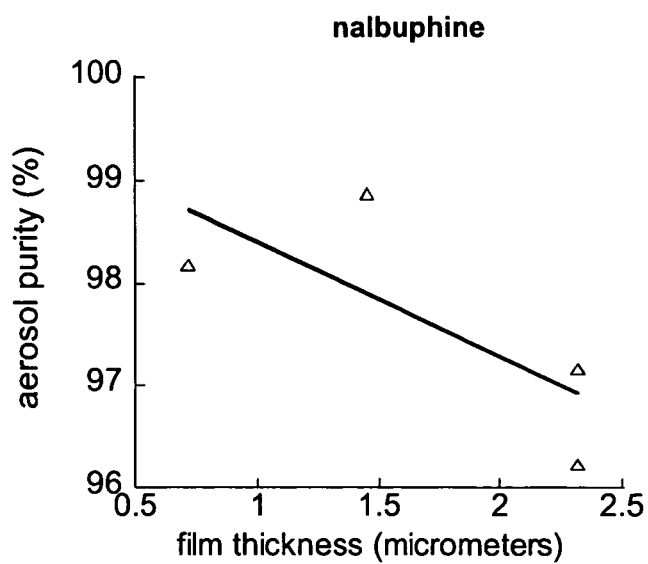
FIG. 13 is plot showing purity of thermal vapor as a function of drug film thickness, in micrometers, for nalbuphine free base.
Figure 14:
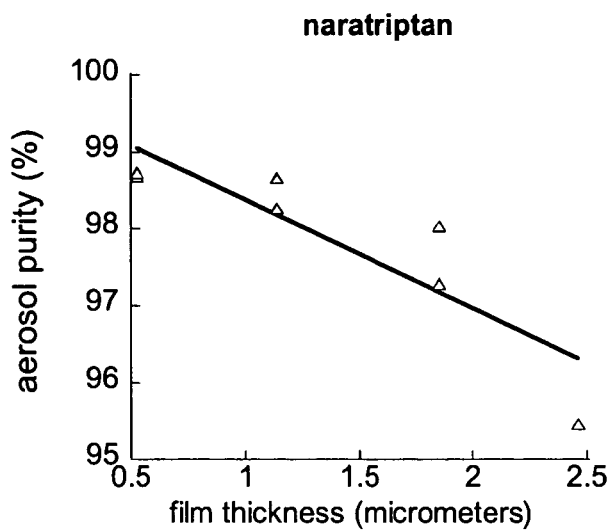
FIG. 14 is plot showing purity of thermal vapor as a function of drug film thickness, in micrometers, for naratriptan free base.
Figure 15:
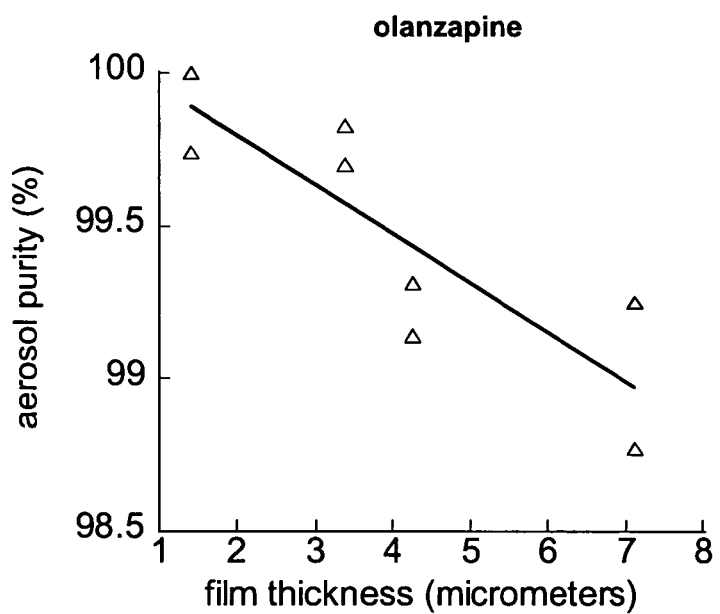
FIG. 15 is plot showing purity of thermal vapor as a function of drug film thickness, in micrometers, for olanzapine free base.
Figure 16:
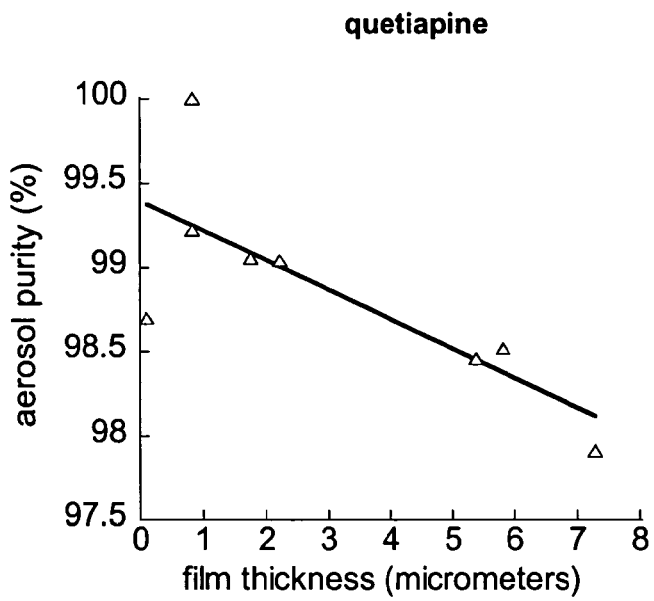
FIG. 16 is plot showing purity of thermal vapor as a function of drug film thickness, in micrometers, for quetiapine free base.

Buprenorphine was also coated onto five stainless steel cylinder substrates (8 cm$^2$) according to Method D except that a 1.5 Farad capacitor was used as opposed to a 2.0 Farad capacitor. The calculated thickness of the drug film on each substrate ranged from about 0.3 µm to about 1.5 µm. The substrates were heated as described in Method D (with the single exception that the circuit capacitance was 1.5 Farad, not 2.0 Farad) and purity of the drug-aerosol particles determined. The results are shown in FIG. 9. For the substrate having a 1.5 µm drug film, 1.24 mg of drug was applied to the substrate. After volatilization of drug from this substrate by charging the capacitors to 20.5 V, 0.865 mg was recovered from the filter, for a percent yield of 69.5%. A total mass of 1.2 mg was recovered from the test apparatus and substrate, for a total recovery of 92.9%. The purity of the drug aerosol recovered from the filter was determined to be 97.1%.

High speed photographs were taken as one of the drug-coated substrates was heated, to monitor visually formation of a thermal vapor. The photographs, shown in FIGS. 26A-26E, showed that a thermal vapor was initially visible 30 milliseconds after heating was initiated, with the majority of the thermal vapor formed by 120 milliseconds. Generation of the thermal vapor was complete by 300 milliseconds.

The salt form of the drug, buprenorphine hydrochloride (MW 504), was also tested. The drug was coated on a piece of aluminum foil (20 cm$^2$) according to Method C. 2.10 mg of drug was applied to the substrate, for a calculated thickness of the drug film of 1.1 µm. The substrate was heated as described in Method C at 60 V for 15 seconds. The purity of the drug-aerosol particles was determined to be 91.4%. 1.37 mg was recovered from the glass tube walls after vaporization, for a percent yield of 65.2%. Buprenorphine was further coated on an aluminum foil substrate (24.5 cm$^2$) according to Method G. 1.2 mg of the drug was applied to the substrate, for a calculated thickness of the drug film of 0.49 µm. The substrate was heated substantially as described in Method G at 90 V for 6 seconds, except that two of the openings of the T-shaped tube were left open and the third connected to the 1 L flask. The purity of the drug-aerosol particles was determined to be >99%. 0.7 mg of the drug was found to have aerosolized, for a percent yield of 58%.

Example 17

Bupropion hydrochloride (MW 276, melting point 234° C., oral dose 100 mg), an antidepressant psychotherapeutic agent, was coated on a piece of aluminum foil (20 cm$^2$) according to Method C. The calculated thickness of the drug film was 1.2 µm. The substrate was heated as described in Method C at 90 V for 3.5 seconds. The purity of the drug-aerosol particles was determined to be 98.5%. 2.1 mg was recovered from the glass tube walls after vaporization, for a percent yield of 91.3%. An identical substrate having the same drug film thickness was heated under an argon atmosphere according to Method C at 90 V for 3.5 seconds. 1.8 mg was recovered from the glass tube walls after vaporization, for a percent yield of 78.3%. The recovered vapor had a purity of 99.1%.

Example 18

Butalbital (MW 224, melting point 139° C., oral dose 50 mg), a sedative and hypnotic barbituate, was coated on a piece of aluminum foil (20 cm$^2$) according to Method C. 2.3 mg were coated on the foil, for a calculated thickness of the drug film of 1.2 µm. The substrate was heated as described in Method C at 90 V for 3.5 seconds. The purity of the drug-aerosol particles was determined to be >99.5%. 1.69 mg were collected for a percent yield of 73%.

Example 19

Butorphanol (MW 327, melting point 217° C., oral dose 1 mg), an analgesic narcotic agent, was coated on a piece of aluminum foil (20 cm$^2$) according to Method C. The calculated thickness of the drug film was 1.0 µm. The substrate was heated as described in Method C at 90 V for 3.5 seconds. The purity of the drug-aerosol particles was determined to be 98.7%.

Butorphanol was also coated on a stainless steel cylinder (6 cm$^2$) according to Method E. 1.24 mg of drug was applied to the substrate, for a calculated drug film thickness of 2.1 µm. The substrate was heated as described in Method E and purity of the drug-aerosol particles was determined to be 99.4%. 0.802 mg was recovered from the filter after vaporization, for a percent yield of 64.7%. A total mass of 1.065 mg was recovered from the test apparatus and substrate, for a total recovery of 85.9%. High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 60 milliseconds. Generation of the thermal vapor was complete by 90 milliseconds.

Example 20

Carbinoxamine (MW 291, melting point <25° C., oral dose 2 mg), an antihistamine, was coated on a piece of aluminum foil (20 cm$^2$) according to Method C. 5.30 mg of drug was applied to the substrate, for a calculated thickness of the drug film of 2.7 µm. The substrate was heated as described in Method C at 60 V for 6 seconds. The purity of the drug-aerosol particles was determined to be 92.5%. 2.8 mg was recovered from the glass tube walls after vaporization, for a percent yield of 52.8%. A second substrate was coated with carbinoxamine (6.5 mg drug) to a thickness of 3.3 µm. The substrate was heated as described in Method C at 90 V for 6 seconds under an argon atmosphere. The purity of the drug-aerosol particles determined was to be 94.8%. 3.1 mg was recovered from the glass tube walls after vaporization, for a percent yield of 47.7%.

The maleate salt form of the drug was also tested. Carbinoxamine maleate (MW 407, melting point 119° C., oral dose 4 mg) was coated on a piece of aluminum foil (20 cm$^2$) according to Method C. The calculated thickness of the drug film was 3.9 µm. The substrate was heated as described in Method C at 90 V for 6 seconds. The purity of the drug-aerosol particles was determined to be 99%. 4.8 mg was recovered from the glass tube walls after vaporization, for a percent yield of 62.3%.

Example 21

Celecoxib (MW 381, melting point 159° C., oral dose 100 mg), an analgesic non-steroidal anti-inflammatory agent, was coated on a piece of stainless steel foil (5 cm$^2$) according to Method B. 4.6 mg of drug was applied to the substrate, for a calculated drug film thickness of 8.7 µm. The substrate was heated as described in Method B by charging the capacitors to 16 V. The purity of the drug-aerosol particles was determined to be >99.5%. 4.5 mg was recovered from the filter after vaporization, for a percent yield of 97.8%. A total mass of 4.6 mg was recovered from the test apparatus and substrate, for a total recovery of 100%.

Celecoxib was also coated on a piece of aluminum foil (100 $cm^2$) according to Method G. The calculated thickness of the drug film was 3.1 μm. The substrate was heated as described in Method G at 60 V for 15 seconds. The purity of the drug-aerosol particles was determined to be 99%. 24.5 mg was recovered from the glass tube walls after vaporization, for a percent yield of 79%.

Example 22

Chlordiazepoxide (MW 300, melting point 237° C., oral dose 5 mg), a sedative and hypnotic agent, was coated on a piece of aluminum foil (20 $cm^2$) according to Method C. The calculated thickness of the drug film was 2.3 μm. The substrate was heated as described in Method C at 45 V for 15 seconds. The purity of the drug-aerosol particles was determined to be 98.2%. 2.5 mg was recovered from the glass tube walls after vaporization, for a percent yield of 54.3%.

Example 23

Chlorpheniramine (MW 275, melting point <25° C., oral dose 4 mg), an antihistamine, was coated onto an aluminum foil substrate (20 $cm^2$) according to Method C. 5.90 mg of drug was applied to the substrate, for a calculated thickness of the drug film of 3 μm. The substrate was heated as described in Method C at 60 V for 10 seconds. The purity of the drug-aerosol particles was determined to be 99.8%. 4.14 mg was recovered from the glass tube walls after vaporization, for a percent yield of 70.2%. The maleate salt form (MW 391, melting point 135° C., oral dose 8 mg) was coated on an identical substrate to a thickness of 1.6 μm. The substrate was heated as described in Method C at 60 V for 7 seconds. The purity of the drug-aerosol particles was determined to be 99.6%. 2.1 mg was recovered from the glass tube walls after vaporization, for a percent yield of 65.6%.

Example 24

Chlorpromazine (MW 319, melting point <25° C., oral dose 300 mg), an antipsychotic, psychotherapeutic agent, was coated on an aluminum foil substrate (20 $cm^2$) according to Method C. 9.60 mg of drug was applied to the substrate, for a calculated thickness of the drug film of 4.8 μm. The substrate was heated as described in Method C at 90 V for 5 seconds. The purity of the drug-aerosol particles was determined to be 96.5%. 8.6 mg was recovered from the glass tube walls after vaporization, for a percent yield of 89.6%.

Example 25

Chlorzoxazone (MW 170, melting point 192° C., oral dose 250 mg), a muscle relaxant, was coated on a piece of aluminum foil (20 $cm^2$) according to Method C. The calculated thickness of the drug film was 1.3 μm. The substrate was heated as described in Method C at 90 V for 3.5 seconds. The purity of the drug-aerosol particles was determined to be 99.7%. 1.55 mg was recovered from the glass tube walls after vaporization, for a percent yield of 59.6%.

Example 26

Ciclesonide (MW 541, melting point 206.5-207° C., oral dose 0.2 mg) a glucocorticoid, was coated on stainless steel foil substrates (6 $cm^2$) according to Method B. Eight substrates were prepared, with the drug film thickness ranging from about 0.4 μm to about 2.4 μm. The substrates were heated as described in Method B, with the capacitors charged with 15.0 or 15.5 V. Purity of the drug-aerosol particles from each substrate was determined and the results are shown in FIG. 11. The substrate having a thickness of 0.4 μm was prepared by depositing 0.204 mg drug on the substrate surface. After volatilization of drug from this substrate using capacitors charged to 15.0 V, 0.201 mg was recovered from the filter, for a percent yield of 98.5%. The purity of the drug aerosol particles was determined to be 99%. A total mass of 0.204 mg was recovered from the test apparatus and substrate, for a total recovery of 100%.

Example 27

Citalopram (MW 324, melting point <25° C., oral dose 20 mg), a psychotherapeutic agent, was coated onto an aluminum foil substrate (20 $cm^2$) according to Method C. 8.80 mg of drug was applied to the substrate, for a calculated thickness of the drug film of 4.4 μm. The substrate was heated as described in Method C at 90 V for 4 seconds. The purity of the drug-aerosol particles was determined to be 92.3%. 5.5 mg was recovered from the glass tube walls after vaporization, for a percent yield of 62.5%. Another substrate containing citalopram coated (10.10 mg drug) to a film thickness of 5 μm was prepared by the same method and heated under an argon atmosphere. The purity of the drug-aerosol particles was determined to be 98%. 7.2 mg was recovered from the glass tube walls after vaporization, for a percent yield of 71.3%.

Example 28

Clomipramine (MW 315, melting point <25° C., oral dose 150 mg), a psychotherapeutic agent, was coated onto eight stainless steel cylindrical substrates according to Method E. The calculated thickness of the drug film on each substrate ranged from about 0.8 μm to about 3.9 μm. The substrates were heated as described in Method E and purity of the drug-aerosol particles determined. The results are shown in FIG. 10. For the substrate having a drug film thickness of 0.8 μm, 0.46 mg of drug was applied to the substrate. After volatilization of drug from this substrate, 0.33 mg was recovered from the filter, for a percent yield of 71.7%. Purity of the drug-aerosol particles was determined to be 99.4%. A total mass of 0.406 mg was recovered from the test apparatus and substrate, for a total recovery of 88.3%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 75 milliseconds. Generation of the thermal vapor was complete by 115 milliseconds.

Example 29

Clonazepam (MW 316, melting point 239° C., oral dose 1 mg), an anticonvulsant, was coated on an aluminum foil substrate (50 cm$^2$) and heated according to Method F to a temperature of 350° C. to form drug-aerosol particles. 46.4 mg of the drug was applied to the substrate, for a calculated thickness of the drug film of 9.3 μm. Purity of the drug-aerosol particles was determined to be 14%.

Clonazepam was further coated on an aluminum foil substrate (24 cm$^2$) according to Method C. 5 mg of the drug was applied to the substrate, for a calculated thickness of the drug film of 2.1 μm. The substrate was heated substantially as described in Method C at 60 V for 8 seconds. The purity of the drug-aerosol particles was determined to be 99.9%.

Example 30

Clonidine (MW 230, melting point 130° C., oral dose 0.1 mg), a cardiovascular agent, was coated on an aluminum foil substrate (50 cm$^2$) and heated according to Method F at 300° C. to form drug-aerosol particles. Purity of the drug-aerosol particles was determined to be 94.9%. The yield of aerosol particles was 90.9%.

Example 31

Clozapine (MW 327, melting point 184° C., oral dose 150 mg), a psychotherapeutic agent, was coated on an aluminum foil substrate (20 cm$^2$) according to Method C. 14.30 mg of drug was applied to the substrate, for a calculated thickness of the drug film of 7.2 μm. The substrate was heated as described in Method C at 90 V for 5 seconds. The purity of the drug-aerosol particles was determined to be 99.1%. 2.7 mg was recovered from the glass tube walls after vaporization, for a percent yield of 18.9%. Another substrate containing clozapine coated (2.50 mg drug) to a film thickness of 1.3 μm was prepared by the same method and heated under an argon atmosphere at 90 V for 3.5 seconds. The purity of the drug-aerosol particles was determined to be 99.5%. 1.57 mg was recovered from the glass tube walls after vaporization, for a percent yield of 62.8%.

Example 32

Codeine (MW 299, melting point 156° C., oral dose 15 mg), an analgesic, was coated on an aluminum foil substrate (20 cm$^2$) according to Method C. 8.90 mg of drug was applied to the substrate, for a calculated thickness of the drug film of 4.5 μm. The substrate was heated as described in Method C at 90 V for 5 seconds. The purity of the drug-aerosol particles was determined to be 98.1%. 3.46 mg was recovered from the glass tube walls after vaporization, for a percent yield of 38.9%.

Another substrate containing codeine coated (2.0 mg drug) to a film thickness of 1 μm was prepared by the same method and heated under an argon atmosphere at 90 V for 3.5 seconds. The purity of the drug-aerosol particles was determined to be >99.5%. 1 mg was recovered from the glass tube walls after vaporization, for a percent yield of 50%.

Example 33

Colchicine (MW 399, melting point 157° C., oral dose 0.6 mg), a gout preparation, was coated on a stainless steel cylinder (8 cm$^2$) according to Method D. 1.12 mg of drug was applied to the substrate, for a calculated drug film thickness of 1.3 μm. The substrate was heated as described in Method D by charging the capacitors to 20.5 V. The purity of the drug-aerosol particles was determined to be 97.7%. 0.56 mg was recovered from the filter after vaporization, for a percent yield of 50%. A total mass of 1.12 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 140 milliseconds. Generation of the thermal vapor was complete by 700 milliseconds.

Example 34

Cyclobenzaprine (MW 275, melting point <25° C., oral dose 10 mg), a muscle relaxant, was coated on an aluminum foil substrate (20 cm$^2$) according to Method C. 9.0 mg of drug was applied to the substrate, for a calculated thickness of the drug film of 4.5 μm. The substrate was heated as described in Method C at 90 V for 5 seconds. The purity of the drug-aerosol particles was determined to be 99%. 6.33 mg was recovered from the glass tube walls after vaporization, for a percent yield of 70.3%.

Example 35

Cyproheptadine (MW 287, melting point 113° C., oral dose 4 mg), an antihistamine, was coated on an aluminum foil substrate (20 cm$^2$) according to Method C. 4.5 mg of drug was applied to the substrate, for a calculated thickness of the drug film of 2.3 μm. The substrate was heated as described in Method C at 60 V for 8 seconds. The purity of the drug-aerosol particles was determined to be >99.5%. 3.7 mg was recovered from the glass tube walls after vaporization, for a percent yield of 82.2%.

Cyproheptadine HCl salt (MW 324, melting point 216° C., oral dose 4 mg) was coated on an identical substrate to a thickness of 2.2 μm. The substrate was heated at 60V for 8 seconds. The purity of the drug-aerosol particles was determined to be 99.6%. 2.6 mg was recovered from the glass tube walls after vaporization, for a percent yield of 60.5%.

Example 36

Dapsone (MW 248, melting point 176° C., oral dose 50 mg), an anti-infective agent, was coated on a stainless steel cylinder (8 cm$^2$) according to Method D. 0.92 mg of drug was applied to the substrate, for a calculated drug film thickness of 1.1 μm. The substrate was heated as described in Method D by charging the capacitors to 20.5 V. The purity of the drug-aerosol particles was determined to be >99.5%. 0.92 mg was recovered from the filter after vaporization, for a percent yield of 100%. The total mass was recovered from the test apparatus and substrate, for a total recovery of about 100%.

Example 37

Diazepam (MW 285, melting point 126° C., oral dose 2 mg), a sedative and hypnotic, was coated on an aluminum foil substrate (20 cm$^2$) according to Method C. 5.30 mg of drug was applied to the substrate, for a calculated thickness of the drug film of 2.7 µm. The substrate was heated as described in Method C at 40 V for 17 seconds. The purity of the drug-aerosol particles was determined to be 99.9%. 4.2 mg was recovered from the glass tube walls after vaporization, for a percent yield of 79.2%.

Diazepam was also coated on a circular aluminum foil substrate (78.5 cm$^2$). 10.0 mg of drug was applied to the substrate, for a calculated film thickness of the drug of 1.27 µm. The substrate was secured to the open side of a petri dish (100 mm diameter×50 mm height) using parafilm. The glass bottom of the petri dish was cooled with dry ice, and the aluminum side of the apparatus was placed on a hot plate at 240° C. for 10 seconds. The material collected on the beaker walls was recovered and analyzed by HPLC analysis with detection by absorption of 225 nm light used to determine the purity of the aerosol. Purity of the drug-aerosol particles was determined to be 99.9%.

Diazepam was also coated on an aluminum foil substrate (36 cm$^2$) according to Method G. 5.1 mg of drug was applied to the substrate, for a calculated thickness of the drug film of 1.4 µm. The substrate was heated substantially as described in Method G, except that 90 V for 6 seconds was used, and purity of the drug-aerosol particles was determined to be 99%. 3.8 mg was recovered from the glass tube walls after vaporization, for a percent yield of 74.5%.

Example 38

Diclofenac ethyl ester (MW 324, oral dose 50 mg), an antirheumatic agent, was coated on a metal substrate (50 cm$^2$) and heated according to Method F at 300° C. to form drug-aerosol particles. 50 mg of drug was applied to the substrate, for a calculated thickness of the drug film of 10 μm. Purity of the drug-aerosol particles was determined to be 100% by GC analysis. The yield of aerosol particles was 80%.

Example 39

Diflunisal (MW 250, melting point 211° C., oral dose 250 mg), an analgesic, was coated on a piece of aluminum foil (20 $cm^2$) according to Method C. The calculated thickness of the drug film was 5.3 μm. The substrate was heated as described in Method C at 60 V for 6 seconds. The purity of the drug-aerosol particles was determined to be >99.5%. 5.47 mg was recovered from the glass tube walls after vaporization, for a percent yield of 51.6%.

Example 40

Diltiazem (MW 415, oral dose 30 mg), a calcium channel blocker used as a cardiovascular agent, was coated on a stainless steel cylinder (8 $cm^2$) according to Method D. 0.8 mg of drug was applied to the substrate, for a calculated drug film thickness of 1 μm. The substrate was heated as described in Method D by charging the capacitors to 20.5V. The purity of the drug-aerosol particles was determined to be 94.2%. 0.53 mg was recovered from the filter after vaporization, for a percent yield of 66.3%. A total mass of 0.8 mg was recovered from the test apparatus and substrate, for a total recovery of 100%.

The drug was also coated on a piece of aluminum foil (20 $cm^2$) according to Method C. The calculated thickness of the drug film was 1.0 μm. The substrate was heated as described in Method C at 90 V for 3.5 seconds. The purity of the drug-aerosol particles was determined to be 85.5%. 1.91 mg was recovered from the glass tube walls after vaporization, for a percent yield of 95.5%.

Diltiazem was also coated on a piece of aluminum foil (20 $cm^2$) according to Method C. The calculated thickness of the drug film was 1.1 μm. The substrate was heated as described in Method C at 90 V for 3.5 seconds under an argon atmosphere. The purity of the drug-aerosol particles was determined to be 97.1%. 1.08 mg was recovered from the glass tube walls after vaporization, for a percent yield of 49.1%.

Example 41

Diphenhydramine (MW 255, melting point <25° C., oral dose 25 mg), an antihistamine, was coated on an aluminum foil substrate (20 $cm^2$) according to Method C. 5.50 mg of drug was applied to the substrate, for a calculated thickness of the drug film of 2.8 μm. The substrate was heated as described in Method C at 108 V for 2.25 seconds. The purity of the drug-aerosol particles was determined to be 93.8%. 3.97 mg was recovered from the glass tube walls after vaporization, for a percent yield of 72.2%.

The hydrochloride salt was also tested. 4.90 mg of drug was coated onto an aluminum substrate, for a calculated thickness of the drug film of 2.5 μm. The substrate was heated under an argon atmosphere as described in Method C at 60 V for 10 seconds. The purity of the drug-aerosol particles was determined to be 90.3%. 3.70 mg was recovered from the glass tube walls after vaporization, for a percent yield of 75.5%. Another experiment with the hydrochloride salt was done under an argon atmosphere. 5.20 mg of drug was coated onto an aluminum substrate, for a calculated thickness of the drug film of 2.6 μm. The substrate was heated as described in Method C at 60 V for 10 seconds. The purity of the drug-aerosol particles was determined to be 93.3%. 3.90 mg was recovered from the glass tube walls after vaporization, for a percent yield of 75.0%.

Example 42

Disopyramide (MW 339, melting point 95° C., oral dose 100 mg), a cardiovascular agent, was coated on a stainless steel cylinder (8 $cm^2$) according to Method D. 1.07 mg of drug was applied to the substrate, for a calculated drug film thickness of 1.3 μm. The substrate was heated as described in Method D by charging the capacitors to 20.5 V. The purity of the drug-aerosol particles was determined to be 99%. 0.63 mg was recovered from the filter after vaporization, for a percent yield of 58.9%. A total mass of 0.9 mg was recovered from the test apparatus and substrate, for a total recovery of 84.1%.

High speed photographs were taken as the drug-coated substrate was heated to monitor visually formation of a thermal vapor. The photographs, shown in FIGS. 25A-25D, showed that a thermal vapor was initially visible 50 milliseconds after heating was initiated, with the majority of the thermal vapor formed by 100 milliseconds. Generation of the thermal vapor was complete by 200 milliseconds.

Example 43

Doxepin (MW 279, melting point <25° C. oral dose 75 mg), a psychotherapeutic agent, was coated on an aluminum foil substrate (20 $cm^2$) according to Method C. 2.0 mg of drug was applied to the substrate, for a calculated thickness of the drug film of 1.0 μm. The substrate was heated as described in Method C at 90 V for 3.5 seconds. The purity of the drug-aerosol particles was determined to be 99%. The total mass recovered from the glass tube walls after vaporization ~100%.

Another substrate containing doxepin was also prepared. On an aluminum foil substrate (20 cm$^2$) 8.6 mg of drug was applied to the substrate, for a calculated thickness of the drug film of 4.5 µm. The substrate was heated as described in Method C at 90 V for 5 seconds. The purity of the drug-aerosol particles was determined to be 81.1%. 6.4 mg was recovered from the glass tube walls after vaporization, for a percent yield of 74.4%.

Another substrate containing doxepin was also prepared for testing under argon. On an aluminum foil substrate (20 cm$^2$) 1.8 mg of drug was applied to the substrate, for a calculated thickness of the drug film of 0.9 µm. The substrate was heated as described in Method C at 90 V for 3.5 seconds. The purity of the drug-aerosol particles was determined to be 99.1%. The total mass recovered from the glass tube walls after vaporization ~100%.

Example 44

Donepezil (MW 379, oral dose 5 mg), a drug used in management of Alzheimer's, was coated on a stainless steel cylinder (8 cm$^2$) according to Method D. 5.73 mg of drug was applied to the substrate, for a calculated drug film thickness of 6.9 µm. The substrate was heated as described in Method D by charging the capacitors to 20.5 V. The purity of the drug-aerosol particles was determined to be 96.9%. 3 mg was recovered from the filter after vaporization, for a percent yield of 52.4%. A total mass of 3 mg was recovered from the test apparatus and substrate, for a total recovery of 52.4%.

Donepezil was also tested according to Method B, by coating a solution of the drug onto a piece of stainless steel foil (5 cm$^2$). Six substrates were prepared, with film thicknesses ranging from about 0.5 µm to about 3.2 µm. The substrates were heated as described in Method B by charging the capacitors to 14.5 or 15.5 V. Purity of the drug aerosol particles from each substrate was determined. The results are shown in FIG. 7.

Donepezil was also tested by coating a solution of the drug onto a piece of stainless steel foil (5 cm$^2$). The substrate having a drug film thickness of 2.8 µm was prepared by depositing 1.51 mg of drug. After volatilization of drug from the substrate by charging the capacitors to 14.5 V, 1.37 mg of aerosol particles were recovered from the filter, for a percent yield of 90.9%. The purity of drug compound recovered from the filter was 96.5%. A total mass of 1.51 mg was recovered from the test apparatus and substrate, for a total recovery of 100%.

Example 45

Eletriptan (MW 383, oral dose 3 mg), a serotonin 5-HT receptor agonist used as a migraine preparation, was coated on a piece of stainless steel foil (6 cm$^2$) according to Method B. 1.38 mg of drug was applied to the substrate, for a calculated drug film thickness of 2.2 µm. The substrate was heated as described in Method B by charging the capacitors to 16 V. The purity of the drug-aerosol particles was determined to be 97.8%. 1.28 mg was recovered from the filter after vaporization, for a percent yield of 93%. The total mass was recovered from the test apparatus and substrate, for a total recovery of 100%.

Example 46

Estradiol (MW 272, melting point 179° C., oral dose 2 mg), a hormonal agent, was coated on a piece of aluminum foil (20 cm$^2$) according to Method C. The calculated thickness of the drug film was 1.3 µm. The substrate was heated as described in Method C at 60 V for 9 seconds. The purity of the drug-aerosol particles was determined to be 98.5%. 1.13 mg was recovered from the glass tube walls after vaporization, for a percent yield of 45.2%.

Another substrate containing estradiol was also prepared for testing under argon. On an aluminum foil substrate (20 cm$^2$) 2.6 mg of drug was applied to the substrate, for a calculated thickness of the drug film of 1.3 µm. The substrate was heated as described in Method C at 60 V for 9 seconds. The purity of the drug-aerosol particles was determined to be 98.7%. 1.68 mg was recovered from the glass tube walls after vaporization, for a percent yield of 64.6%.

Example 47

Estradiol-3,17-diacetate (MW 357, oral dose 2 mg), a hormonal prodrug, was coated on a piece of aluminum foil (20 cm$^2$) according to Method C. The calculated thickness of the drug film was 0.9 µm. The substrate was heated as described in Method C at 60 V for 7 seconds. The purity of the drug-aerosol particles was determined to be 96.9%. 1.07 mg was recovered from the glass tube walls after vaporization, for a percent yield of 62.9%.

Example 48

Efavirenz (MW 316, melting point 141° C., oral dose 600 mg), an anti-infective agent, was coated on a stainless steel cylinder (8 cm$^2$) according to Method D. 0.82 mg of drug was applied to the substrate, for a calculated drug film thickness of 1 µm. The substrate was heated as described in Method D by charging the capacitors to 20.5 V. The purity of the drug-aerosol particles was determined to be 97.9%. 0.52 mg was recovered from the filter after vaporization, for a percent yield of 63.4%. A total mass of 0.6 mg was recovered from the test apparatus and substrate, for a total recovery of 73.2%.

Example 49

Ephedrine (MW 165, melting point 40° C., oral dose 10 mg), a respiratory agent, was coated on an aluminum foil substrate (20 cm$^2$) according to Method C. 8.0 mg of drug was applied to the substrate, for a calculated thickness of the drug film of 4.0 µm. The substrate was heated as described in Method C at 90 V for 5 seconds. The purity of the drug-aerosol particles was determined to be 99%. 7.26 mg was recovered from the glass tube walls after vaporization, for a percent yield of 90.8%.

Example 50

Esmolol (MW 295, melting point 50° C., oral dose 35 mg), a cardiovascular agent, was coated on a piece of aluminum foil (20 cm$^2$) according to Method C. The calculated thickness of the drug film was 4.9 µm. The substrate was heated as described in Method C at 90 V for 5 seconds. The purity of the drug-aerosol particles was determined to be 95.8%. 6.4 mg was recovered from the glass tube walls after vaporization, for a percent yield of 65.3%.

Esmolol was coated on a stainless steel cylinder (8 cm$^2$) according to Method D. 0 83 mg of drug was applied to the substrate, for a calculated drug film thickness of 1.4 µm. The substrate was heated as described in Method D by charging the capacitors to 20.5 V. The purity of the drug-aerosol particles was determined to be 93%. 0.63 mg was recovered from the filter after vaporization, for a percent yield of 75.9%. A total mass of 0.81 mg was recovered from the test apparatus and substrate, for a total recovery of 97.6%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 60 milliseconds. Generation of the thermal vapor was complete by 75 milliseconds.

Example 51

Estazolam (MW 295, melting point 229° C., oral dose 2 mg), a sedative and hypnotic, was coated on an aluminum foil substrate (20 cm$^2$) according to Method C. 2.0 mg of drug was applied to the substrate, for a calculated thickness of the drug film of 1.0 μm. The substrate was heated basically as described in Method C at 60 V for 3 seconds then 45 V for 11 seconds. The purity of the drug-aerosol particles was determined to be 99.9%. 1.4 mg was recovered from the glass tube walls after vaporization, for a percent yield of 70%.

Example 52

Ethacrynic acid (MW 303, melting point 122° C., oral dose 25.0 mg), a cardiovascular agent, was coated on a stainless steel cylinder (8 cm$^2$) according to Method E. 1.10 mg of drug was applied to the substrate, for a calculated drug film thickness of 1.3 μm. The substrate was heated as described in Method E and purity of the drug-aerosol particles was determined to be 99.8%. 0.85 mg was recovered from the filter after vaporization, for a percent yield of 77.3%. A total mass of 1.1 mg was recovered from the test apparatus and substrate, for a total recovery of 100%.

Example 53

Ethambutol (MW 204, melting point 89° C., oral dose 1000 mg), a anti-infective agent, was coated on a stainless steel cylinder (8 cm$^2$) according to Method D. 0.85 mg of drug was applied to the substrate, for a calculated drug film thickness of 1 μm. The substrate was heated as described in Method D by charging the capacitors to 20.5 V. The purity of the drug-aerosol particles was determined to be 90%. 0.50 mg was recovered from the filter after vaporization, for a percent yield of 58.8%. A total mass of 0.85 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 50 milliseconds. Generation of the thermal vapor was complete by 90 milliseconds.

Example 54

Fluticasone propionate (MW 501, melting point 272° C., oral dose 0.04 mg), a respiratory agent, was coated on a piece of stainless steel foil (5 $cm^2$) according to Method B. The calculated thickness of the drug film was 0.6 μm. The substrate was heated as described in Method B by charging the capacitors to 15.5 V. The purity of the drug-aerosol particles was determined to be 91.6%. 0.211 mg was recovered from the filter after vaporization, for a percent yield of 70.1%. A total mass of 0.215 mg was recovered from the test apparatus and substrate, for a total recovery of 71.4%.

Example 55

Fenfluramine (MW 231, melting point 112° C., oral dose 20 mg), an obesity management, was coated on a piece of aluminum foil (20 $cm^2$) according to Method C. 9.2 mg were coated. The calculated thickness of the drug film was 4.6 μm. The substrate was heated as described in Method C at 90 V for 5 seconds. The purity of the drug-aerosol particles was determined to be >99.5%. The total mass was recovered from the glass tube walls after vaporization for a percent yield of ~100%.

Example 56

Fenoprofen (MW 242, melting point <25° C., oral dose 200 mg), an analgesic, was coated on a piece of aluminum foil (20 $cm^2$) according to Method C. The calculated thickness of the drug film was 3.7 μm. The substrate was heated as described in Method C at 60 V for 5 seconds. The purity of the drug-aerosol particles was determined to be 98.7%. 4.98 mg was recovered from the glass tube walls after vaporization, for a percent yield of 67.3%.

Example 57

Fentanyl (MW 336, melting point 84° C., oral dose 0.2 mg), an analgesic, was coated onto ten stainless steel foil substrates (5 $cm^2$) according to Method B. The calculated thickness of the drug film on each substrate ranged from about 0.2 μm to about 3.3 μm. The substrates were heated as described in Method B by charging the capacitors to 14 V. Purity of the drug-aerosol particles from each substrate was determined and the results are shown in FIG. 20.

Fentanyl was also coated on a stainless steel cylinder (8 $cm^2$) according to Method D. 0.29 mg of drug was applied to the substrate, for a calculated drug film thickness of 0.4 μm. The substrate was heated as described in Method D by charging the capacitors to 18 V. The purity of the drug-aerosol particles was determined to be 97.9%. 0.19 mg was recovered from the filter after vaporization, for a percent yield of 64%. A total mass of 0.26 mg was recovered from the test apparatus and substrate, for a total recovery of 89%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 100 milliseconds. Generation of the thermal vapor was complete by 250 milliseconds.

Example 58

Flecainide (MW 414, oral dose 50 mg), a cardiovascular agent, was coated on a stainless steel cylinder (8 $cm^2$) according to Method D. 0.80 mg of drug was applied to the substrate, for a calculated drug film thickness of 1 μm. The substrate was heated as described in Method D by charging the capacitors to 20.5 V. The purity of the drug-aerosol particles was determined to be 99.6%. 0.54 mg was recovered from the filter after vaporization, for a percent yield of 67.5%. A total mass of 0.7 mg was recovered from the test apparatus and substrate, for a total recovery of 90%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 65 milliseconds. Generation of the thermal vapor was complete by 110 milliseconds.

Example 59

Fluconazole (MW 306, melting point 140° C., oral dose 200 mg), an anti-infective agent, was coated on a piece of stainless steel foil (5 cm$^2$) according to Method B. 0.737 mg of drug was applied to the substrate, for a calculated drug film thickness of 1.4 µm. The substrate was heated as described in Method B by charging the capacitors to 15.5 V. The purity of the drug-aerosol particles was determined to be 94.3%. 0.736 mg was recovered from the filter after vaporization, for a percent yield of 99.9%. A total mass of 0.737 mg was recovered from the test apparatus and substrate, for a total recovery of 100%.

Example 60

Flunisolide (MW 435, oral dose 0.25 mg), a respiratory agent, was coated was coated on a stainless steel cylinder (8 cm$^2$) according to Method E. 0.49 mg of drug was applied to the substrate, for a calculated drug film thickness of 0.6 µm. The substrate was heated as described in Method E and purity of the drug-aerosol particles was determined to be 97.6%. 0.3 mg was recovered from the filter after vaporization, for a percent yield of 61.2%. A total mass of 0.49 mg was recovered from the test apparatus and substrate, for a total recovery of 100%.

Another substrate (stainless steel foil, 5 cm$^2$) was prepared by applying 0.302 mg drug to form a film having a thickness of 0.6 µm. The substrate was heated as described in Method B by charging the capacitor to 15.0 V. The purity of the drug-aerosol particles was determined to be 94.9%. 0.296 mg was recovered from the filter after vaporization, for a percent yield of 98%. A total mass of 0.302 mg was recovered from the test apparatus and substrate, for a total recovery of 100%.

Example 61

Flunitrazepam (MW 313, melting point 167° C., oral dose 0.5 mg), a sedative and hypnotic, was coated on a piece of aluminum foil (24.5 cm$^2$) according to Method G. The calculated thickness of the drug film was 0.6 µm. The substrate was heated as described in Method G at 90 V for 6 seconds. The purity of the drug-aerosol particles was determined to be 99.8%. 0.73 mg was recovered from the glass tube walls after vaporization, for a percent yield of 60.8%.

Flunitrazepam was further coated on an aluminum foil substrate (24 cm$^2$) according to Method C. 5 mg of the drug was applied to the substrate, for a calculated thickness of the drug film of 2.08 µm. The substrate was heated substantially as described in Method C at 60 V for 7 seconds. The purity of the drug-aerosol particles was determined to be at least 99.9%.

Example 62

Fluoxetine (MW 309, oral dose 20 mg), a psychotherapeutic agent, was coated on an aluminum foil substrate (20 cm$^2$) according to Method C. 1.90 mg of drug was applied to the substrate, for a calculated thickness of the drug film of 1.0 µm. The substrate was heated as described in Method C at 90 V for 3.5 seconds. The purity of the drug-aerosol particles was determined to be 97.4%. 1.4 mg was recovered from the glass tube walls after vaporization, for a percent yield of 73.7%.

Another substrate containing fluoxetine coated (2.0 mg drug) to a film thickness of 1.0 µm was prepared by the same method and heated under an argon atmosphere at 90 V for 3.5 seconds. The purity of the drug-aerosol particles was determined to be 96.8%. 1.7 mg was recovered from the glass tube walls after vaporization, for a percent yield of 85.0%.

Example 63

Galanthamine (MW 287, oral dose 4 mg) was coated on a stainless steel cylinder (8 cm$^2$) according to Method D. 1.4 mg of drug was applied to the substrate, for a calculated drug film thickness of 1.7 µm. The substrate was heated as described in Method D by charging the capacitors to 20.5 V. The purity of the drug-aerosol particles was determined to be >99.5%. 1.16 mg was recovered from the filter after vaporization, for a percent yield of 82.6%. A total mass of 1.39 mg was recovered from the test apparatus and substrate, for a total recovery of 99.1%.

Example 64

Granisetron (MW 312, oral dose 1 mg), a gastrointestinal agent, was coated on an aluminum foil substrate (20 cm$^2$) according to Method C. 1.50 mg of drug was applied to the substrate, for a calculated thickness of the drug film of 0.8 µm. The substrate was heated as described in Method C at 30 V for 45 seconds. The purity of the drug-aerosol particles was determined to be 99%. 1.3 mg was recovered from the glass tube walls after vaporization, for a percent yield of 86.7%.

1.10 mg of granisetron was also coated on an aluminum foil substrate (24.5 cm$^2$) to a calculated drug film thickness of 0.45 µm. The substrate was heated substantially as described in Method G at 90 V for 6 seconds. The purity of the drug-aerosol particles was determined to be 93%. 0.4 mg was recovered from the glass tube walls, for a percent yield of 36%.

Example 65

Haloperidol (MW 376, melting point 149° C., oral dose 2 mg), a psychotherapeutic agent, was coated on an aluminum foil substrate (20 cm$^2$) according to Method C. 2.20 mg of drug was applied to the substrate, for a calculated thickness of the drug film of 1.1 µm. The substrate was heated as described in Method C at 108 V for 2.25 seconds. The purity of the drug-aerosol particles was determined to be 99.8%. 0.6 mg was recovered from the glass tube walls after vaporization, for a percent yield of 27.3%.

Haloperidol was further coated on an aluminum foil substrate according to Method C. The substrate was heated as described in Method C. When 2.1 mg of the drug was heated at 90 V for 3.5 seconds, the purity of the resultant drug-aerosol particles was determined to be 96%. 1.69 mg of aerosol particles were collected for a percent yield of the aerosol of 60%. When 2.1 mg of drug was used and the system was flushed with argon prior to volatilization, the purity of the drug-aerosol particles was determined to be 97%. The percent yield of the aerosol was 29%.

Example 66

Hydromorphone (MW 285, melting point 267° C., oral dose 2 mg), an analgesic, was coated on a stainless steel cylinder (9 cm$^2$) according to Method D. 5.62 mg of drug was applied to the substrate, for a calculated drug film thickness of 6.4 µm. The substrate was heated as described in Method D by charging the capacitors to 19 V. The purity of the drug-aerosol particles was determined to be 99.4%. 2.34 mg was recovered from the filter after vaporization, for a percent yield of 41.6%. A total mass of 5.186 mg was recovered from the test apparatus and substrate, for a total recovery of 92.3%.

Hydromorphone was also coated on a piece of aluminum foil (20 cm$^2$) according to Method C. The calculated thickness of the drug film was 1.1 µm. The substrate was heated as described in Method C at 90 V for 3.5 seconds. The purity of the drug-aerosol particles was determined to be 98.3%. 0.85 mg was recovered from the glass tube walls after vaporization, for a percent yield of 40.5%.

Figure 8:
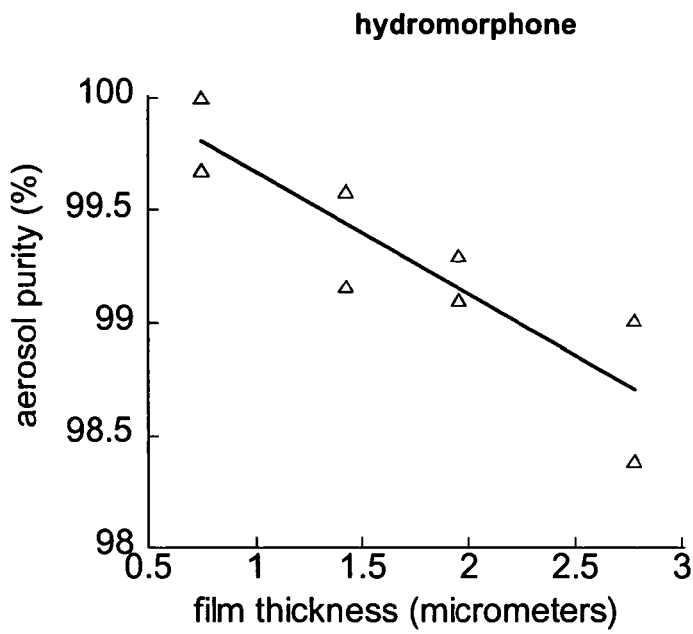

Hydromorphone was also coated onto eight stainless steel cylinder substrates (8 cm$^2$) according to Method D. The calculated thickness of the drug film on each substrate ranged from about 0.7 µm to about 2.8 µm. The substrates were heated as described in Method D by charging the capacitors to 20.5 V. The purity of the drug-aerosol particles determined. The results are shown in FIG. 8. For the substrate having a drug film thickness of 1.4 µm, 1.22 mg of drug was applied to the substrate. After vaporization of this substrate, 0.77 mg was recovered from the filter, for a percent yield of 63.21%. The purity of the drug-aerosol particles was determined to be 99.6%. A total mass of 1.05 mg was recovered from the test apparatus and substrate, for a total recovery of 86.1%.

Example 67

Hydroxychloroquine (MW 336, melting point 91° C., oral dose 400 mg), an antirheumatic agent, was coated on a stainless steel cylinder (8 cm$^2$) according to Method D. 6.58 mg of drug was applied to the substrate, for a calculated drug film thickness of 11 µm. The substrate was heated as described in Method D by charging the capacitors to 20.5 V. The purity of the drug-aerosol particles was determined to be 98.9%. 3.48 mg was recovered from the filter after vaporization, for a percent yield of 52.9%. A total mass of 5.1 mg was recovered from the test apparatus and substrate, for a total recovery of 77.8%.

Example 68

Hyoscyamine (MW 289, melting point 109° C., oral dose 0.38 mg), a gastrointestinal agent, was coated on a piece of aluminum foil (20 cm$^2$) according to Method C. The calculated thickness of the drug film was 0.9 µm. The substrate was heated as described in Method C at 60 V for 8 seconds. The purity of the drug-aerosol particles was determined to be 95.9%. 0.86 mg was recovered from the glass tube walls after vaporization, for a percent yield of 50.6%.

Example 69

Ibuprofen (MW 206, melting point 77° C., oral dose 200 mg), an analgesic, was coated on an aluminum foil substrate (20 cm$^2$) according to Method C. 10.20 mg of drug was applied to the substrate, for a calculated thickness of the drug film of 5.1 µm. The substrate was heated as described in Method C at 60 V for 5 seconds. The purity of the drug-aerosol particles was determined to be 99.7%. 5.45 mg was recovered from the glass tube walls after vaporization, for a percent yield of 53.4%.

Example 70

Imipramine (MW 280, melting point <25° C., oral dose 50 mg), a psycho-therapeutic agent, was coated on a piece of aluminum foil (20 cm$^2$) according to Method C. 1.8 mg was coated on the aluminum foil. The calculated thickness of the drug film was 0.9 µm. The substrate was heated as described in Method C at 90 V for 3.5 seconds. The purity of the drug-aerosol particles was determined to be 98.3%. The total mass recovered from the glass tube walls after vaporization was ~100%.

Another substrate containing imipramine coated to a film thickness of 0.9 µm was prepared by the same method and heated under an argon atmosphere at 90 V for 3.5 seconds. The purity of the drug-aerosol particles was determined to be 99.1%. 1.5 mg was recovered from the glass tube walls after vaporization, for a percent yield of 83.3%.

Example 71

Indomethacin (MW 358, melting point 155° C., oral dose 25 mg), an analgesic, was coated on a piece of aluminum foil (20 cm$^2$) according to Method C. The calculated thickness of the drug film was 1.2 µm. The substrate was heated as described in Method C at 60 V for 6 seconds. The purity of the drug-aerosol particles was determined to be 96.8%. 1.39 mg was recovered from the glass tube walls after vaporization, for a percent yield of 60.4%.

Another substrate containing indomethacin coated to a film thickness of 1.5 µm was prepared by the same method and heated under an argon atmosphere at 60 V for 6 seconds. The purity of the drug-aerosol particles was determined to be 99%. 0.61 mg was recovered from the glass tube walls after vaporization, for a percent yield of 20.3%.

Example 72

Indomethacin ethyl ester (MW 386, oral dose 25 mg), an analgesic, was coated on a piece of aluminum foil (20 cm$^2$) according to Method C. The calculated thickness of the drug film was 2.6 µm. The substrate was heated as described in Method C at 60 V for 9 seconds. The purity of the drug-aerosol particles was determined to be 99%. 2.23 mg was recovered from the glass tube walls after vaporization, for a percent yield of 42.9%.

Another substrate containing indomethacin ethyl ester coated to a film thickness of 2.6 µm was prepared by the same method and heated under an argon atmosphere at 60 V for 9 seconds. The purity of the drug-aerosol particles was determined to be 99%. 3.09 mg was recovered from the glass tube walls after vaporization, for a percent yield of 59.4%.

Example 73

Indomethacin methyl ester (MW 372, oral dose 25 mg), an analgesic, was coated on a piece of aluminum foil (20 cm$^2$) according to Method C. The calculated thickness of the drug film was 2.1 µm. The substrate was heated as described in Method C at 60 V for 6 seconds. The purity of the drug-aerosol particles was determined to be 99%. 1.14 mg was recovered from the glass tube walls after vaporization, for a percent yield of 27.1%.

Another substrate containing indomethacin methyl ester coated to a film thickness of 1.2 µm was prepared by the same method and heated under an argon atmosphere at 60 V for 6 seconds. The purity of the drug-aerosol particles was determined to be 99%. 1.44 mg was recovered from the glass tube walls after vaporization, for a percent yield of 60%.

Example 74

Isocarboxazid (MW 231, melting point 106° C., oral dose 10 mg), a psychotherapeutic agent, was coated on a stainless steel cylinder (8 cm$^2$) according to Method D. 0.97 mg of drug was applied to the substrate, for a calculated drug film thickness of 1.2 µm. The substrate was heated as described in Method D by charging the capacitors to 20.5 V. The purity of the drug-aerosol particles was determined to be 99.6%. 0.52 mg was recovered from the filter after vaporization, for a percent yield of 53%. A total mass of 0.85 mg was recovered from the test apparatus and substrate, for a total recovery of 87.7%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 70 milliseconds. Generation of the thermal vapor was complete by 200 milliseconds.

Example 75

Isotretinoin (MW 300, melting point 175° C., oral dose 35 mg), a skin and mucous membrane agent, was coated on a stainless steel cylinder (8 cm$^2$) according to Method D. 1.11 mg of drug was applied to the substrate, for a calculated drug film thickness of 1.4 µm. The substrate was heated as described in Method D by charging the capacitors to 20.5 V. The purity of the drug-aerosol particles was determined to be 96.6%. 0.66 mg was recovered from the filter after vaporization, for a percent yield of 59.5%. A total mass of 0.86 mg was recovered from the test apparatus and substrate, for a total recovery of 77.5%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 65 milliseconds. Generation of the thermal vapor was complete by 110 milliseconds.

Example 76

Ketamine (MW 238, melting point 93° C., IV dose 100 mg), an anesthetic, was coated on a stainless steel cylinder (8 cm$^2$) according to Method D. 0.836 mg of drug was applied to the substrate, for a calculated drug film thickness of 1.0 µm. The substrate was heated as described in Method D by charging the capacitors to 20.5 V. The purity of the drug-aerosol particles was determined to be 99.9%. 0.457 mg was recovered from the filter after vaporization, for a percent yield of 54.7%. A total mass of 0.712 mg was recovered from the test apparatus and substrate, for a total recovery of 85.2%. High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 75 milliseconds. Generation of the thermal vapor was complete by 100 milliseconds.

Example 77

Ketoprofen (MW 254, melting point 94° C., oral dose 25 mg), an analgesic, was coated on an aluminum foil substrate (20 cm$^2$) according to Method C. 10.20 mg of drug was applied to the substrate, for a calculated thickness of the drug film of 5.1 µm. The substrate was heated as described in Method C at 60 V for 16 seconds. The purity of the drug-aerosol particles was determined to be 98%. 7.24 mg was recovered from the glass tube walls after vaporization, for a percent yield of 71%.

Example 78

Ketoprofen ethyl ester (MW 282, oral dose 25 mg), an analgesic, was coated on a piece of aluminum foil (20 cm$^2$) according to Method C. The calculated thickness of the drug film was 2.0 µm. The substrate was heated as described in Method C at 60 V for 8 seconds. The purity of the drug-aerosol particles was determined to be 99%. 3.52 mg was recovered from the glass tube walls after vaporization, for a percent yield of 88%.

Another substrate containing ketroprofen ethyl ester coated to a film thickness of 2.7 µm was prepared by the same method and heated under an argon atmosphere at 60 V for 8 seconds. The purity of the drug-aerosol particles was determined to be 99.6%. 4.1 mg was recovered from the glass tube walls after vaporization, for a percent yield of 77.4%.

Example 79

Ketoprofen Methyl Ester (MW 268, oral dose 25 mg), an analgesic, was coated on a piece of aluminum foil (20 cm$^2$) according to Method C. The calculated thickness of the drug film was 2.0 µm. The substrate was heated as described in Method C at 60 V for 8 seconds purity of the drug-aerosol particles was determined to be 99%. 2.25 mg was recovered from the glass tube walls after vaporization, for a percent yield of 56.3%.

Another substrate containing ketoprofen methyl ester coated to a film thickness of 3.0 µm was prepared by the same method and heated under an argon atmosphere at 60 V for 8 seconds. The purity of the drug-aerosol particles was determined to be 99%. 4.4 mg was recovered from the glass tube walls after vaporization, for a percent yield of 73.3%.

Example 80

Ketorolac ethyl ester (MW 283, oral dose 10 mg), an analgesic, was coated on an aluminum foil substrate (20 cm$^2$) according to Method C. 9.20 mg of drug was applied to the substrate, for a calculated thickness of the drug film of 4.6 µm. The substrate was heated as described in Method C at 60 V for 12 seconds. The purity of the drug-aerosol particles was determined to be 99%. 5.19 mg was recovered from the glass tube walls after vaporization, for a percent yield of 56.4%.

Example 81

Ketorolac methyl ester (MW 269, oral dose 10 mg) was also coated on an aluminum foil substrate (20 cm$^2$) to a drug film thickness of 2.4 µm (4.8 mg drug applied). The substrate was heated as described in Method C at 60 V for 6 seconds. The purity of the drug-aerosol particles was determined to be 98.8%. 3.17 mg was recovered from the glass tube walls after vaporization, for a percent yield of 66.0%.

Example 82

Ketotifen (MW 309, melting point 152° C., used as 0.025% solution in the eye) was coated on a stainless steel cylinder (8 cm$^2$) according to Method D. 0.544 mg of drug was applied to the substrate, for a calculated drug film thickness of 0.7 µm. The substrate was heated as described in Method D by charging the capacitors to 20.5 V. The purity of the drug-aerosol particles was determined to be 99.9%. 0.435 mg was recovered from the filter after vaporization, for a percent yield of 80%. A total mass of 0.544 mg was recovered from the test apparatus and substrate, for a total recovery of 100%.

Example 83

Lamotrigine (MW 256, melting point 218° C., oral dose 150 mg), an anticonvulsant, was coated on a stainless steel cylinder (8 cm$^2$) according to Method D. 0.93 mg of drug was applied to the substrate, for a calculated drug film thickness of 1.1 µm. The substrate was heated as described in Method D by charging the capacitors to 20.5 V. The purity of the drug-aerosol particles was determined to be 99.1%. 0.58 mg was recovered from the filter after vaporization, for a percent yield of 62.4%. A total mass of 0.93 mg was recovered from the test apparatus and substrate, for a total recovery of 100%.

Example 84

Lidocaine (MW 234, melting point 69° C., oral dose 30 mg), an anesthetic, was coated on an aluminum foil substrate (20 cm$^2$) according to Method C. 9.50 mg of drug was applied to the substrate, for a calculated thickness of the drug film of 4.8 μm. The substrate was heated as described in Method C at 90 V for 5 seconds. The purity of the drug-aerosol particles was determined to be 99.8%. 7.3 mg was recovered from the glass tube walls after vaporization, for a percent yield of 76.8%.

Lidocaine was further coated on an aluminum foil substrate (24.5 $cm^2$) according to Method G. 10.4 mg of the drug was applied to the substrate, for a calculated thickness of the drug film of 4.24 μm. The substrate was heated as described in Method G at 90 V for 6 seconds. The purity of the drug-aerosol particles was determined to be >99%. 10.2 mg of the drug was found to have aerosolized, for a percent yield of 98%.

Example 85

Linezolid (MW 337, melting point 183° C., oral dose 600 mg), an anti-infective agent, was coated on a stainless steel cylinder (8 $cm^2$) according to Method D. 1.09 mg of drug was applied to the substrate, for a calculated drug film thickness of 1.3 μm. The substrate was heated as described in Method D by charging the capacitors to 20.5 V. The purity of the drug-aerosol particles was determined to be 95%. 0.70 mg was recovered from the filter after vaporization, for a percent yield of 64.2%. A total mass of 1.09 mg was recovered from the test apparatus and substrate, for a total recovery of 100%.

Example 86

Loperamide (MW 477, oral dose 4 mg), a gastrointestinal agent, was coated on a stainless steel cylinder (9 $cm^2$) according to Method D. 1.57 mg of drug was applied to the substrate, for a calculated drug film thickness of 1.8 μm. The substrate was heated as described in Method D by charging the capacitors to 20.5 V. The purity of the drug-aerosol particles was determined to be 99.4%. 0.871 mg was recovered from the filter after vaporization, for a percent yield of 55.5%. A total mass of 1.57 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 80 milliseconds. Generation of the thermal vapor was complete by 165 milliseconds.

Example 87

Loratadine (MW 383, melting point 136° C., oral dose 10 mg), an antihistamine, was coated on an aluminum foil substrate (20 $cm^2$) according to Method C. 5.80 mg of drug was applied to the substrate, for a calculated thickness of the drug film of 2.9 μm. The substrate was heated as described in Method C at 60 V for 9 seconds. The purity of the drug-aerosol particles was determined to be 99%. 3.5 mg was recovered from the glass tube walls after vaporization, for a percent yield of 60.3%.

Another substrate containing loratadine coated (6.60 mg drug) to a film thickness of 3.3 μm was prepared by the same method and heated under an argon atmosphere at 60 V for 9 seconds. The purity of the drug-aerosol particles was determined to be 99.6%. 4.5 mg was recovered from the glass tube walls after vaporization, for a percent yield of 68.2%.

Loratadine was further coated on an aluminum foil substrate (24.5 $cm^2$) according to Method G. 10.4 mg of the drug was applied to the substrate, for a calculated thickness of the drug film of 4.24 μm. The substrate was heated substantially as described in Method G at 90 V for 6 seconds, except that two of the openings of the T-shaped tube were left open and the third connected to the 1 L flask. The purity of the drug-aerosol particles was determined to be >99%. 3.8 mg of the drug was found to have aerosolized, for a percent yield of 36.5%.

Example 88

Lovastatin (MW 405, melting point 175° C., oral dose 20 mg), a cardiovascular agent, was coated on a stainless steel cylinder (8 $cm^2$) according to Method D. 0.71 mg of drug was applied to the substrate, for a calculated drug film thickness of 0.9 μm. The substrate was heated as described in Method D by charging the capacitors to 20.5 V. The purity of the drug-aerosol particles was determined to be 94.1%. 0.43 mg was recovered from the filter after vaporization, for a percent yield of 60.6%. A total mass of 0.63 mg was recovered from the test apparatus and substrate, for a total recovery of 88.7%.

Example 89

Lorazepam N,O-diacetyl (typical inhalation dose 0.5 mg), was coated on a piece of aluminum foil (20 $cm^2$) according to Method C. The calculated thickness of the drug film was 0.5 μm. The substrate was heated as described in Method C at 60 V for 7 seconds. The purity of the drug-aerosol particles was determined to be 90%. 0.87 mg was recovered from the glass tube walls after vaporization, for a percent yield of 87%.

Example 90

Loxapine (MW 328, melting point 110° C., oral dose 30 mg), a psychotherapeutic agent, was coated on a stainless steel cylinder (8 $cm^2$) according to Method D. 7.69 mg of drug was applied to the substrate, for a calculated drug film thickness of 9.2 μm. The substrate was heated as described in Method D by charging the capacitors to 20.5 V. The purity of the drug-aerosol particles was determined to be 99.7%. 3.82 mg was recovered from the filter after vaporization, for a percent yield of 50%. A total mass of 6.89 mg was recovered from the test apparatus and substrate, for a total recovery of 89.6%.

Example 91

Maprotiline (MW 277, melting point 94° C., oral dose 25 mg), a psychotherapeutic agent, was coated on an aluminum foil substrate (20 cm$^2$) according to Method C. 2.0 mg of drug was applied to the substrate, for a calculated thickness of the drug film of 1.0 µm. The substrate was heated as described in Method C at 90 V for 3.5 seconds. The purity of the drug-aerosol particles was determined to be 99.7%. 1.3 mg was recovered from the glass tube walls after vaporization, for a percent yield of 65.0%.

Another substrate containing maprotiline coated to a film thickness of 1.0 µm was prepared by the same method and heated under an argon atmosphere at 90 V for 3.5 seconds. The purity of the drug-aerosol particles was determined to be 99.6%. 1.5 mg was recovered from the glass tube walls after vaporization, for a percent yield of 75%.

Example 92

Meclizine (MW 391, melting point <25° C., oral dose 25 mg), a vertigo agent, was coated on an aluminum foil substrate (20 cm$^2$) according to Method C. 5.20 mg of drug was applied to the substrate, for a calculated thickness of the drug film of 2.6 µm. The substrate was heated as described in Method C at 60 V for 7 seconds. The purity of the drug-aerosol particles was determined to be 90.1%. 3.1 mg was recovered from the glass tube walls after vaporization, for a percent yield of 59.6%.

The same drug coated on an identical substrate (aluminum foil (20 cm$^2$)) to a calculated drug film thickness of 12.5 µm was heated under an argon atmosphere as described in Method C at 60 V for 10 seconds. The purity of the drug-aerosol particles was determined to be 97.3%. 4.81 mg was recovered from the glass tube walls after vaporization, for a percent yield of 19.2%.

The dihydrochloride salt form of the drug was also tested. Meclizine dihydrochloride (MW 464, oral dose 25 mg) was coated on a piece of aluminum foil (20 cm$^2$) according to Method C. 19.4 mg of drug was applied to the substrate, for a calculated thickness of the drug film of 9.7 µm. The substrate was heated as described in Method C at 60 V for 6 seconds. The purity of the drug-aerosol particles was determined to be 75.3%. 0.5 mg was recovered from the glass tube walls after vaporization, for a percent yield of 2.6%.

An identical substrate having a calculated drug film thickness of 11.7 µm was heated under an argon atmosphere at 60 V for 6 seconds. Purity of the drug-aerosol particles was determined to be 70.9%. 0.4 mg was recovered from the glass tube walls after vaporization, for a percent yield of 1.7%.

Example 93

Memantine (MW 179, melting point <25° C., oral dose 20 mg), an antiparkinsonian agent, was coated on a stainless steel cylinder (8 cm$^2$) according to Method D. The calculated thickness of the drug film was 1.7 µm. The substrate was heated as described in Method D by charging the capacitors to 20.5 V. The purity of the drug-aerosol particles determined by LC/MS was >99.5%. 0.008 mg was recovered from the glass tube walls after vaporization, for a percent yield of 0.6%. The total mass recovered was 0.06 mg, for a total recovery yield of 4.5%. The amount of drug trapped on the filter was low, most of the aerosol particles escaped into the vacuum line.

Example 94

Meperidine (MW 247, oral dose 50 mg), an analgesic, was coated on an aluminum foil substrate (20 cm$^2$) according to Method C. 1.8 mg of drug was applied to the substrate, for a calculated thickness of the drug film of 0.9 µm. The substrate was heated as described in Method C at 90 V for 3.5 seconds. The purity of the drug-aerosol particles was determined to be 98.8%. 0.95 mg was recovered from the glass tube walls after vaporization, for a percent yield of 52.8%.

Another substrate containing meperidine coated to a film thickness of 1.1 µm was prepared by the same method and heated under an argon atmosphere at 90 V for 3.5 seconds. The purity of the drug-aerosol particles was determined to be 99.9%. 1.02 mg was recovered from the glass tube walls after vaporization, for a percent yield of 48.6%.

Example 95

Metaproterenol (MW 211, melting point 100° C., oral dose 1.3 mg), a respiratory agent, was coated on a stainless steel cylinder (8 cm$^2$) according to Method D. 1.35 mg of drug was applied to the substrate, for a calculated drug film thickness of 1.6 µm. The substrate was heated as described in Method D by charging the capacitors to 20.5 V. The purity of the drug-aerosol particles was determined to be 99.1%. 0.81 mg was recovered from the filter after vaporization, for a percent yield of 60%. A total mass of 1.2 mg was recovered from the test apparatus and substrate, for a total recovery of 88.9%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 150 milliseconds. Generation of the thermal vapor was complete by 300 milliseconds.

Example 96

Methadone (MW 309, melting point 78° C., oral dose 2.5 mg), an analgesic, was coated on an aluminum foil substrate (20 cm$^2$) according to Method C. 1.80 mg of drug was applied to the substrate, for a calculated thickness of the drug film of 0.9 µm. The substrate was heated as described in Method C at 90 V for 3.5 seconds. The purity of the drug-aerosol particles was determined to be 92.3%. 1.53 mg was recovered from the glass tube walls after vaporization, for a percent yield of 85%.

Example 97

Methoxsalen (MW 216, melting point 148° C., oral dose 35 mg), a skin and mucous membrane agent, was coated on a stainless steel cylinder (8 cm$^2$) according to Method D. 1.03 mg of drug was applied to the substrate, for a calculated drug film thickness of 1.2 µm. The substrate was heated as described in Method D by charging the capacitors to 20.5 V. The purity of the drug-aerosol particles was determined to be 99.6%. 0.77 mg was recovered from the filter after vaporization, for a percent yield of 74.8%. A total mass of 1.03 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 80 milliseconds. Generation of the thermal vapor was complete by 135 milliseconds.

Example 98

Metoprolol (MW 267, oral dose 15 mg), a cardiovascular agent, was coated on an aluminum foil substrate (20 cm²) according to Method C. 10.8 mg of drug was applied to the substrate, for a calculated thickness of the drug film of 5.4 μm. The substrate was heated as described in Method C at 90 V for 5 seconds. The purity of the drug-aerosol particles was determined to be 99.2%. 6.7 mg was recovered from the glass tube walls after vaporization, for a percent yield of 62.0%.

Metoprolol was further coated on an aluminum foil substrate (24.5 $cm^2$) according to Method G. 12.7 mg of the drug was applied to the substrate, for a calculated thickness of the drug film of 5.18 μm. The substrate was heated as described in Method G at 90 V for 6 seconds. The purity of the drug-aerosol particles was determined to be >99%. All of the drug was found to have aerosolized, for a percent yield of 100%.

Example 99

Mexiletine HCl (MW 216, melting point 205° C., oral dose 200 mg), a cardiovascular agent, was coated on a stainless steel cylinder (8 $cm^2$) according to Method D. 0.75 mg of drug was applied to the substrate, for a calculated drug film thickness of 0.9 μm. The substrate was heated as described in Method D by charging the capacitors to 20.5 V. The purity of the drug-aerosol particles was determined to be 99.4%. 0.44 mg was recovered from the filter after vaporization, for a percent yield of 58.7%. A total mass of 0.75 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 75 milliseconds. Generation of the thermal vapor was complete by 200 milliseconds.

Example 100

Midazolam (MW 326, melting point 160° C., oral dose 2.5 mg), a sedative and hypnotic, was coated onto five stainless steel cylindrical substrates according to Method E. The calculated thickness of the drug film on each substrate ranged from about 1.1 μm to about 5.8 μm. The substrates were heated as described in Method E and purity of the drug-aerosol particles determined. The results are shown in FIG. 12.

Another substrate (stainless steel cylindrical, 6 $cm^2$) was prepared by depositing 5.37 mg drug to obtain a drug film thickness of 9 μm. After volatilization of drug from this substrate according to Method E, 3.11 mg was recovered from the filter, for a percent yield of 57.9%. A total mass of 5.06 mg was recovered from the test apparatus and substrate, for a total recovery of 94.2%. Purity of the drug aerosol particles was 99.5%. The yield of aerosol particles was 57.9%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 130 milliseconds. Generation of the thermal vapor was complete by 240 milliseconds.

Midazolam was also coated on an aluminum foil substrate (28.8 $cm^2$) according to Method C. 5.0 mg of the drug was applied to the substrate, for a calculated thickness of the drug film of 1.74 μm. The substrate was heated substantially as described in Method C at 60 V for 6 seconds. The purity of the drug-aerosol particles was determined to be 99.9%.

Another aluminum foil substrate (36 $cm^2$) was prepared essentially according to Method G. 16.7 mg of midazolam was applied to the substrate, for a calculated thickness of the drug film of 4.64 μm. The substrate was heated substantially as described in Method G at 90 V for 6 seconds, except that one of the openings of the T-shaped tube was sealed with a rubber stopper, one was loosely covered with the end of the halogen tube, and the third connected to the 1 L flask. The purity of the drug-aerosol particles was determined to be >99%. All of the drug was found to have aerosolized, for a percent yield of 100%.

Example 101

Mirtazapine (MW 265, melting point 116° C., oral dose 10 mg), a psychotherapeutic agent used as an antidepressant, was coated on an aluminum foil substrate (24.5 $cm^2$) according to Method G. 20.7 mg of drug was applied to the substrate, for a calculated thickness of the drug film of 8.4 μm. The substrate was heated as described in Method G at 90 V for 6 seconds. The purity of the drug-aerosol particles was determined to be 99%. 10.65 mg was recovered from the glass tube walls after vaporization, for a percent yield of 51.4%.

Example 102

Morphine (MW 285, melting point 197° C., oral dose 15 mg), an analgesic, was coated on a stainless steel cylinder (8 $cm^2$) according to Method D. 2.33 mg of drug was applied to the substrate, for a calculated drug film thickness of 2.8 μm. The substrate was heated as described in Method D by charging the capacitors to 20.5 V. The purity of the drug-aerosol particles was determined to be 99.1%. 1.44 mg was recovered from the filter after vaporization, for a percent yield of 61.8%. A total mass of 2.2 mg was recovered from the test apparatus and substrate, for a total recovery of 94.2%.

Morphine (MW 285, melting point 197° C., oral dose 15 mg), an analgesic, was coated on a piece of aluminum foil (20 $cm^2$) according to Method C. The calculated thickness of the drug film was 4.8 μm. The substrate was heated as described in Method C at 90 V for 5 seconds. The purity of the drug-aerosol particles was determined to be 92.5%. 3.1 mg was recovered from the glass tube walls after vaporization, for a percent yield of 32.3%.

Example 103

Nalbuphine (MW 357, melting point 231° C., oral dose 10 mg), an analgesic, was coated onto four stainless steel cylinder substrates (8 $cm^2$) according to Method D. The calculated thickness of the drug film on each substrate ranged from about 0.7 μm to about 2.5 μm. The substrates were heated as described in Method D by charging the capacitors to 20.5 V. The purity of the drug-aerosol particles from each substrate was determined and the results are shown in FIG. 13. For the substrate having a drug film thickness of 0.7 μm, 0.715 mg of drug was applied to the substrate. After volatilization of this substrate, 0.455 mg was recovered from the filter, for a per-

Example 104

Naloxone (MW 327, melting point 184° C., oral dose 0.4 mg), an antidote, was coated on an aluminum foil (20 cm$^2$) according to Method C. 2.10 mg of drug was applied to the substrate, for a calculated thickness of the drug film of 1.1 μm. The substrate was heated as described in Method C at 90 V for 3.5 seconds. The purity of the drug-aerosol particles was determined to be 78.4%. 1.02 mg was recovered from the glass tube walls after vaporization, for a percent yield of 48.6%.

Another substrate containing naloxone coated to a film thickness of 1.0 μm was prepared by the same method and heated under an argon atmosphere at 90 V for 3.5 seconds. The purity of the drug-aerosol particles was determined to be 99.2%. 1.07 mg was recovered from the glass tube walls after vaporization, for a percent yield of 53.5%.

Example 105

Naproxen (MW 230, melting point 154° C., oral dose 200 mg), an analgesic, was coated on a piece of aluminum foil (20 cm$^2$) according to Method C. 8.7 mg were coated on the foil for a calculated thickness of the drug film of 4.4 μm. The substrate was heated as described in Method C at 60 V for 7 seconds. The purity of the drug-aerosol particles was determined to be >99.5%. 4.4 mg was recovered from the glass tube walls after vaporization, for a percent yield of 50.5%.

Example 106

Naratriptan (MW 335, melting point 171° C., oral dose 1 mg), a migraine preparation, was coated onto seven stainless steel cylinder substrates (8 $cm^2$) according to Method D. The calculated thickness of the drug film on each substrate ranged from about 0.5 μm to about 2.5 μm. The substrates were heated as described in Method D by charging the capacitors to 20.5 V. Purity of the drug-aerosol particles from each substrate was determined and the results are shown in FIG. 14. For the substrate having a drug film thickness of 0.6 μm, 0.464 mg of drug was applied to the substrate. After vaporization of this substrate by charging the capacitors to 20.5 V. 0.268 mg was recovered from the filter, for a percent yield of 57.8%. The purity was determined to be 98.7%. A total mass of 0.464 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 100 milliseconds. Generation of the thermal vapor was complete by 250 milliseconds.

Example 107

Nefazodone (MW 470, melting point 84° C., oral dose 75 mg), a psychotherapeutic agent, was coated on a piece of aluminum foil (20 $cm^2$) according to Method C. The calculated thickness of the drug film was 4.6 μm. The substrate was heated as described in Method C at 60 V for 15 seconds. The purity of the drug-aerosol particles was determined to be 91%. 4.4 mg was recovered from the glass tube walls after vaporization, for a percent yield of 47.8%.

Another substrate containing nefazodone coated to a film thickness of 3.2 μm was prepared by the same method and heated under an argon atmosphere at 60 V for 15 seconds. The purity of the drug-aerosol particles was determined to be 97.5%. 4.3 mg was recovered from the glass tube walls after vaporization, for a percent yield of 68.3%.

Example 108

Nortriptyline (MW 263, oral dose 15 mg), a psychotherapeutic agent, was coated on an aluminum foil substrate (20 $cm^2$) according to Method C. The calculated thickness of the drug film was 1.0 μm. The substrate was heated as described in Method C at 90 V for 3.5 seconds. The purity of the drug-aerosol particles was determined to be 99.1%. 1.4 mg was recovered from the glass tube walls after vaporization, for a percent yield of 70.0%.

Another substrate containing nortriptyline was prepared for testing under an argon atmosphere. 1.90 mg of drug was applied to the substrate, for a calculated thickness of the drug film of 1.0 μm. The substrate was heated as described in Method C at 90 V for 3.5 seconds. The purity of the drug-aerosol particles was determined to be 97.8%. 1.6 mg was recovered from the glass tube walls after vaporization, for a percent yield of 84.2%.

Example 109

Olanzapine (MW 312, melting point 195° C., oral dose 10 mg), a psychotherapeutic agent, was coated onto eight stainless steel cylinder substrates (8-9 $cm^2$) according to Method D. The calculated thickness of the drug film on each substrate ranged from about 1.2 μm to about 7.1 μm. The substrates were heated as described in Method D by charging the capacitors to 20.5 V. Purity of the drug-aerosol particles from each substrate was determined and the results are shown in FIG. 15. The substrate having a thickness of 3.4 μm was prepared by depositing 2.9 mg of drug. After volatilization of drug from this substrate by charging the capacitors to 20.5 V, 1.633 mg was recovered from the filter, for a percent yield of 54.6%. The purity of the drug aerosol recovered from the filter was found to be 99.8%. The total mass was recovered from the test apparatus and substrate, for a total recovery of ~100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 80 milliseconds. Generation of the thermal vapor was complete by 130 milliseconds.

Olanzapine was also coated on an aluminum foil substrate (24.5 $cm^2$) according to Method G. 11.3 mg of drug was applied to the substrate, for a calculated thickness of the drug film of 4.61 μm. The substrate was heated as described in Method G at 90 V for 6 seconds. The purity of the drug-aerosol particles was determined to be >99%. 7.1 mg was collected for a percent yield of 62.8%.

Example 110

Orphenadrine (MW 269, melting point <25° C., oral dose 60 mg), a muscle relaxant, was coated on a piece of aluminum foil (20 $cm^2$) according to Method C. The calculated thickness of the drug film was 1.0 μm. The substrate was heated as described in Method C at 90 V for 3.5 seconds. The purity of the drug-aerosol particles was determined to be >99.5%. 1.35 mg was recovered from the glass tube walls after vaporization, for a percent yield of 71.1%.

Example 111

Oxycodone (MW 315, melting point 220° C., oral dose 5 mg), an analgesic, was coated on an aluminum foil substrate (20 cm$^2$) according to Method C. 2.4 mg of drug was applied to the substrate, for a calculated thickness of the drug film of 1.2 μm. The substrate was heated as described in Method C at 90 V for 3.5 seconds. The purity of the drug-aerosol particles was determined to be 99.9%. 1.27 mg was recovered from the glass tube walls after vaporization, for a percent yield of 52.9%.

Example 112

Oxybutynin (MW 358, oral dose 5 mg), a urinary tract agent, was coated on a piece of aluminum foil (20 cm$^2$) according to Method C. The calculated thickness of the drug film was 2.8 μm. The substrate was heated as described in Method C at 60 V for 6 seconds. The purity of the drug-aerosol particles was determined to be 90.6%. 3.01 mg was recovered from the glass tube walls after vaporization, for a percent yield of 54.7%.

Example 113

Parecoxib (MW 370, oral dose 10 mg), a non-steroidal anti-inflammatory analgesic, was coated on a piece of stainless steel foil (5 cm$^2$) according to Method B. The calculated thickness of the drug film was 6.0 μm. The substrate was heated as described in Method B by charging the capacitors to 15.5 V. The purity of the drug-aerosol particles was determined to be 80%. 1.264 mg was recovered from the filter after vaporization, for a percent yield of 39.5%.

Another substrate (stainless steel foil, 5 cm$^2$) was prepared by applying 0.399 mg drug to form a film having a thickness of 0.8 μm. The substrate was heated as described in Method B by charging the capacitors to 15 V. The purity of the drug-aerosol particles was determined to be 97.2%. 0.323 mg was recovered from the filter after vaporization, for a percent yield of 81.0%. A total mass of 0.324 mg was recovered from the test apparatus and substrate, for a total recovery of 81.3%.

Example 114

Paroxetine (MW 329, oral dose 20 mg), a psychotherapeutic agent, was coated on a stainless steel cylinder (8 cm$^2$) according to Method D. 2.02 mg of drug was applied to the substrate, for a calculated drug film thickness of 2.4 μm. The substrate was heated as described in Method D (with the single exception that the circuit capacitance was 1.5 Farad, not 2.0 Farad), and purity of the drug-aerosol particles was determined to be 99.5%. 1.18 mg was recovered from the filter after vaporization, for a percent yield of 58.4%. A total mass of 1.872 mg was recovered from the test apparatus and substrate, for a total recovery of 92.7%.

Paroxetine was also coated on an aluminum foil substrate (24.5 cm$^2$) as described in Method G. 19.6 mg of drug was applied to the substrate, for a calculated drug film thickness of 8 μm. The substrate was heated as described in Method G at 90 V for 6 seconds purity of the drug-aerosol particles was determined to be 88%. 7.4 mg were lost from the substrate after vaporization, for a percent yield of 37.8%.

Example 115

Pergolide (MW 314, melting point 209° C., oral dose 1 mg), an antiparkinsonian agent, was coated on a stainless steel cylinder (8 cm$^2$) according to Method D. 1.43 mg of drug was applied to the substrate, for a calculated drug film thickness of 1.9 μm. The substrate was heated as described in Method D by charging the capacitors to 20.5 V. The purity of the drug-aerosol particles was determined to be 99.7%. 1.18 mg was recovered from the filter after vaporization, for a percent yield of 82.5%. A total mass of 1.428 mg was recovered from the test apparatus and substrate, for a total recovery of 99.9%.

Pergolide was also coated on a piece of aluminum foil (20 cm$^2$) according to Method C. The calculated thickness of the drug film was 1.2 μm. The substrate was heated as described in Method C at 90 V for 3.5 seconds. The purity of the drug-aerosol particles was determined to be 98%. 0.52 mg was recovered from the glass tube walls after vaporization, for a percent yield of 22.6%.

High speed photographs were taken as the drug-coated substrate according to Method D was heated to monitor visually formation of a thermal vapor. The photographs showed that a thermal vapor was initially visible 30 milliseconds after heating was initiated, with the majority of the thermal vapor formed by 225 milliseconds. Generation of the thermal vapor was complete by 800 milliseconds.

Pergolide was further coated on an aluminum foil substrate (24.5 cm$^2$) according to Method G. 1.0 mg of the drug was applied to the substrate, for a calculated thickness of the drug film of 0.4 μm. The substrate was heated substantially as described in Method G at 90 V for 6 seconds, except that two of the openings of the T-shaped tube were left open and the third connected to the 1 L flask. The purity of the drug-aerosol particles was determined to be >99%. All of the drug was found to have aerosolized via weight loss from the substrate, for a percent yield of 100%.

Example 116

Phenyloin (MW 252, melting point 298° C., oral dose 300 mg), an anti-convulsant, was coated on a stainless steel cylinder (8 cm$^2$) according to Method D. 0.9 mg of drug was applied to the substrate, for a calculated drug film thickness of 1.1 μm. The substrate was heated as described in Method D by charging the capacitors to 20.5 V. The purity of the drug-aerosol particles was determined to be >99.5%. 0.6 mg was recovered from the filter after vaporization, for a percent yield of 66.7%. A total mass of 0.84 mg was recovered from the test apparatus and substrate, for a total recovery of 93.3%.

High speed photographs were taken as the drug-coated substrate was heated to monitor visually formation of a thermal vapor. The photographs, shown in FIGS. 24A-24D, showed that a thermal vapor was initially visible 25 milliseconds after heating was initiated, with the majority of the thermal vapor formed by 90 milliseconds. Generation of the thermal vapor was complete by 225 milliseconds.

Example 117

Pindolol (MW 248, melting point 173° C., oral dose 5 mg), a cardiovascular agent, was coated on an aluminum foil substrate (20 cm$^2$) according to Method C. 4.7 mg of drug was applied to the substrate, for a calculated thickness of the drug film of 2.4 μm. The substrate was heated as described in Method C at 60 V for 7 seconds. The purity of the drug-aerosol particles was determined to be >99.5%. 2.77 mg was recovered from the glass tube walls after vaporization, for a percent yield of 58.9%.

Another substrate containing pindolol coated to a film thickness of 3.3 µm was prepared by the same method and heated under an argon atmosphere at 60 V for 7 seconds. The purity of the drug-aerosol particles was determined to be >99.5%. 3.35 mg was recovered from the glass tube walls after vaporization, for a percent yield of 50.8%.

Example 118

Pioglitazone (MW 356, melting point 184° C., oral dose 15 mg), an antidiabetic agent, was coated on a stainless steel cylinder (8 $cm^2$) according to Method D. 0.48 mg of drug was applied to the substrate, for a calculated drug film thickness of 0.6 μm. The substrate was heated as described in Method D by charging the capacitors to 20.5 V. The purity of the drug-aerosol particles was determined to be 95.6%. 0.30 mg was recovered from the filter after vaporization, for a percent yield of 62.5%. A total mass of 0.37 mg was recovered from the test apparatus and substrate, for a total recovery of 77.1%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 100 milliseconds. Generation of the thermal vapor was complete by 125 milliseconds.

Example 119

Piribedil (MW 298, melting point 98° C., IV dose 3 mg), an antiparkinsonian agent, was coated on a stainless steel cylinder (8 $cm^2$) according to Method D. 1.1 mg of drug was applied to the substrate, for a calculated drug film thickness of 1.5 μm. The substrate was heated as described in Method D by charging the capacitors to 20.5 V. The purity of the drug-aerosol particles was determined to be 99.7%. 1.01 mg was recovered from the filter after vaporization, for a percent yield of 91.8%. A total mass of 1.1 mg was recovered from the test apparatus and substrate, for a total recovery of 100%.

Example 120

Pramipexole (MW 211, oral dose 0.5 mg), an antiparkinsonian agent, was coated on a stainless steel cylinder (8 $cm^2$) according to Method D. 1.05 mg of drug was applied to the substrate, for a calculated drug film thickness of 1.4 μm. The substrate was heated as described in Method D by charging the capacitors to 20.5 V. The purity of the drug-aerosol particles was determined to be 99.3%. 0.949 mg was recovered from the filter after vaporization, for a percent yield of 90.4%. A total mass of 1.05 mg was recovered from the test apparatus and substrate, for a total recovery of 100%.

Pramipexole was also coated on a piece of stainless steel foil (5 $cm^2$) according to Method B. 0.42 mg of drug was applied to the substrate, for a calculated drug film thickness of 0.9 μm. The substrate was heated as described in Method B by charging the capacitors to 14 V. The purity of the drug-aerosol particles was determined to be 98.9%. 0.419 mg was recovered from the filter after vaporization, for a percent yield of 99.8%. A total mass of 0.42 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 80 milliseconds. Generation of the thermal vapor was complete by 140 milliseconds.

Example 121

Procainamide (MW 236, oral dose 125 mg), a cardiovascular agent, was coated on a stainless steel cylinder (8 $cm^2$) according to Method D. 0.95 mg of drug was applied to the substrate, for a calculated drug film thickness of 1.1 μm. The substrate was heated as described in Method D by charging the capacitors to 20.5 V. The purity of the drug-aerosol particles was determined to be >99.5%. 0.56 mg was recovered from the filter after vaporization, for a percent yield of 58.9%. A total mass of 0.77 mg was recovered from the test apparatus and substrate, for a total recovery of 81.1%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 90 milliseconds. Generation of the thermal vapor was complete by 250 milliseconds.

Example 122

Prochlorperazine free base (MW 374, melting point 60° C., oral dose 5 mg), a psychotherapeutic agent, was coated onto four stainless steel foil substrates (5 $cm^2$) according to Method B. The calculated thickness of the drug film on each substrate ranged from about 2.3 μm to about 10.1 μm. The substrates were heated as described in Method B by charging the capacitors to 15 V. Purity of the drug-aerosol particles from each substrate was determined and the results are shown in FIG. 18.

Prochlorperazine, a psychotherapeutic agent, was also coated on a stainless steel cylinder (8 $cm^2$) according to Method D. 1.031 mg of drug was applied to the substrate, for a calculated drug film thickness of 1.0 μm. The substrate was heated as described in Method D by charging the capacitors to 19 V. The purity of the drug-aerosol particles was determined to be 98.7%. 0.592 mg was recovered from the filter after vaporization, for a percent yield of 57.4%. A total mass of 1.031 mg was recovered from the test apparatus and substrate, for a total recovery of 100%.

Example 123

Promazine (MW 284, melting point <25° C., oral dose 25 mg), a psychotherapeutic agent, was coated on a piece of aluminum foil (20 $cm^2$) according to Method C. The calculated thickness of the drug film was 5.3 μm. The substrate was heated as described in Method C at 90 V for 5 seconds. The purity of the drug-aerosol particles was determined to be 94%. 10.45 mg was recovered from the glass tube walls after vaporization, for a percent yield of 99.5%.

Example 124

Promethazine (MW 284, melting point 60° C., oral dose 12.5 mg), a gastrointestinal agent, was coated on an aluminum foil substrate (20 $cm^2$) according to Method C. 5.10 mg of drug was applied to the substrate, for a calculated thickness of the drug film of 2.6 μm. The substrate was heated as described in Method C at 60 V for 10 seconds. The purity of the drug-aerosol particles was determined to be 94.5%. 4.7 mg was recovered from the glass tube walls after vaporization, for a percent yield of 92.2%.

Example 125

Propafenone (MW 341, oral dose 150 mg), a cardiovascular agent, was coated on a stainless steel cylinder (8 cm$^2$) according to Method D. 0.77 mg of drug was applied to the substrate, for a calculated drug film thickness of 0.9 μm. The substrate was heated as described in Method D by charging the capacitors to 20.5 V. The purity of the drug-aerosol particles was determined to be >99.5%. 0.51 mg was recovered from the filter after vaporization, for a percent yield of 66.2%. A total mass of 0.77 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 20 milliseconds after heating was initiated, with the majority of the thermal vapor formed by 60 milliseconds. Generation of the thermal vapor was complete by 110 milliseconds.

Example 126

Propranolol (MW 259, melting point 96° C., oral dose 40 mg), a cardiovascular agent, was coated on an aluminum foil substrate (20 $cm^2$) according to Method C. 10.30 mg of drug was applied to the substrate, for a calculated thickness of the drug film of 5.2 μm. The substrate was heated as described in Method C at 90 V for 5 seconds. The purity of the drug-aerosol particles was determined to be 99.6%. 8.93 mg was recovered from the glass tube walls after vaporization, for a percent yield of 86.7%.

Example 127

Quetiapine (MW 384, oral dose 75 mg), a psychotherapeutic agent, was coated onto eight stainless steel cylinder substrates (8 $cm^2$) according to Method D. The calculated thickness of the drug film on each substrate ranged from about 0.1 μm to about 7.1 μm. The substrates were heated as described in Method D by charging the capacitors to 20.5 V. Purity of the drug-aerosol particles from each substrate was determined and the results are shown in FIG. 16. The substrate having a drug film thickness of 1.8 μm was prepared by depositing 1.46 mg drug. After volatilization of drug this substrate by charging the capacitors to 20.5 V. 0.81 mg was recovered from the filter, for a percent yield of 55.5%. The purity of the drug aerosol recovered from the filter was found to be 99.1%. A total mass of 1.24 mg was recovered from the test apparatus and substrate, for a total recovery of 84.9%.

Example 128

Quinidine (MW 324, melting point 175° C., oral dose 100 mg), a cardiovascular agent, was coated on a stainless steel cylinder (8 $cm^2$) according to Method D. 1.51 mg of drug was applied to the substrate, for a calculated drug film thickness of 1.8 μm. The substrate was heated as described in Method D by charging the capacitors to 20.5 V. The purity of the drug-aerosol particles was determined to be >99.5%. 0.88 mg was recovered from the filter after vaporization, for a percent yield of 58.3%. A total mass of 1.24 mg was recovered from the test apparatus and substrate, for a total recovery of 82.1%.

Example 129

Rizatriptan (MW 269, melting point 121° C., oral dose 5 mg), a migraine preparation, was coated on a stainless steel cylinder (6 $cm^2$) according to Method E. 2.1 mg of drug was applied to the substrate, for a calculated drug film thickness of 3.5 μm. The substrate was heated as described in Method E and purity of the drug-aerosol particles was determined to be 99.2%. 1.66 mg was recovered from the filter after vaporization, for a percent yield of 79%. A total mass of 2.1 mg was recovered from the test apparatus and substrate, for a total recovery of 100%.

Rizatriptan was further coated on an aluminum foil substrate (150 $cm^2$) according to Method F. 10.4 mg of the drug was applied to the substrate, for a calculated thickness of the drug film of 0.7 μm. The substrate was heated as described in Method F at 250° C. and the purity of the drug-aerosol particles was determined to be 99%. 1.9 mg was collected in glass wool for a percent yield of 18.3%.

Another aluminum foil substrate (36 $cm^2$) was prepared according to Method G. 11.6 mg of rizatriptan was applied to the substrate, for a calculated thickness of the drug film of 3.2 μm. The substrate was heated substantially as described in Method G at 90 V for 7 seconds, except that one of the openings of the T-shaped tube was sealed with a rubber stopper, one was loosely covered with the end of the halogen tube, and the third connected to the 1 L flask. The purity of the drug-aerosol particles was determined to be >99%. All of the drug was found to have aerosolized, for a percent yield of 100%.

Example 130

Rofecoxib (MW 314, oral dose 50 mg), an analgesic, was coated on an aluminum foil substrate (20 $cm^2$) according to Method C. 6.5 mg of drug was applied to the substrate, for a calculated thickness of the drug film of 3.3 μm. The substrate was heated as described in Method C at 60 V for 17 seconds. The purity of the drug-aerosol particles was determined to be 97.5%. 4.1 mg was recovered from the glass tube walls after vaporization, for a percent yield of 63.1%.

Example 131

Ropinirole (MW 260, oral dose 0.25 mg), an antiparkinsonian agent, was coated on a stainless steel cylinder (8 $cm^2$) according to Method D. 0.754 mg of drug was applied to the substrate, for a calculated drug film thickness of 1.0 μm. The substrate was heated as described in Method D by charging the capacitors to 20.5 V. The purity of the drug-aerosol particles was determined to be 99%. 0.654 mg was recovered from the filter after vaporization, for a percent yield of 86.7%. A total mass of 0.728 mg was recovered from the test apparatus and substrate, for a total recovery of 96.6%.

Example 132

Sertraline (MW 306, oral dose 25 mg), a psychotherapeutic agent used as an antidepressant (Zoloft®), was coated on a stainless steel cylinder (6 $cm^2$) according to Method E. 3.85 mg of drug was applied to the substrate, for a calculated drug film thickness of 6.4 μm. The substrate was heated as described in Method E and purity of the drug-aerosol particles was determined to be 99.5%. 2.74 mg was recovered from the filter after vaporization, for a percent yield of 71.2%.

Sertraline was also coated on a piece of aluminum foil (20 $cm^2$) according to Method C. The calculated thickness of the drug film was 3.3 μm. The substrate was heated as described in Method C at 60 V for 10 seconds. The purity of the drug-aerosol particles was determined to be 98.0%. 5.35 mg was recovered from the glass tube walls after vaporization, for a percent yield of 81.1%.

Another sertraline coated substrate (aluminum foil, 20 cm²) having a drug film thickness of 0.9 μm was heated as described in Method C under a pure argon atmosphere at 90 V for 3.5 seconds. The purity of the drug-aerosol particles was determined to be 98.7%. 1.29 mg was recovered from the glass tube walls after vaporization, for a percent yield of 75.9%.

High speed photographs were taken as the drug-coated substrate from Method D was heated to monitor visually formation of a thermal vapor. The photographs showed that a thermal vapor was initially visible 30 milliseconds after heating was initiated, with the majority of the thermal vapor formed by 135 milliseconds. Generation of the thermal vapor was complete by 250 milliseconds.

Example 133

Selegiline (MW 187, melting point <25° C., oral dose 5 mg), an antiparkinsonian agent, was coated on an aluminum foil substrate (20 cm²) according to Method C. 3.7 mg of drug was applied to the substrate, for a calculated thickness of the drug film of 1.9 μm. The substrate was heated as described in Method C at 60 V for 8 seconds. The purity of the drug-aerosol particles was determined to be 99.2%. 2.41 mg was recovered from the glass tube walls after vaporization, for a percent yield of 65.1%.

Example 134

Sildenafil (MW 475, melting point 189° C., oral dose 25 mg), an agent used for erectile dysfunction (Viagra®), was coated onto six stainless steel foil substrates (5 cm²) according to Method B. The calculated thickness of the drug film on each substrate ranged from about 0.5 μm to about 1.6 μm. The substrates were heated as described in Method B by charging the capacitors to 16 V. Purity of the drug-aerosol particles from each substrate was determined and the results are shown in FIG. 22.

Sildenafil was also coated on a stainless steel cylinder (6 cm²) according to Method E. 1.9 mg of drug was applied to the substrate, for a calculated drug film thickness of 3.2 μm. The substrate was heated as described in Method E and purity of the drug-aerosol particles was determined to be 81%. 1.22 mg was recovered from the filter after vaporization, for a percent yield of 64.2%. A total mass of 1.5 mg was recovered from the test apparatus and substrate, for a total recovery of 78.6%.

Sildenafil was also coated on a piece of aluminum foil (20 cm²) according to Method C. The calculated thickness of the drug film was 2.5 μm. The substrate was heated as described in Method C at 90 V for 4 seconds. The purity of the drug-aerosol particles was determined to be 66.3%. 1.05 mg was recovered from the glass tube walls after vaporization, for a percent yield of 21%.

Sildenafil was also coated on a piece of stainless steel foil (6 cm²) according to Method B. 0.227 mg of drug was applied to the substrate, for a calculated drug film thickness of 0.4 μm. The substrate was heated as described in Method B by charging the capacitors to 16 V. The purity of the drug-aerosol particles was determined to be 99.3%. 0.224 mg was recovered from the filter after vaporization, for a percent yield of 98.7%. A total mass of 0.227 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 45 milliseconds after heating was initiated, with the majority of the thermal vapor formed by 250 milliseconds. Generation of the thermal vapor was complete by 400 milliseconds.

Sildenafil was also coated on a piece of aluminum foil at a calculated film thickness of 3.4 μm, 3.3 μm, 1.6 μm, 0.8 μm, 0.78 μm, 0.36 μm, 0.34 μm, 0.29 μm, and 0.1 μm. The coated substrate was placed on an aluminum block that was preheated to 275° C. using a hot plate. A Pyrex© beaker was synchronously placed over the foil and the substrate was heated for 1 minute. The material collected on the beaker walls was recovered and analyzed by reverse-phase HPLC analysis with detection by absorption of 250 nm light to determine the purity of the aerosol. The purity of the drug-aerosol particles was determined to be 84.8% purity at 3.4 μm thickness; 80.1% purity at 3.3 μm thickness; 89.8% purity at 1.6 μm thickness; 93.8% purity at 0.8 μm thickness; 91.6% purity at 0.78 μm thickness; 98.0% purity at 0.36 μm thickness; 98.6% purity at 0.34 μm thickness; 97.6% purity at 0.29 μm thickness; and 100% purity at 0.1 μm thickness.

Example 135

Spironolactone (MW 417, melting point 135° C., oral dose 25 mg), a cardiovascular agent, was coated on a stainless steel cylinder (8 cm²) according to Method D. 0.71 mg of drug was applied to the substrate, for a calculated drug film thickness of 0.9 μm. The substrate was heated as described in Method D by charging the capacitors to 20.5 V. The purity of the drug-aerosol particles was determined to be >99.5%. 0.41 mg was recovered from the filter after vaporization, for a percent yield of 57.7%. A total mass of 0.7 mg was recovered from the test apparatus and substrate, for a total recovery of 98.6%.

Example 136

Sumatriptan (MW 295, melting point 171° C., oral dose 6 mg), a migraine preparation, was coated on a stainless steel cylinder (8 cm²) according to Method E. 1.22 mg of drug was applied to the substrate, for a calculated drug film thickness of 1.5 μm. The substrate was heated as described in Method E and purity of the drug-aerosol particles was determined to be 97.9%. 0.613 mg was recovered from the filter after vaporization, for a percent yield of 50.2%. A total mass of 1.03 mg was recovered from the test apparatus and substrate, for a total recovery of 84.4%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 175 milliseconds. Generation of the thermal vapor was complete by 600 milliseconds.

Example 137

Sibutramine (MW 280, oral dose 10 mg), an obesity management appetite suppressant, was coated on a stainless steel cylinder (8 cm²) according to Method D. 1.667 mg of drug was applied to the substrate, for a calculated drug film thickness of 2 μm. The substrate was heated as described in Method D (with the single exception that the circuit capacitance was 1.5 Farad, not 2.0 Farad), and purity of the drug-aerosol particles was determined to be 94%. 0.861 mg was recovered from the filter after vaporization, for a percent yield of 51.6%. A total mass of 1.35 mg was recovered from the test apparatus and substrate, for a total recovery of 81%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 55 milliseconds. Generation of the thermal vapor was complete by 150 milliseconds.

Example 138

Tamoxifen (MW 372, melting point 98° C., oral dose 10 mg), an antineoplastic, was coated on a stainless steel cylinder (8 cm$^2$) according to Method D. 0.46 mg of drug was applied to the substrate, for a calculated drug film thickness of 0.6 µm. The substrate was heated as described in Method D by charging the capacitors to 20.5 V. The purity of the drug-aerosol particles was determined to be 91.4%. 0.27 mg was recovered from the filter after vaporization, for a percent yield of 58.7%. A total mass of 0.39 mg was recovered from the test apparatus and substrate, for a total recovery of 84.8%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 70 milliseconds. Generation of the thermal vapor was complete by 250 milliseconds.

Example 139

Tacrine (MW 198, melting point 184° C.), an Alzheimer's disease manager, was coated on a stainless steel cylinder (8 cm$^2$) according to Method D. 0.978 mg of drug was applied to the substrate, for a calculated drug film thickness of 1.2 µm. The substrate was heated as described in Method D by charging the capacitors to 20.5 V. The purity of the drug-aerosol particles was determined to be 99.8%. 0.502 mg was recovered from the filter after vaporization, for a percent yield of 51.3%. A total mass of 0.841 mg was recovered from the test apparatus and substrate, for a total recovery of 86%.

Example 140

Figure 17:
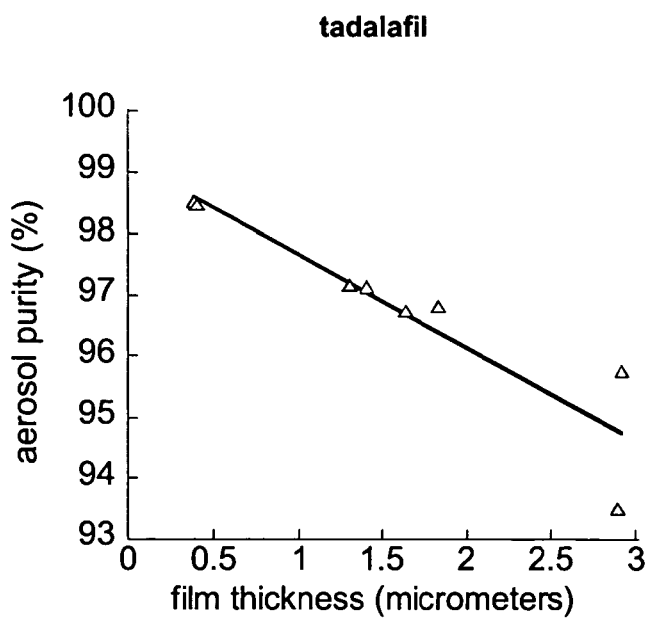
FIG. 17 is plot showing purity of thermal vapor as a function of drug film thickness, in micrometers, for tadalafil free base.
Figure 20:
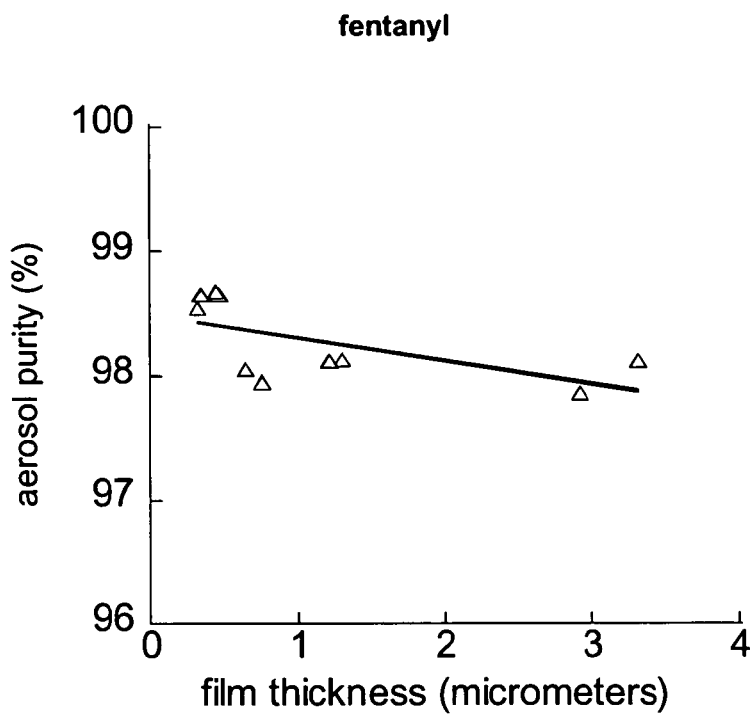
FIG. 20 is plot showing purity of thermal vapor as a function of drug film thickness, in micrometers, for fentanyl free base.

Tadalafil (MW 389, oral dose 5 mg), an erectile dysfunction therapeutic agent, was coated onto eight stainless steel foil substrates (5 cm$^2$) according to Method B. The calculated thickness of the drug film on each substrate ranged from about 0.5 µm to about 2.9 µm. The substrates were heated as described in Method B by charging the capacitors to 16 V. Purity of the drug-aerosol particles from each substrate was determined and the results are shown in FIG. 17.

Tadalafil was also coated on a stainless steel cylinder (8 cm$^2$). The calculated thickness of the drug film was 4.5 µm. The substrate was heated as described by the flashbulb and the purity of the drug-aerosol particles was determined to be 94.9%. 0.67 mg was recovered from the filter after vaporization, for a percent yield of 18.1%. A total mass of 1.38 mg was recovered from the test apparatus and substrate, for a total recovery of 37.3%.

Tadalafil was also coated on a piece of aluminum foil (20 cm$^2$) according to Method C. The calculated thickness of the drug film was 0.5 µm. The substrate was heated as described in Method C at 60 V for 13 seconds. The purity of the drug-aerosol particles was determined to be 91.2%. 0.45 mg was recovered from the glass tube walls after vaporization, for a percent yield of 45%.

Tadalafil was also coated on a piece of stainless steel foil (5 cm$^2$) according to Method B. 1.559 mg of drug was applied to the substrate, for a calculated drug film thickness of 2.9 µm. The substrate was heated as described in Method B by charging the capacitors to 16 V. The purity of the drug-aerosol particles was determined to be 95.8%. 1.42 mg was recovered from the filter after vaporization, for a percent yield of 91.1%. A total mass of 1.559 mg was recovered from the test apparatus and substrate, for a total recovery of 100%.

The drug was also coated (1.653 mg) to a thickness of 3.1 µm on a piece of stainless steel foil (5 cm$^2$) according to Method B. The substrate was heated under an N$_2$ atmosphere by charging the capacitors to 16 V. The purity of the drug-aerosol particles was determined to be 99.2%. 1.473 mg was recovered from the filter after vaporization, for a percent yield of 89.1%. A total mass of 1.653 mg was recovered from the test apparatus and substrate, for a total recovery of 100%.

Example 141

Terbutaline (MW 225, melting point 122° C., oral dose 0.2 mg), a respiratory agent, was coated on a stainless steel cylinder (9 cm$^2$) according to Method D. 2.32 mg of drug was applied to the substrate, for a calculated drug film thickness of 2.7 µm. The substrate was heated as described in Method D by charging the capacitors to 20.5 V. The purity of the drug-aerosol particles was determined to be 99.3%. 1.54 mg was recovered from the filter after vaporization, for a percent yield of 66.4%. A total mass of 1.938 mg was recovered from the test apparatus and substrate, for a total recovery of 83.5%.

Example 142

Testosterone (MW 288, melting point 155° C., oral dose 3 mg), a hormone, was coated on a stainless steel cylinder (8 cm$^2$) according to Method D. 0.96 mg of drug was applied to the substrate, for a calculated drug film thickness of 1.2 µm. The substrate was heated as described in Method D by charging the capacitors to 20.5 V. The purity of the drug-aerosol particles was determined to be 99.6%. 0.62 mg was recovered from the filter after vaporization, for a percent yield of 64.6%. A total mass of 0.96 mg was recovered from the test apparatus and substrate, for a total recovery of 100%.

Example 143

Thalidomide (MW 258, melting point 271° C., oral dose 100 mg), an immunomodulator, was coated on a stainless steel cylinder (8 cm$^2$) according to Method D. 0.57 mg of drug was applied to the substrate, for a calculated drug film thickness of 0.7 µm. The substrate was heated as described in Method D by charging the capacitors to 20.5 V. The purity of the drug-aerosol particles was determined to be >99.5%. 0.43 mg was recovered from the filter after vaporization, for a percent yield of 75.4%. A total mass of 0.54 mg was recovered from the test apparatus and substrate, for a total recovery of 94.7%.

Example 144

Theophylline (MW 180, melting point 274° C., oral dose 200 mg), a respiratory agent, was coated on a stainless steel cylinder (8 cm$^2$) according to Method D. 0.859 mg of drug was applied to the substrate, for a calculated drug film thickness of 1.0 μm. The substrate was heated as described in Method D by charging the capacitors to 20.5 V. The purity of the drug-aerosol particles was determined to be 100.0%. 0.528 mg was recovered from the filter after vaporization, for a percent yield of 61.5%. A total mass of 0.859 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 160 milliseconds. Generation of the thermal vapor was complete by 350 milliseconds.

Example 145

Tocamide (MW 192, melting point 247° C., oral dose 400 mg), a cardiovascular agent, was coated on a stainless steel cylinder (8 cm$^2$) according to Method D. 0.86 mg of drug was applied to the substrate, for a calculated drug film thickness of 1 μm. The substrate was heated as described in Method D by charging the capacitors to 20.5 V. The purity of the drug-aerosol particles was determined to be 99.7%. 0.65 mg was recovered from the filter after vaporization, for a percent yield of 75.6%. A total mass of 0.86 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 75 milliseconds. Generation of the thermal vapor was complete by 130 milliseconds.

Example 146

Tolfenamic Acid (MW 262, melting point 208° C., oral dose 200 mg), an analgesic, was coated on a piece of aluminum foil (20 cm$^2$) according to Method C. The calculated thickness of the drug film was 5.0 μm. The substrate was heated as described in Method C at 60 V for 6 seconds. The purity of the drug-aerosol particles was determined to be 94.2%. 6.49 mg was recovered from the glass tube walls after vaporization, for a percent yield of 65.6%.

Example 147

Tolterodine (MW 325, oral dose 2 mg), an urinary tract agent, was coated on a stainless steel cylinder (8 cm$^2$) according to Method D. 1.39 mg of drug was applied to the substrate, for a calculated drug film thickness of 1.7 μm. The substrate was heated as described in Method D by charging the capacitors to 20.5 V. The purity of the drug-aerosol particles was determined to be 96.9%. 1.03 mg was recovered from the filter after vaporization, for a percent yield of 74.1%. A total mass of 1.39 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 80 milliseconds. Generation of the thermal vapor was complete by 100 milliseconds.

Example 148

Toremifene (MW 406, melting point 110° C., oral dose 60 mg), an antineoplastic, was coated on a stainless steel cylinder (8 cm$^2$). 1.20 mg of drug was applied to the substrate, for a calculated thickness of the drug film of 1.4 μm, and heated to form drug-aerosol particles according to Method D by charging the capacitors to 20.5 V. The purity of the drug-aerosol particles was determined to be 98.7%. The yield of aerosol particles was 50%. 1.09 mg of total mass was recovered for a total recovery yield of 90.8%.

Example 149

Tramadol (MW 263, oral dose 50 mg), an analgesic, was coated on an aluminum foil substrate (20 cm$^2$) according to Method C. 4.90 mg of drug was applied to the substrate, for a calculated thickness of the drug film of 2.5 μm. The substrate was heated as described in Method C at 108 V for 2.25 seconds. The purity of the drug-aerosol particles was determined to be 96.9%. 3.39 mg was recovered from the glass tube walls after vaporization, for a percent yield of 69.2%.

Tramadol (2.6 mg) was also coated on a piece of aluminum foil (20 cm$^2$) according to Method C to a film thickness (calculated) of 1.3 μm. The substrate was heated as described in Method C under an argon atmosphere at 90 V for 3.5 seconds. The purity of the drug-aerosol particles was determined to be 96.1%. 1.79 mg was recovered from the glass tube walls after vaporization, for a percent yield of 68.8%.

Tramadol (2.1 mg) was also coated on a piece of aluminum foil (20 cm$^2$) according to Method C to a film thickness (calculated) of 1.1 μm. The substrate was heated as described in Method C under air at 90 V for 3.5 seconds. The purity of the drug-aerosol particles was determined to be 96.6%. 1.33 mg was recovered from the glass tube walls after vaporization, for a percent yield of 63.8%.

The hydrochloride salt form was also tested. 2.6 mg of drug was coated onto an aluminum foil substrate (20 cm$^2$) according to Method C to a film thickness (calculated) of 1.3 μm. The substrate was heated as described in Method C and purity of the drug-aerosol particles was determined to be 97.6%. 1.67 mg was recovered from the glass tube walls after vaporization, for a percent yield of 64.2%. An identical substrate having an identical drug film thickness was tested under an argon atmosphere at 90 V for 3.5 seconds. The purity of the drug-aerosol particles was determined to be 89%. 1.58 mg was recovered from the glass tube walls after vaporization, for a percent yield of 60.8%

Tramadol (17.5 mg) was also coated on a piece of aluminum foil (40 cm$^2$) according to Method F to a film thickness (calculated) of 4.38 μm. The substrate was heated as described in Method F and purity of the drug-aerosol particles was determined to be 97.3%.

Example 150

Tranylcypromine (MW 133, melting point <25° C., oral dose 30 mg), a psychotherapeutic agent, was coated on a piece of aluminum foil (20 cm$^2$) according to Method C. The calculated thickness of the drug film was 5.4 μm. The substrate was heated as described in Method C at 90 V for 5 seconds. The purity of the drug-aerosol particles was determined to be 93.7%. 7.4 mg was recovered from the glass tube walls after vaporization, for a percent yield of 68.5%.

Another substrate containing tranylcypromine coated to a film thickness of 2.7 μm was prepared by the same method and heated under an argon atmosphere at 90 V for 3.5 seconds. The purity of the drug-aerosol particles was determined to be 95.9%. 3 mg was recovered from the glass tube walls after vaporization, for a percent yield of 56.6%.

Tranylcypromine HCl (MW 169, melting point 166° C., oral dose 30 mg), a psychotherapeutic agent, was coated on a piece of aluminum foil (20 cm²) according to Method C. The calculated thickness of the drug film was 1.2 µm. The substrate was heated as described in Method C at 90 V for 3.5 seconds. The purity of the drug-aerosol particles was determined to be 97.5%. 1.3 mg was recovered from the glass tube walls after vaporization, for a percent yield of 56.5%.

Example 151

Trazodone (MW 372, melting point 87° C., oral dose 400 mg), a psychotherapeutic agent, was coated on an aluminum foil substrate (20 cm²) according to Method C. 10.0 mg of drug was applied to the substrate, for a calculated thickness of the drug film of 5.0 µm. The substrate was heated as described in Method C at 60 V for 15 seconds. The purity of the drug-aerosol particles was determined to be 98.9%. 8.5 mg was recovered from the glass tube walls after vaporization, for a percent yield of 85%.

Trazodone was further coated on an aluminum foil substrate according to Method G. The substrate was heated as described in Method G at 90 V for 3.5 seconds. The purity of the drug-aerosol particles was determined to be 97.9%. The percent yield of the aerosol was 29.1%. The purity of the drug-aerosol particles was determined to be 98.5% when the system was flushed through with argon prior to volatilization. The percent yield of the aerosol was 25.5%.

Example 152

Triazolam (MW 343, melting point 235° C., oral dose 0.13 mg), a sedative and hypnotic, was coated on an aluminum foil substrate (20 cm²) according to Method C. 1.7 mg of drug was applied to the substrate, for a calculated thickness of the drug film of 0.9 µm. The substrate was heated as described in Method C at 45 V for 18 seconds. The purity of the drug-aerosol particles was determined to be 99.2%. 1.6 mg was recovered from the glass tube walls after vaporization, for a percent yield of 94.1%.

Another aluminum foil substrate (28.8 cm²) was prepared according to Method C. 1.7 mg of triazolam was applied to the substrate, for a calculated thickness of the drug film of 0.69 µm. The substrate was heated substantially as described in Method C at 75 V for 2 seconds and then at 45 V for 8 seconds. The purity of the drug-aerosol particles was determined to be 99.3%. 1.7 mg of aerosol particles were collected for a percent yield of 100%.

Triazolam was also applied to an aluminum foil substrate (36 cm²) according to Method G. 0.6 mg of the drug was applied to the substrate, for a calculated thickness of the drug film of 0.17 µm. The substrate was heated substantially as described in Method G at 90 V for 6 seconds, except that one of the openings of the T-shaped tube was sealed with a rubber stopper, one was loosely covered with the end of the halogen tube, and the third connected to the 1 L flask. The purity of the drug-aerosol particles was determined to be >99%. All of the drug was found to have aerosolized, for a percent yield of 100%.

Example 153

Trifluoperazine (MW 407, melting point <25° C., oral dose 7.5 mg), a psychotherapeutic agent, was coated on a stainless steel cylinder (9 cm²) according to Method D. 1.034 mg of drug was applied to the substrate, for a calculated drug film thickness of 1.1 µm. The substrate was heated as described in Method D by charging the capacitors to 19 V. The purity of the drug-aerosol particles was determined to be 99.8%. 0.669 mg was recovered from the filter after vaporization, for a percent yield of 64.7%. A total mass of 1.034 mg was recovered from the test apparatus and substrate, for a total recovery of 100%.

Trifluoperazine 2HCl salt (MW 480, melting point 243° C., oral dose 7.5 mg) was coated on an identical substrate. Specifically, 0.967 mg of drug was applied to the substrate, for a calculated drug film thickness of 1.1 μm. The substrate was heated as described in Method D by charging the capacitors to 20.5 V. The purity of the drug-aerosol particles was determined to be 87.5%. 0.519 mg was recovered from the filter after vaporization, for a percent yield of 53.7%. A total mass of 0.935 mg was recovered from the test apparatus and substrate, for a total recovery of 96.7%.

High speed photographs of trifluoperazine 2HCl were taken as the drug-coated substrate was heated to monitor visually formation of a thermal vapor. The photographs showed that a thermal vapor was initially visible 25 milliseconds after heating was initiated, with the majority of the thermal vapor formed by 120 milliseconds. Generation of the thermal vapor was complete by 250 milliseconds.

Example 154

Trimipramine maleate (MW 411, melting point 142° C., oral dose 50 mg), a psychotherapeutic agent, was coated on a piece of aluminum foil (20 $cm^2$) according to Method C. The calculated thickness of the drug film was 1.2 μm. The substrate was heated as described in Method C at 90 V for 3.5 seconds. The purity of the drug-aerosol particles was determined to be 95.9%. 1.6 mg was recovered from the glass tube walls after vaporization, for a percent yield of 66.7%.

Another substrate containing trimipramine maleate coated to a film thickness of 1.1 μm was prepared by the same method and heated under an argon atmosphere at 90 V for 3.5 seconds. The purity of the drug-aerosol particles was determined to be 97.4%. 2.1 mg was recovered from the glass tube walls after vaporization, for a percent yield of 95.5%.

Example 155

Valdecoxib (MW 314, melting point 155° C., oral dose 10 mg), an anti-rheumatic agent, was coated on a piece of stainless steel foil (5 $cm^2$) according to Method B. The calculated thickness of the drug film was 8.0 μm. The substrate was heated as described in Method B by charging the capacitors to 15.5 V. The purity of the drug-aerosol particles was determined to be 96.9%. 1.235 mg was recovered from the filter after vaporization, for a percent yield of 28.9%. A total mass of 3.758 mg was recovered from the test apparatus and substrate, for a total recovery of 87.9%.

Valdecoxib was also coated on a piece of stainless steel foil (6 $cm^2$) according to Method B. 0.716 mg of drug was applied to the substrate, for a calculated drug film thickness of 1.3 μm. The substrate was heated as described in Method B by charging the capacitors to 15 V. The purity of the drug-aerosol particles was determined to be 98.6%. 0.466 mg was recovered from the filter after vaporization, for a percent yield of 65.1%. A total mass of 0.49 mg was recovered from the test apparatus and substrate, for a total recovery of 68.4%.

Example 156

Valproic Acid (MW 144, melting point <25° C., oral dose 60 mg), an anticonvulsant, was coated on a metal substrate (50 $cm^2$) according to Method F. 82.4 mg of drug was applied to the substrate, for a calculated drug film thickness of 16.5 µm. The substrate was heated according to Method F at 300° C. to form drug-aerosol particles. Purity of the drug-aerosol particles was determined to be 99.7% by GC analysis. 60 mg of the drug were collected for a percent yield of 72.8%.

Example 157

Vardenafil (MW 489, oral dose 5 mg), an erectile dysfunction therapy agent, was coated on a stainless steel cylinder (6 cm²) according to Method E. The calculated thickness of the drug film was 2.7 µm. The substrate was heated as described in Method E and purity of the drug-aerosol particles was determined to be 79%. 0.723 mg was recovered from the filter after vaporization, for a percent yield of 44.4%.

Another substrate (stainless steel cylinder (6 cm²)) was prepared by applying 0.18 mg drug to form a film 0.3 µm in thickness. The substrate was heated as described in Method E and purity of the drug-aerosol particles was determined to be 96.8%. 0.11 mg was recovered from the filter after vaporization, for a percent yield of 63.1%. A total mass of 0.14 mg was recovered from the test apparatus and substrate, for a total recovery of 81.8%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 90 milliseconds. Generation of the thermal vapor was complete by 110 milliseconds.

Example 158

Venlafaxine (MW 277, oral dose 50 mg), a psychotherapeutic agent, was coated on a stainless steel cylinder (6 cm²) according to Method E. 5.85 mg of drug was applied to the substrate, for a calculated drug film thickness of 9.8 µm. The substrate was heated as described in Method E and purity of the drug-aerosol particles was determined to be 99.4%. 3.402 mg was recovered from the filter after vaporization, for a percent yield of 58.1%. A total mass of 5.85 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 100 milliseconds. Generation of the thermal vapor was complete by 400 milliseconds.

Example 159

Verapamil (MW 455, melting point <25° C., oral dose 40 mg), a cardiovascular agent, was coated on a piece of aluminum foil (20 cm²) according to Method C. The calculated thickness of the drug film was 1.1 µm. The substrate was heated under an argon atmosphere at 90 V for 3.5 seconds. The purity of the drug-aerosol particles was determined to be 96.2%. 1.41 mg was recovered from the glass tube walls after vaporization, for a percent yield of 64.1%.

Verapamil was also coated on a stainless steel cylinder (8 cm²) according to Method D. 0.75 mg of drug was applied to the substrate, for a calculated drug film thickness of 0.9 µm. The substrate was heated as described in Method D by charging the capacitors to 20.5 V. The purity of the drug-aerosol particles was determined to be 89.6%. 0.32 mg was recovered from the filter after vaporization, for a percent yield of 42.7%. A total mass of 0.6 mg was recovered from the test apparatus and substrate, for a total recovery of 80%.

Example 160

Vitamin E (MW 430, melting point 4° C.), a dietary supplement, was coated on a stainless steel cylinder (8 cm²) according to Method D. 0.78 mg of drug was applied to the substrate, for a calculated drug film thickness of 0.9 µm. The substrate was heated as described in Method D by charging the capacitors to 20.5 V. The purity of the drug-aerosol particles was determined to be 99.3%. 0.48 mg was recovered from the filter after vaporization, for a percent yield of 61.8%. A total mass of 0.6 mg was recovered from the test apparatus and substrate, for a total recovery of 81.4%.

Example 161

Zaleplon (MW 305, melting point 159° C., oral dose 5 mg), a sedative and hypnotic, was coated on a piece of aluminum foil (20 cm²) according to Method C. The calculated thickness of the drug film was 2.3 µm. The substrate was heated as described in Method C at 60 V for 12 seconds. The purity of the drug-aerosol particles was determined to be 99.5%. 4.07 mg was recovered from the glass tube walls after vaporization, for a percent yield of 90.4%.

Example 162

Zolmitriptan (MW 287, melting point 141° C., oral dose 1.25 mg), a migraine preparation, was coated on a piece of aluminum foil (20 cm²) according to Method C. The calculated thickness of the drug film was 1.6 µm. The substrate was heated as described in Method C at 60 V for 11 seconds. The purity of the drug-aerosol particles was determined to be 93%. 1.1 mg was recovered from the glass tube walls after vaporization, for a percent yield of 35.5%.

Another substrate containing zolmitriptan coated to a film thickness of 2.0 µm was prepared by the same method and heated under an argon atmosphere at 90 V for 4 seconds. The purity of the drug-aerosol particles was determined to be 98.4%. 0.6 mg was recovered from the glass tube walls after vaporization, for a percent yield of 15%.

Another substrate (36 cm²) containing zolmitriptan was prepared according to Method C. 9.8 mg of the drug was applied to the substrate, for a calculated thickness of the drug film of 2.7 µm. The substrate was heated substantially as described in Method C at 60 V for 15 seconds. The purity of the drug-aerosol particles was determined to be 98%. The aerosol percent yield was 38%.

Zolmitriptan was further coated on an aluminum foil substrate (24.5 cm²) according to Method G. 2.6 mg of the drug was applied to the substrate, for a calculated thickness of the drug film of 1.1 µm. The substrate was heated as described in Method G at 90 V for 6 seconds. The purity of the drug-aerosol particles was determined to be >96%. 1.5 mg of the drug was found to have aerosolized, for a percent yield of 57.7%.

Example 163

Figures 18, 19:
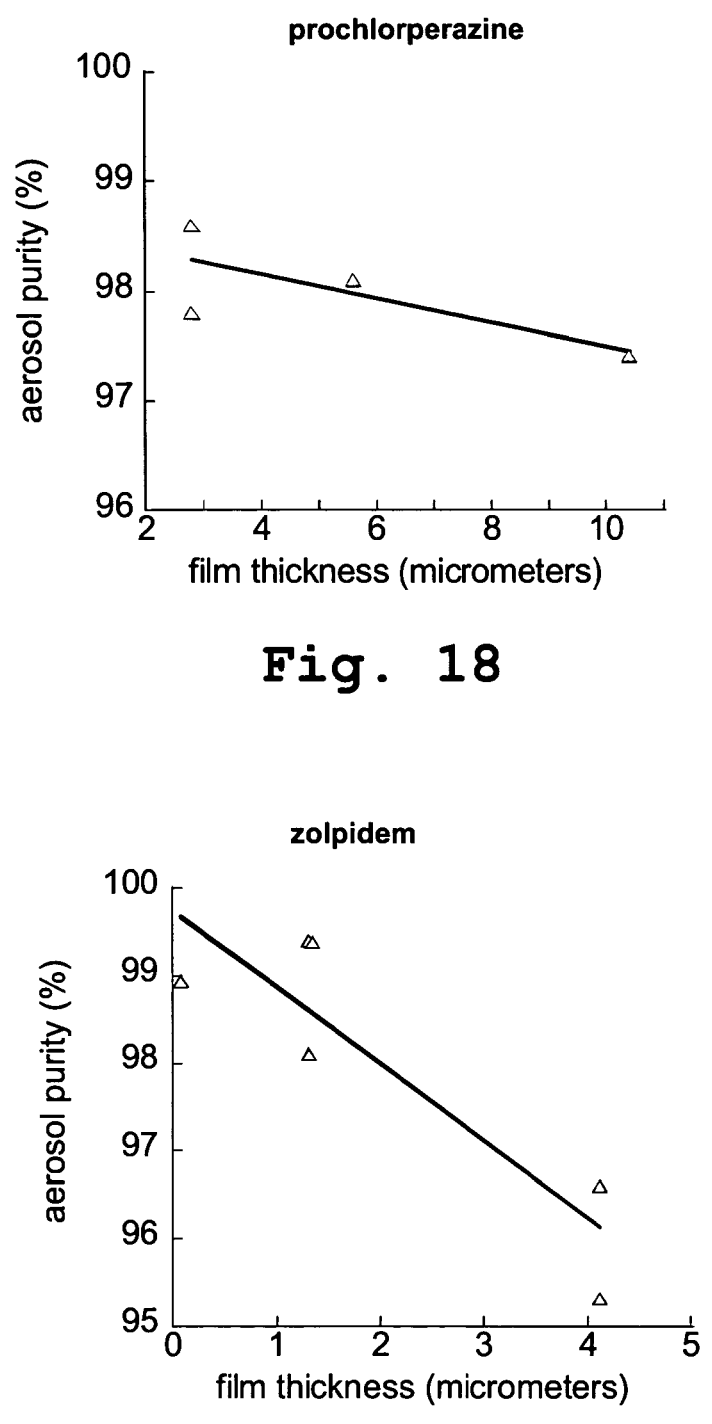

Zolpidem (MW 307, melting point 196° C., oral dose 5 mg), a sedative and hypnotic, was coated onto six stainless steel cylindrical substrates according to Method E. The calculated thickness of the drug film on each substrate ranged from about 0.1 µm to about 4.2 µm. The substrates were heated as described in Method E and purity of the drug-aerosol particles generated from each substrate determined. The results are shown in FIG. 19.

Zolpidem was also coated on a stainless steel cylinder (6 cm$^2$) according to Method E. 4.13 mg of drug was applied to the substrate, for a calculated drug film thickness of 6.9 μm. The substrate was heated as described in Method E and purity of the drug-aerosol particles was determined to be 96.6%. 2.6 mg was recovered from the filter after vaporization, for a percent yield of 63%. A total mass of 3.18 mg was recovered from the test apparatus and substrate, for a total recovery of 77%.

High speed photographs were taken as the drug-coated substrate was heated to monitor visually formation of a thermal vapor. The photographs showed that a thermal vapor was initially visible 35 milliseconds after heating was initiated, with the majority of the thermal vapor formed by 120 milliseconds. Generation of the thermal vapor was complete by 225 milliseconds.

Zolpidem was also coated on an aluminum substrate (24.5 cm$^2$) according to Method G. 8.3 mg of drug was applied to the substrate, for a calculated drug film thickness of 3.4 μm. The substrate was heated as described in Method G at 90 V for 6 seconds. The purity of the drug-aerosol particles was determined to be >97%. 7.4 mg of the drug was found to have aerosolized by weight loss from substrate mass, for a percent yield of 89.2%.

Example 164

Zopiclone (MW 388, melting point 178° C., oral dose 7.50 mg), a sedative and hypnotic, was coated on an aluminum foil substrate (20 cm$^2$) according to Method C. 3.7 mg of drug was applied to the substrate, for a calculated thickness of the drug film of 1.9 μm. The substrate was heated as described in Method C at 60 V for 9 seconds. The purity of the drug-aerosol particles was determined to be 97.9%. 2.5 mg was recovered from the glass tube walls after vaporization, for a percent yield of 67.6%.

Zopiclone was further coated on an aluminum foil substrate (24 cm$^2$) according to Method C. 3.5 mg of drug was applied to the substrate, for a calculated thickness of the drug film of 1.5 μm. The substrate was heated substantially as described in Method C at 60 V for 6 seconds. The purity of the drug-aerosol particles was determined to be >99%.

Example 165

Zotepine (MW 332, melting point 91° C., oral dose 25 mg), a psychotherapeutic agent, was coated on a stainless steel cylinder (8 cm$^2$) according to Method D. 0.82 mg of drug was applied to the substrate, for a calculated drug film thickness of 1 μm. The substrate was heated as described in Method D by charging the capacitors to 20.5 V. The purity of the drug-aerosol particles was determined to be 98.3%. 0.72 mg was recovered from the filter after vaporization, for a percent yield of 87.8%. A total mass of 0.82 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 60 milliseconds. Generation of the thermal vapor was complete by 110 milliseconds.

Example 166

Adenosine (MW 267, melting point 235° C., oral dose 6 mg), an anti-arrhythmic cardiovascular agent, was coated on a stainless steel cylinder (8 cm$^2$) according to Method D. 1.23 mg of drug was applied to the substrate, for a calculated drug film thickness of 1.5 μm. The substrate was heated as described in Method D by charging the capacitors to 20.5 V. The purity of the drug-aerosol particles was determined to be 70.6%. 0.34 mg was recovered from the filter after vaporization, for a percent yield of 27.6%. A total mass of 0.68 mg was recovered from the test apparatus and substrate, for a total recovery of 55.3%.

High speed photographs were taken as the drug-coated substrate was heated to monitor visually formation of a thermal vapor. The photographs showed that a thermal vapor was initially visible 40 milliseconds after heating was initiated, with the majority of the thermal vapor formed by 250 milliseconds. Generation of the thermal vapor was complete by 535 milliseconds.

Example 167

Amoxapine (MW 314, melting point 176° C., oral dose 25 mg), an anti-psychotic agent, was coated on a stainless steel cylinder (8 cm$^2$) according to Method D. 6.61 mg of drug was applied to the substrate, for a calculated drug film thickness of 7.9 μm. The substrate was heated as described in Method D by charging the capacitors to 20.5 V. The purity of the drug-aerosol particles was determined to be 99.7%. 3.13 mg was recovered from the filter after vaporization, for a percent yield of 47.4%. A total mass of 6.61 mg was recovered from the test apparatus and substrate, for a total recovery of 100%.

Example 168

Apomorphine 10,11 cyclocarbonate (MW 293, typical aerosol dose 1 mg), a dopaminergic agent used in Parkinson's patients, was coated on a piece of aluminum foil (20 cm$^2$) according to Method C. The calculated thickness of the drug film was 1.2 μm. The substrate was heated as described in Method C at 90 V for 3 seconds. The purity of the drug-aerosol particles was determined to be 78.4%. 1.46 mg was recovered from the glass tube walls after vaporization, for a percent yield of 60.8%.

Example 169

Aripiprazole (MW 448, melting point 140° C., oral dose 5 mg), an anti-psychotic agent, was coated on a stainless steel cylinder (8 cm$^2$) according to Method D. 1.139 mg of drug was applied to the substrate, for a calculated drug film thickness of 1.4 μm. The substrate was heated as described in Method D by charging the capacitors to 20.5 V. The purity of the drug-aerosol particles was determined to be 91.1%. 0.251 mg was recovered from the filter after vaporization, for a percent yield of 22%. A total mass of 1.12 mg was recovered from the test apparatus and substrate, for a total recovery of 98%.

High speed photographs were taken as the drug-coated substrate was heated to monitor visually formation of a thermal vapor. The photographs showed that a thermal vapor was initially visible 55 milliseconds after heating was initiated, with the majority of the thermal vapor formed by 300 milliseconds. Generation of the thermal vapor was complete by 1250 milliseconds.

A second substrate coated with arirpirazole was prepared for testing. 1.139 mg was coated on a stainless steel cylinder (8 cm$^2$) according to Method D, for a calculated drug film thickness of 1.4 μm. The substrate was heated as described in Method D by charging the capacitors to 20.5 V. The purity of the drug-aerosol particles was determined to be 86.9%. 0.635 mg was recovered from the filter after vaporization, for a percent yield of 55.8%. A total mass of 1.092 mg was recovered from the test apparatus and substrate, for a total recovery of 95.8%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 200 milliseconds. Generation of the thermal vapor was complete by 425 milliseconds.

Example 170

Aspirin (MW 180, melting point 135° C., oral dose 325 mg), an analgesic agent, was coated on a piece of aluminum foil (20 cm$^2$) according to Method C. The calculated thickness of the drug film was 1.2 μm. The substrate was heated as described in Method C at 60 V for 5 seconds. The purity of the drug-aerosol particles was determined to be 82.1%. 1.23 mg was recovered from the glass tube walls after vaporization, for a percent yield of 53.5%.

Example 171

Astemizole (MW 459, melting point 173° C., oral dose 10 mg), an antihistamine, was coated on an aluminum foil substrate (20 cm$^2$) according to Method C. 5.0 mg of drug was applied to the substrate, for a calculated thickness of the drug film of 2.5 μm. The substrate was heated as described in Method C at 60 V for 11 seconds. The purity of the drug-aerosol particles was determined to be 88%. 1.6 mg was recovered from the glass tube walls after vaporization, for a percent yield of 32.0%.

A similarly prepared substrate having the same film thickness was heated at 60 V for 11 seconds under a pure argon atmosphere. The purity of the drug-aerosol particles was determined to be 93.9%. 1.7 mg was recovered from the glass tube walls after vaporization, for a percent yield of 34.0%.

Example 172

Atenolol (MW 266, melting point 152° C., oral dose 25 mg), a beta adrenergic blocking agent, was coated on a piece of aluminum foil (20 cm$^2$) according to Method C. 22.6 mg was applied to the substrate, for a calculated thickness of the drug film of 11.3 μm. The substrate was heated as described in Method C at 60 V for 11 seconds. The purity of the drug-aerosol particles was determined to be 94%. 1.0 mg was recovered from the glass tube walls after vaporization, for a percent yield of 4.4%.

Another atenolol-coated substrate was prepared by the same method, with 17.9 mg of drug applied to the substrate, for a calculated film thickness of 9.0 μm. The substrate was heated under an argon atmosphere according to Method C at 60 V for 3.5 seconds. The purity of the drug-aerosol particles was determined to be >99.5%. 2.0 mg was recovered from the glass tube walls after vaporization, for a percent yield of 11%.

Atenolol was further coated on an aluminum foil substrate according to Method G. The substrate was heated as described in Method G, and the purity of the drug-aerosol particles was determined to be 100%. The percent yield of the aerosol was 10%.

Example 173

Benazepril (MW 424, melting point 149° C., oral dose 10 mg), an ACE inhibitor, cardiovascular agent, was coated on a stainless steel cylinder (8 cm$^2$) according to Method D. The calculated thickness of the drug film was 0.9 μm. The substrate was heated as described in Method D by charging the capacitors to 20.5 V. The purity of the drug-aerosol particles was determined to be 90%. 0.34 mg was recovered from the filter after vaporization, for a percent yield of 45.3%. A total mass of 0.6 mg was recovered from the test apparatus and substrate, for a total recovery of 77.3%.

Example 174

Benztropine (MW 307, melting point 143° C., oral dose 1 mg), an anti-cholinergic, antiparkinsonian agent, was coated onto an aluminum foil substrate (20 cm$^2$) according to Method C. 2.10 mg of drug was applied to the substrate, for a calculated thickness of the drug film of 1.1 μm. The substrate was heated as described in Method C at 90 V for 3.5 seconds. The purity of the drug-aerosol particles was determined to be 98.3%. 0.83 mg was recovered from the glass tube walls after vaporization, for a percent yield of 39.5%.

Another benztropine-coated substrate was prepared by the same method, with 2.0 mg of drug was applied to the substrate, for a calculated film thickness of 1.0 μm. The substrate was heated under an argon atmosphere at 90 V for 3.5 seconds. The purity of the drug-aerosol particles was determined to be 99.5%. 0.96 mg was recovered from the glass tube walls after vaporization, for a percent yield of 48%.

Example 175

Bromazepam (MW 316, melting point 239° C., oral dose 2 mg), a psychotherapeutic agent used as an anti-anxiety drug, was coated on a piece of aluminum foil (20 cm$^2$) according to Method C. The calculated thickness of the drug film was 5.2 μm. The substrate was heated as described in Method C at 30 V for 45 seconds. The purity of the drug-aerosol particles was determined to be 96.9%. 2.2 mg was recovered from the glass tube walls after vaporization, for a percent yield of 21.2%.

Example 176

Budesonide (MW 431, melting point 232° C., oral dose 0.2 mg), an anti-inflammatory steroid used as a respiratory agent, was coated on a stainless steel cylinder (9 cm$^2$) according to Method D. 1.46 mg of drug was applied to the substrate, for a calculated drug film thickness of 1.7 μm. The substrate was heated as described in Method D by charging the capacitors to 20.5 V. The purity of the drug-aerosol particles was determined to be 70.5%. 0.37 mg was recovered from the filter after vaporization, for a percent yield of 25.3%. A total mass of 0.602 mg was recovered from the test apparatus and substrate, for a total recovery of 41.2%.

Example 177

Buspirone (MW 386, oral dose 15 mg), a psychotherapeutic agent, was coated on an aluminum foil substrate (20 cm$^2$) according to Method C. 7.60 mg of drug was applied to the substrate, for a calculated thickness of the drug film of 3.8 μm. The substrate was heated as described in Method C at 60 V for 7 seconds. The purity of the drug-aerosol particles was determined to be 96.5%. 1.75 mg was recovered from the glass tube walls after vaporization, for a percent yield of 23%.

Another substrate containing buspirone coated to a film thickness of 4.6 μm was prepared by the same method and heated under an argon atmosphere at 60 V for 7 seconds. The purity of the drug-aerosol particles was determined to be 96.1%. 2.7 mg was recovered from the glass tube walls after vaporization, for a percent yield of 29.7%.

The hydrochloride salt (MW 422) was also tested. Buspirone hydrochloride was coated on a piece of aluminum foil (20 cm$^2$) according to Method C. 8.30 mg of drug was applied to the substrate, for a calculated thickness of the drug film of 4.2 µm. The substrate was heated as described in Method C at 90 V for 5 seconds. The purity of the drug-aerosol particles was determined to be 97.8%. 2.42 mg was recovered from the glass tube walls after vaporization, for a percent yield of 29.2%.

Example 178

Caffeine (MW 194, melting point 238° C., oral dose 100 mg), a central nervous system stimulant, was coated on a metal substrate (50 cm$^2$). 100 mg of drug was applied to the substrate, for a calculated drug film thickness of 14 µm and heated to 300° C. according to Method F to form drug-aerosol particles. Purity of the drug-aerosol particles was determined to be >99.5%. 40 mg was recovered from the glass wool after vaporization, for a percent yield of 40%.

Example 179

Captopril (MW 217, melting point 104° C., oral dose 25 mg), an ACE inhibitor, cardiovascular agent, was coated on a stainless steel cylinder (8 cm$^2$) according to Method D. 0.88 mg of drug was applied to the substrate, for a calculated drug film thickness of 1.1 µm. The substrate was heated as described in Method D by charging the capacitors to 20.5 V. The purity of the drug-aerosol particles was determined to be 87.5%. 0.54 mg was recovered from the filter after vaporization, for a percent yield of 61.4%. A total mass of 0.8 mg was recovered from the test apparatus and substrate, for a total recovery of 90.9%.

High speed photographs were taken as the drug-coated substrate was heated to monitor visually formation of a thermal vapor. The photographs showed that a thermal vapor was initially visible 20 milliseconds after heating was initiated, with the majority of the thermal vapor formed by 100 milliseconds. Generation of the thermal vapor was complete by 170 milliseconds.

Example 180

Carbamazepine (MW 236, melting point 193° C., oral dose 200 mg), an anticonvulsant agent, was coated on a stainless steel cylinder (8 cm$^2$) according to Method D. 0.73 mg of drug was applied to the substrate, for a calculated drug film thickness of 0.9 µm. The substrate was heated as described in Method D by charging the capacitors to 20.5 V. The purity of the drug-aerosol particles was determined to be 88.9%. 0.43 mg was recovered from the filter after vaporization, for a percent yield of 58.9%. A total mass of 0.6 mg was recovered from the test apparatus and substrate, for a total recovery of 78.1%.

Example 181

Cinnarizine (MW 369, oral dose 15 mg), an antihistamine, was coated on an aluminum foil substrate (20 cm$^2$) according to Method C. 18.0 mg of drug was applied to the substrate, for a calculated thickness of the drug film of 9 µm. The substrate was heated as described in Method C at 60 V for 8 seconds. The purity of the drug-aerosol particles was determined to be 96.7%. 3.15 mg was recovered from the glass tube walls after vaporization, for a percent yield of 17.5%.

Another substrate containing cinnarizine coated (5.20 mg drug) to a film thickness of 2.6 µm was prepared by the same method and heated under an argon atmosphere at 60 V for 8 seconds. The purity of the drug-aerosol particles was determined to be 91.8%. 2.3 mg was recovered from the glass tube walls after vaporization, for a percent yield of 44.2%.

Example 182

Clemastine (MW 344, melting point <25° C., oral dose 1 mg), a antihistamine, was coated on a piece of aluminum foil (20 cm$^2$) according to Method C. The calculated thickness of the drug film was 3.2 µm. The substrate was heated as described in Method C at 60 V for 7 seconds. The purity of the drug-aerosol particles was determined to be 94.3%. 3 mg was recovered from the glass tube walls after vaporization, for a percent yield of 46.9%.

Clemastine fumarate (MW 460, melting point 178° C., oral dose 1.34 mg) was coated on an identical substrate to a thickness of 2.9 µm. The substrate was heated at 60 V for 8 seconds. The purity of the drug-aerosol particles was determined to be 76.6%. 1.8 mg was recovered from the glass tube walls after vaporization, for a percent yield of 31.6%.

Example 183

Clofazimine (MW 473, melting point 212° C., oral dose 100 mg), an anti-infective agent, was coated on a stainless steel cylinder (6 cm$^2$) according to Method D. 0.48 mg of drug was applied to the substrate, for a calculated drug film thickness of 0.8 µm. The substrate was heated as described in Method D by charging the capacitors to 20.5 V. The purity of the drug-aerosol particles was determined to be 84.4%. 0.06 mg was recovered from the filter after vaporization, for a percent yield of 12.5%. A total mass of 0.48 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 45 milliseconds after heating was initiated, with the majority of the thermal vapor formed by 300 milliseconds. Generation of the thermal vapor was complete by 1200 milliseconds.

Example 184

Desipramine (MW 266, melting point <25° C., oral dose 25 mg), a psychotherapeutic agent, was coated on a piece of aluminum foil (20 cm$^2$) according to Method C. The calculated thickness of the drug film was 5.2 µm. The substrate was heated as described in Method C at 90 V for 5 seconds. The purity of the drug-aerosol particles was determined to be 82.2%. 7.2 mg was recovered from the glass tube walls after vaporization, for a percent yield of 69.9%.

Example 185

Dipyridamole (MW 505, melting point 163° C., oral dose 75 mg), a blood modifier, was coated on a stainless steel cylinder (6 cm$^2$) according to Method D. 1.15 mg of drug was applied to the substrate, for a calculated drug film thickness of 1.9 µm. The substrate was heated as described in Method D by charging the capacitors to 20.5 V. The purity of the drug-aerosol particles was determined to be 95.3%. 0.22 mg was recovered from the filter after vaporization, for a percent yield of 19.1%. A total mass of 1.1 mg was recovered from the test apparatus and substrate, for a total recovery of 94.8%.

Example 186

Dolasetron (MW 324, oral dose 100 mg), a gastrointestinal agent, was coated on a piece of aluminum foil (20 cm$^2$) according to Method C. The calculated thickness of the drug film was 5 μm. The substrate was heated as described in Method C at 30 V for 45 seconds. The purity of the drug-aerosol particles was determined to be 83%. 6 mg was recovered from the glass tube walls after vaporization, for a percent yield of 60%.

Dolasetron was further coated on an aluminum foil substrate according to Method C. The substrate was heated substantially as described in Method C, and the purity of the drug-aerosol particles was determined to be 99%.

Example 187

Doxylamine (MW 270, melting point <25° C., oral dose 12.5 mg), an antihistamine, was coated on a stainless steel cylinder (8 cm$^2$) according to Method D. The calculated thickness of the drug film was 7.8 μm. The substrate was heated as described in Method D by charging the capacitors to 20.5 V. The purity of the drug-aerosol particles was determined to be 99.8%. 2.96 mg was recovered from the filter after vaporization, for a percent yield of 45.6%. A total mass of 6.49 mg was recovered from the test apparatus and substrate, for a total recovery of 100%.

Example 188

Droperidol (MW 379, melting point 147° C., oral dose 1 mg), a psychotherapeutic agent, was coated on a piece of aluminum foil (20 $cm^2$) according to Method C. The calculated thickness of the drug film was 1.1 μm. The substrate was heated as described in Method C at 90 V for 3.5 seconds. The purity of the drug-aerosol particles was determined to be 51%. 0.27 mg was recovered from the glass tube walls after vaporization, for a percent yield of 12.9%.

Another substrate containing droperidol coated to a film thickness of 1.0 μm was prepared by the same method and heated under an argon atmosphere at 90 V for 3.5 seconds. The purity of the drug-aerosol particles was determined to be 65%. 0.24 mg was recovered from the glass tube walls after vaporization, for a percent yield of 12.6%.

Example 189

Enalapril maleate (MW 493, melting point 145° C., oral dose 5 mg), a cardiovascular agent, was coated on a stainless steel cylinder (8 $cm^2$) according to Method D. The calculated thickness of the drug film was 1.1 μm. The substrate was heated as described in Method D by charging the capacitors to 20.5 V. The purity of the drug-aerosol particles was determined to be 61%. 0.29 mg was recovered from the filter after vaporization, for a percent yield of 34.1%. A total mass of 0.71 mg was recovered from the test apparatus and substrate, for a total recovery of 83.5%.

Example 190

Estradiol-17-acetate (MW 314, oral dose 2 mg), a hormonal pro-drug, was coated on a piece of aluminum foil (20 $cm^2$) according to Method C. The calculated thickness of the drug film was 0.9 μm. The substrate was heated as described in Method C at 60 V for 6 seconds. The purity of the drug-aerosol particles was determined to be 98.6%. 0.59 mg was recovered from the glass tube walls after vaporization, for a percent yield of 34.7%.

Example 191

Estradiol 17-heptanoate (MW 384 melting point 94° C., oral dose 1 mg), a hormone, was coated on a metal substrate (50 $cm^2$). 42 mg was applied to the substrate, for a calculated drug film thickness of 8.4 μm and heated according to Method F at 300° C. to form drug-aerosol particles. Purity of the drug-aerosol particles was determined to be 90% by GC analysis. The total mass recovered was 11.9%.

Example 192

Fluphenazine (MW 438, melting point <25° C., oral dose 1 mg), a psychotherapeutic agent, was coated on a piece of aluminum foil (20 $cm^2$) according to Method C. The calculated thickness of the drug film was 1.1 μm. The substrate was heated as described in Method C at 90 V for 3.5 seconds. The purity of the drug-aerosol particles was determined to be 93%. 0.7 mg was recovered from the glass tube walls after vaporization, for a percent yield of 33.3%.

The fluphenazine 2HCl salt form of the drug (MW 510, melting point 237° C.) was also tested. The drug was coated on a metal substrate (10 $cm^2$) according to Method D. The calculated thickness of the drug film was 0.8 μm. The substrate was heated as described in Method D by charging the capacitors to 20.5 V. The purity of the drug-aerosol particles was determined to be 80.7%. 0.333 mg was recovered from the filter after vaporization, for a percent yield of 42.6%. A total mass of 0.521 mg was recovered from the test apparatus and substrate, for a total recovery of 66.7%.

Example 193

Flurazepam (MW 388, melting point 82° C., oral dose 15 mg), sedative and hypnotic, was coated on a piece of aluminum foil (20 $cm^2$) according to Method C. The calculated thickness of the drug film was 2.5 μm. The substrate was heated as described in Method C at 60 V for 6 seconds. The purity of the drug-aerosol particles was determined to be 99.2%. 1.8 mg was recovered from the glass tube walls after vaporization, for a percent yield of 36%.

Flurazepam was further coated on an aluminum foil substrate (24 $cm^2$) according to Method C. 5 mg of the drug was applied to the substrate, for a calculated thickness of the drug film of 2.08 μm. The substrate was heated substantially as described in Method C at 60 V for 5 seconds. The purity of the drug-aerosol particles was determined to be 99.6%. The percent yield of the aerosol was 36%.

Example 194

Flurbiprofen (MW 244, melting point 111° C., oral dose 50 mg), an analgesic, was coated on a piece of aluminum foil (20 $cm^2$) according to Method C. The calculated thickness of the drug film was 4.7 μm. The substrate was heated as described in Method C at 60 V for 5 seconds. The purity of the drug-aerosol particles was determined to be >99.5%. 4.1 mg was recovered from the glass tube walls after vaporization, for a percent yield of 43.6%.

Example 195

Fluvoxamine (MW 318, oral dose 50 mg), a psychotherapeutic agent, was coated on a piece of aluminum foil (20 $cm^2$)

according to Method C. The calculated thickness of the drug film was 4.4 µm. The substrate was heated as described in Method C at 90 V for 5 seconds. The purity of the drug-aerosol particles was determined to be 65%. 6.5 mg was recovered from the glass tube walls after vaporization, for a percent yield of 77.8%.

Another substrate containing fluvoxamine coated to a film thickness of 4.4 μm was prepared by the same method and heated under an argon atmosphere at 60 V for 8 seconds. The purity of the drug-aerosol particles was determined to be 88%. 6.9 mg was recovered from the glass tube walls after vaporization, for a percent yield of 78.4%.

Example 196

Frovatriptan (MW 379, melting point 102° C., oral dose 2.5 mg), a migraine preparation, was coated on a piece of aluminum foil (20 $cm^2$) according to Method C. The calculated thickness of the drug film was 3.3 μm. The substrate was heated as described in Method C at 60 V for 12 seconds. The purity of the drug-aerosol particles was determined to be 73%. 1.4 mg was recovered from the glass tube walls after vaporization, for a percent yield of 21.2%.

Frovatriptan was further coated on an aluminum foil substrate (24.5 $cm^2$) according to Method G. 5.0 mg of the drug was applied to the substrate, for a calculated thickness of the drug film of 2.0 μm. The substrate was heated substantially as described in Method G at 90 V for 6 seconds, except that two of the openings of the T-shaped tube were left open and the third connected to the 1 L flask. The purity of the drug-aerosol particles was determined to be >91%. 2.8 mg of the drug was found to have aerosolized by mass lost from substrate, for a percent yield of 56%.

Example 197

Hydroxyzine (MW 375, oral dose 50 mg), an antihistamine, was coated on a piece of aluminum foil (20 $cm^2$) according to Method C. The calculated thickness of the drug film was 14 μm. The substrate was heated as described in Method C at 60 V for 9 seconds. The purity of the drug-aerosol particles was determined to be 93%. 5.54 mg was recovered from the glass tube walls after vaporization, for a percent yield of 19.9%.

The same drug coated on an identical substrate (aluminum foil, 20 $cm^2$) to a calculated drug film thickness of 7.6 μm was heated under an argon atmosphere as described in Method C at 60 V for 9 seconds. Purity of the drug-aerosol particles was determined to be 98.6%. 4.31 mg was recovered from the glass tube walls after vaporization, for a percent yield of 28.5%.

The dihydrochloride salt form of the drug was also tested. Hydroxyzine dihydrochloride (MW 448, melting point 193° C., oral dose 50 mg) was coated on a piece of aluminum foil (20 $cm^2$) according to Method C. The calculated thickness of the drug film was 13.7 μm. The substrate was heated as described in Method C at 60 V for 7 seconds. The purity of the drug-aerosol particles was determined to be 41.2%. 0.25 mg was recovered from the glass tube walls after vaporization, for a percent yield of 0.9%.

The salt form of the drug coated on an identical substrate (aluminum foil, 20 $cm^2$) to a calculated drug film thickness of 12.8 μm was heated under an argon atmosphere as described in Method C at 60 V for 7 seconds. Purity of the drug-aerosol particles was determined to be 70.8%. 1.4 mg was recovered from the glass tube walls after vaporization, for a percent yield of 5.5%.

Example 198

Ibutilide was coated on a stainless steel cylinder (8 $cm^2$) according to Method D. 1.436 mg of drug was applied to the substrate, for a calculated drug film thickness of 1.7 μm. The substrate was heated as described in Method D by charging the capacitors to 20.5 V. The purity of the drug-aerosol particles was determined to be 98.4%. 0.555 mg was recovered from the filter after vaporization, for a percent yield of 38.6%. A total mass of 1.374 mg was recovered from the test apparatus and substrate, for a total recovery of 95.7%.

High speed photographs were taken as the drug-coated substrate was heated to monitor visually formation of a thermal vapor. The photographs showed that a thermal vapor was initially visible 25 milliseconds after heating was initiated, with the majority of the thermal vapor formed by 300 milliseconds. Generation of the thermal vapor was complete by 1200 milliseconds.

Example 199

Indomethacin norcholine ester (MW 429, oral dose 25 mg), an analgesic, was coated on a piece of aluminum foil (20 $cm^2$) according to Method C. The calculated thickness of the drug film was 5.1 μm. The substrate was heated as described in Method C at 60 V for 7 seconds. The purity of the drug-aerosol particles was determined to be >99.5%. 2.94 mg was recovered from the glass tube walls after vaporization, for a percent yield of 29.1%.

Example 200

Ketorolac (MW 254, melting point 161° C., oral dose 10 mg), an analgesic, was coated on a piece of aluminum foil (20 $cm^2$) according to Method C. The calculated thickness of the drug film was 1.1 μm. The substrate was heated as described in Method C at 60 V for 6 seconds. The purity of the drug-aerosol particles was determined to be 65.7%. 0.73 mg was recovered from the glass tube walls after vaporization, for a percent yield of 33.2%.

Example 201

Ketorolac norcholine ester (MW 326, oral dose 10 mg), was coated on an aluminum foil substrate (20 $cm^2$) according to Method C. 2.70 mg of drug was applied to the substrate, for a calculated thickness of the drug film of 1.4 μm. The substrate was heated as described in Method C at 60 V for 5 seconds. The purity of the drug-aerosol particles was determined to be 98.5%. 1.1 mg was recovered from the glass tube walls after vaporization, for a percent yield of 40.7%.

Example 202

Levodopa (MW 197, melting point 278° C., oral dose 500 mg), an antiparkinsonian agent, was coated on a piece of aluminum foil (20 $cm^2$) according to Method C. The calculated thickness of the drug film was 3.7 μm. The substrate was heated as described in Method C at 45 V for 15 seconds, then at 30 V for 10 seconds. The purity of the drug-aerosol particles was determined to be 60.6%. The percent yield of the aerosol was 7.2%.

Example 203

Melatonin (MW 232, melting point 118° C., oral dose 3 mg), a dietary supplement, was coated on an aluminum foil substrate (20 cm²) according to Method C. 2.0 mg of drug was applied to the substrate, for a calculated thickness of the drug film of 1.0 µm. The substrate was heated as described in Method C at 90 V for 3.5 seconds. The purity of the drug-aerosol particles was determined to be >99.5%. 0.43 mg was recovered from the glass tube walls after vaporization, for a percent yield of 21.5%.

Another substrate containing melatonin coated to a film thickness of 1.1 µm was prepared by the same method and heated under an argon atmosphere at 90 V for 3.5 seconds. The purity of the drug-aerosol particles was determined to be >99.5%. 1.02 mg was recovered from the glass tube walls after vaporization, for a percent yield of 46.4%.

Example 204

Methotrexate (oral dose 2.5 mg) was coated on a stainless steel cylinder (8 cm²) according to Method D. The calculated thickness of the drug film was 1.3 μm. The substrate was heated as described in Method D by charging the capacitors to 20.5 V. The purity of the drug-aerosol particles was determined to be 66.3%. The percent yield of the aerosol was 2.4%.

Example 205

Methysergide (MW 353, melting point 196° C., oral dose 2 mg), a migraine preparation, was coated on a piece of aluminum foil (20 $cm^2$) according to Method C. The calculated thickness of the drug film was 1.0 μm. The substrate was heated as described in Method C at 90 V for 3.5 seconds. The purity of the drug-aerosol particles was determined to be 67.5%. 0.21 mg was recovered from the glass tube walls after vaporization, for a percent yield of 10.5%.

Example 206

Metoclopramide (MW 300, melting point 148° C., oral dose 10 mg), a gastrointestinal agent, was coated on an aluminum foil substrate (20 $cm^2$) according to Method C. 2.0 mg of drug was applied to the substrate, for a calculated thickness of the drug film of 1.0 μm. The substrate was heated as under an argon atmosphere at 90 V for 3.5 seconds. The purity of the drug-aerosol particles was determined to be 99.1%. 0.43 mg was recovered from the glass tube walls after vaporization, for a percent yield of 21.7%.

Example 207

Nabumetone (MW 228, melting point 80° C., oral dose 1000 mg), an analgesic, was coated on a piece of aluminum foil (20 $cm^2$) according to Method C. The calculated thickness of the drug film was 4.9 μm. The substrate was heated as described in Method C at 60 V for 6 seconds. The purity of the drug-aerosol particles was determined to be >99.5%. 4.8 mg was recovered from the glass tube walls after vaporization, for a percent yield of 49%.

Example 208

Naltrexone (MW 341, melting point 170° C., oral dose 25 mg), an antidote, was coated on an aluminum foil substrate (20 $cm^2$) according to Method C. 10.3 mg of drug was applied to the substrate, for a calculated thickness of the drug film of 5.2 μm. The substrate was heated as described in Method C at 90 V for 5 seconds. The purity of the drug-aerosol particles was determined to be 96%. 3.3 mg was recovered from the glass tube walls after vaporization, for a percent yield of 32%.

Naltrexone was coated on an aluminum foil substrate (20 $cm^2$) according to Method C. 1.8 mg of drug was applied to the substrate, for a calculated thickness of the drug film of 0.9 μm. The substrate was heated as described in Method C at 90 V for 3.5 seconds under an argon atmosphere. The purity of the drug-aerosol particles was determined to be 97.4%. 1.0 mg was recovered from the glass tube walls after vaporization, for a percent yield of 55.6%.

Example 209

Nalmefene (MW 339, melting point 190° C., IV dose 0.5 mg), an antidote, was coated on a metal substrate (50 $cm^2$). 7.90 mg of drug was coated on the substrate, to form a calculated film thickness of 1.6 μm and heated according to Method F to form drug-aerosol particles. Purity of the drug-aerosol particles was determined to be 80%. 2.7 mg was recovered from the glass wool after vaporization, for a percent yield of 34%.

Example 210

Perphenazine (MW 404, melting point 100° C., oral dose 2 mg), a psychotherapeutic agent, was coated on an aluminum foil substrate (20 $cm^2$) according to Method C. 2.1 mg of drug was applied to the substrate, for a calculated thickness of the drug film of 1.1 μm. The substrate was heated as described in Method C at 90 V for 3.5 seconds. The purity of the drug-aerosol particles was determined to be 99.1%. 0.37 mg was recovered from the glass tube walls after vaporization, for a percent yield of 17.6%.

Example 211

Pimozide (MW 462, melting point 218° C., oral dose 10 mg), a psychotherapeutic agent, was coated on a piece of aluminum foil (20 $cm^2$) according to Method C. The calculated thickness of the drug film was 4.9 μm. The substrate was heated as described in Method C at 90 V for 5 seconds. The purity of the drug-aerosol particles was determined to be 79%. The percent yield of the aerosol was 6.5%.

Example 212

Piroxicam (MW 248, melting point 200° C., oral dose 20 mg), a CNS-active steroid was coated on a piece of aluminum foil (20 $cm^2$) according to Method C. The calculated thickness of the drug film was 5.0 μm. The substrate was heated as described in Method C at 60 V for 7 seconds. The purity of the drug-aerosol particles was determined to be 87.7%. 2.74 mg was recovered from the glass tube walls after vaporization, for a percent yield of 27.7%.

Example 213

Pregnanolone (MW 318, melting point 150° C., typical inhalation dose 2 mg), an anesthetic, was coated on a metal substrate (50 $cm^2$). 20.75 mg was coated on the substrate, for a calculated film thickness of 4.2 μm, and heated according to Method F at 300° C. to form drug-aerosol particles. Purity of the drug-aerosol particles was determined to be 87%. 9.96 mg of aerosol particles were collected for a percent yield of 48%).

Example 214

Prochlorperazine 2HCl (MW 446, oral dose 5 mg), a psychotherapeutic agent, was coated on a stainless steel cylinder (8 cm$^2$) according to Method D. 0.653 mg of drug was applied to the substrate, for a calculated drug film thickness of 0.8 µm. The substrate was heated as described in Method D by charging the capacitors to 20.5 V. The purity of the drug-aerosol particles was determined to be 72.4%. 0.24 mg was recovered from the filter after vaporization, for a percent yield of 36.8%. A total mass of 0.457 mg was recovered from the test apparatus and substrate, for a total recovery of 70%.

Example 215

Protriptyline HCl (MW 299, melting point 171° C., oral dose 15 mg), a psychotherapeutic agent, was coated on an aluminum foil substrate (20 cm$^2$) according to Method C. 2.20 mg of drug was applied to the substrate, for a calculated thickness of the drug film of 1.1 µm. The substrate was heated as described in Method C at 90 V for 3.5 seconds. The purity of the drug-aerosol particles was determined to be 99.7%. 0.99 mg was recovered from the glass tube walls after vaporization, for a percent yield of 45.0%.

Example 216

Protriptyline (MW 263, oral dose 15 mg) was coated on an aluminum foil substrate (20 cm$^2$) according to Method C. 5.6 mg of drug was applied to the substrate, for a calculated thickness of the drug film of 2.8 µm. The substrate was heated as described in Method C at 90 V for 3.5 seconds. The purity of the drug-aerosol particles was determined to be 89.8%. 1.4 mg was recovered from the glass tube walls after vaporization, for a percent yield of 25%.

Another substrate containing protriptyline coated to a film thickness of 2.7 µm was prepared by the same method and heated under an argon atmosphere at 90 V for 3.5 seconds. The purity of the drug-aerosol particles was determined to be 90.8%. 1.4 mg was recovered from the glass tube walls after vaporization, for a percent yield of 26.4%.

Example 217

Pyrilamine (MW 285, melting point <25° C., oral dose 25 mg), an antihistamine, was coated on a piece of aluminum foil (20 cm$^2$) according to Method C. The calculated thickness of the drug film was 5.2 µm. The substrate was heated as described in Method C at 60 V for 6 seconds. The purity of the drug-aerosol particles was determined to be 98.4%. 4.3 mg was recovered from the glass tube walls after vaporization, for a percent yield of 41.7%.

Pyrilamine maleate (MW 401, melting point 101° C., oral dose 25 mg), an antihistamine, was coated on a piece of aluminum foil (20 cm$^2$) according to Method C. The calculated thickness of the drug film was 10.8 µm. The substrate was heated as described in Method C at 60 V for 7 seconds. The purity of the drug-aerosol particles was determined to be 93.7%. 10.5 mg was recovered from the glass tube walls after vaporization, for a percent yield of 48.8%.

Example 218

Quinine (MW 324, melting point 177° C., oral dose 260 mg), an anti-infective agent, was coated on a piece of aluminum foil (20 cm$^2$) according to Method C. The calculated thickness of the drug film was 1.1 µm. The substrate was heated as described in Method C at 60 V for 6 seconds. The purity of the drug-aerosol particles was determined to be >99.5%. 0.9 mg was recovered from the glass tube walls after vaporization, for a percent yield of 40.9%.

Example 219

Ramipril (MW 417, melting point 109° C., oral dose 1.25 mg), a cardiovascular agent, was coated on a stainless steel cylinder (8 cm$^2$) and heated to form drug-aerosol particles according to Method D by charging the capacitors to 20.5 V. The purity of the drug-aerosol particles was determined to be 61.5%. 0.27 mg was recovered from the filter after vaporization, for a percent yield of 30%. A total mass of 0.56 mg was recovered from the test apparatus and substrate, for a total recovery of 62.2%.

Example 220

Risperidone (MW 410, melting point 170° C., oral dose 2 mg), a psychotherapeutic agent, was coated on a piece of aluminum foil (20 cm$^2$) according to Method C. The calculated thickness of the drug film was 1.4 µm. The substrate was heated as described in Method C at 90 V for 3.5 seconds. The purity of the drug-aerosol particles was determined to be 79%. The percent yield of the aerosol was 7.9%.

Risperidone was also coated on a stainless steel cylinder (8 cm$^2$). 0.75 mg of drug was manually applied to the substrate, for a calculated drug film thickness of 0.9 µm. The substrate was heated as described in Method D by charging the capacitors to 20.5 V. The purity of the drug-aerosol particles was determined to be 87.3%. The percent yield of aerosol particles was 36.7%. A total mass of 0.44 mg was recovered from the test apparatus and substrate, for a total recovery of 59.5%.

Example 221

Scopolamine (MW 303, melting point <25° C., oral dose 1.5 mg), a gastrointestinal agent, was coated on a metal substrate (50 cm$^2$) according to Method F at 200° C. 37.5 mg of drug was applied to the substrate, for a calculated drug film thickness of 7.5 µm. The substrate was heated according to Method F to form drug-aerosol particles. Purity of the drug-aerosol particles was determined to be 90% by GC analysis. 1.2 mg were recovered for a percent yield of 3.2%.

Example 222

Sotalol (MW 272, oral dose 80 mg), a cardiovascular agent, was coated on a stainless steel cylinder (8 cm$^2$) according to Method D. 1.8 mg of drug was applied to the substrate, for a calculated drug film thickness of 2.3 µm. The substrate was heated as described in Method D by charging the capacitors to 20.5 V. The purity of the drug-aerosol particles was determined to be 96.9%. 0.66 mg was recovered from the filter after vaporization, for a percent yield of 36.7%. A total mass of 1.06 mg was recovered from the test apparatus and substrate, for a total recovery of 58.9%.

High speed photographs were taken as the drug-coated substrate was heated to monitor visually formation of a thermal vapor. The photographs showed that a thermal vapor was initially visible 30 milliseconds after heating was initiated, with the majority of the thermal vapor formed by 90 milliseconds. Generation of the thermal vapor was complete by 500 milliseconds.

Example 223

Sulindac (MW 356, melting point 185° C., oral dose 150 mg), an analgesic, was coated on a piece of aluminum foil (20 cm²) according to Method C. The calculated thickness of the drug film was 4.3 µm. The substrate was heated as described in Method C at 60 V for 8 seconds. The purity of the drug-aerosol particles was determined to be 80.4%. 1.19 mg was recovered from the glass tube walls after vaporization, for a percent yield of 14%.

Example 224

Terfenadine (MW 472, melting point 149° C., oral dose 60 mg), an antihistamine, was coated on a piece of aluminum foil (20 cm²) according to Method C. The calculated thickness of the drug film was 2.5 µm. The substrate was heated as described in Method C at 60 V for 8 seconds. The purity of the drug-aerosol particles was determined to be 75.4%. 0.178 mg was recovered from the glass tube walls after vaporization, for a percent yield of 3.6%.

An identical substrate coated with terfenadine (2.8 µm thick) was heated under an argon atmosphere at 60 V for 8 seconds. The purity of the drug-aerosol particles was determined to be 74.7%. 0.56 mg was recovered from the glass tube walls after vaporization, for a percent yield of 10.2%.

Example 225

Triamcinolone acetonide (MW 434, melting point 294° C., oral dose 0.2 mg), a respiratory agent, was coated on a stainless steel cylinder (6 cm²) according to Method D. 0.2 mg of drug was applied to the substrate, for a calculated drug film thickness of 0.3 µm. The substrate was heated as described in Method D by charging the capacitors to 20.5 V. The purity of the drug-aerosol particles was determined to be 92%. 0.02 mg was recovered from the filter after vaporization, for a percent yield of 10%. A total mass of 0.09 mg was recovered from the test apparatus and substrate, for a total recovery of 45%.

Example 226

Trihexyphenidyl (MW 302, melting point 115° C., oral dose 2 mg), an antiparkinsonian agent, was coated on a piece of aluminum foil (20 cm²) according to Method C. The calculated thickness of the drug film was 1.4 µm. The substrate was heated as described in Method C at 90 V for 3.5 seconds. The purity of the drug-aerosol particles was determined to be 77%. 1.91 mg was recovered from the glass tube walls after vaporization, for a percent yield of 68.2%.

Example 227

Thiothixene (MW 444, melting point 149° C., oral dose 10 mg), a psychotherapeutic agent used as an anti-psychotic, was coated on a piece of aluminum foil (20 cm²) according to Method C. The calculated thickness of the drug film was 1.3 µm. The substrate was heated as described in Method C at 90 V for 3.5 seconds. The purity of the drug-aerosol particles was determined to be 74.0%. 1.25 mg was recovered from the glass tube walls after vaporization, for a percent yield of 48.1%.

Example 228

Telmisartan (MW 515, melting point 263° C., oral dose 40 mg), a cardiovascular agent, was coated on a stainless steel cylinder (8 cm²) according to Method D. 2.73 mg of drug was applied to the substrate, for a calculated drug film thickness of 3.3 µm. The substrate was heated as described in Method D by charging the capacitors to 20.5 V. The purity of the drug-aerosol particles was determined to be 96%. 0.64 mg was recovered from the filter after vaporization, for a percent yield of 23.4%. A total mass of 2.73 mg was recovered from the test apparatus and substrate, for a total recovery of 100%.

High speed photographs were taken as the drug-coated substrate was heated to monitor visually formation of a thermal vapor. The photographs showed that a thermal vapor was initially visible 50 milliseconds after heating was initiated, with the majority of the thermal vapor formed by 400 milliseconds. Generation of the thermal vapor was complete by 1100 milliseconds.

Example 229

Temazepam (MW 301, melting point 121° C., oral dose 7.5 mg), a sedative and hypnotic, was coated on an aluminum foil substrate (20 cm²) according to Method C. 4.50 mg of drug was applied to the substrate, for a calculated thickness of the drug film of 2.3 µm. The substrate was heated as described in Method C at 60 V for 7 seconds. The purity of the drug-aerosol particles was determined to be 97.1%. 1.9 mg was recovered from the glass tube walls after vaporization, for a percent yield of 42.2%.

Example 230

Triamterene (MW 253, melting point 316° C., oral dose 100 mg), a cardiovascular agent, was coated on a stainless steel cylinder (8 cm²) according to Method D. 0.733 mg of drug was applied to the substrate, for a calculated drug film thickness of was 0.9 µm. The substrate was heated as described in Method D by charging the capacitors to 20.5 V. The purity of the drug-aerosol particles was determined to be >99.5%. 0.233 mg was recovered from the filter after vaporization, for a percent yield of 31.8%.

Example 231

Trimipramine (MW 294, melting point 45° C., oral dose 50 mg), a psychotherapeutic agent, was coated on a piece of aluminum foil (20 cm²) according to Method C. The calculated thickness of the drug film was 2.8 µm. The substrate was heated as described in Method C at 90 V for 3.5 seconds. The purity of the drug-aerosol particles was determined to be 99.2%. 2.6 mg was recovered from the glass tube walls after vaporization, for a percent yield of 46.4%.

Example 232

Ziprasidone (MW 413, oral dose 20 mg), an anti-psychotic agent, was coated on a stainless steel cylinder (8 cm²) according to Method D. 0.74 mg of drug was applied to the substrate, for a calculated drug film thickness of 0.9 µm. The substrate was heated as described in Method D by charging the capacitors to 20.5 V. The purity of the drug-aerosol particles was determined to be 87.3%. 0.28 mg was recovered from the filter after vaporization, for a percent yield of 37.8%. A total mass of 0.44 mg was recovered from the test apparatus and substrate, for a total recovery of 59.5%.

Example 233

Zonisamide (MW 212, melting point 163° C., oral dose 75 mg), an anticonvulsant, was coated on a metal substrate and heated to form drug-aerosol particles. The substrate was heated as described in Method C and the purity of the drug-aerosol particles was determined to be 99.7%. The percent yield of the aerosol was 38.3%.

Example 234

Preparation of Drug-Coated Stainless Steel Foil Substrate

Strips of clean 302/304 stainless-steel foil (0.0025 cm thick, Thin Metal Sales) having dimensions 1.5 cm by 7.0 cm were dip-coated with a drug solution. The final coated area was 5.1 cm by 1.5 cm on both sides of the foil, for a total area of 15 cm². Foils were prepared as stated above and then extracted with acetonitrile. The amount of drug was determined from quantitative HPLC analysis. Using the known drug-coated surface area, the thickness was then obtained by:

film thickness (cm)=drug mass (g)/[drug density (g/cm³)×substrate area (cm²)]

If the drug density is not known, a value of 1 g/cm³ is assumed. The film thickness in microns is obtained by multiplying the film thickness in cm by 10,000. After drying, the drug-coated foil was placed into a volatilization chamber constructed of a Delrin® block (the airway) and brass bars, which served as electrodes. The dimensions of the airway were 1.0 high by 5.1 wide by 15.2 cm long. The drug-coated foil was placed into the volatilization chamber such that the drug-coated section was between the two sets of electrodes. After securing the top of the volatilization chamber, the electrodes were connected to three 12V batteries wired in series with a switch controlled by circuit. The circuit was designed to close the switch in pulses so as to resistively heat the foil to a temperature within 50 milliseconds (typically between 320° and 470° C.) and maintain that temperature for up to 3 seconds. The back of the volatilization chamber was connected to a two micron Teflon® filter (Savillex) and filter housing, which were in turn connected to the house vacuum. Sufficient airflow was initiated (typically 30.5 L/min=1.0 m/sec). After the drug had vaporized, airflow was stopped and the Teflon® filter was extracted with acetonitrile. Drug extracted from the filter was analyzed by HPLC UV absorbance at 225 nm using a gradient method aimed at detection of impurities to determine percent purity. Also, the extracted drug was quantified to determine a percent yield, based on the mass of drug initially coated onto the substrate. A percent recovery was determined by quantifying any drug remaining on the substrate, adding this to the quantity of drug recovered in the filter and comparing it to the mass of drug initially coated onto the substrate.

Celecoxib and rizatriptan were tested together according to the method above, by coating a solution of the drug onto a piece of stainless steel foil (15 cm²). Twelve substrates were prepared, with film thicknesses ranging from about 4.4 µm to about 11.4 µm. The substrates were heated as described in the method above to 350° C. Purity of the drug aerosol particles from each substrate was determined. The substrate having a thickness of 4.4 µm was prepared by depositing 0.98 mg of rizatriptan and 5.82 mg of celecoxib. After volatilization of drug this substrate, 0.59 mg of rizatriptan and 4.40 mg of celecoxib were recovered from the filter, for a percent yield of begun. After removal from the hotplate, the vial is allowed to cool to room temperature. The foil is removed, and the vial is extracted with dichloromethane followed by saturated aqueous $NaHCO_3$. The organic and aqueous extracts are shaken together, separated, and the organic extract is dried over $Na_2SO_4$. An aliquot of the organic solution is removed and injected into a reverse-phase HPLC with detection by absorption of 225 nm light. A drug is preferred for aerosolization where the purity of the drug isolated by this method is greater than 85%. Such a drug has a decomposition index less than 0.15. The decomposition index is arrived at by subtracting the drug purity fraction (i.e., 0.85) from 1.

Although the invention has been described with respect to particular embodiments, it will be apparent to those skilled in the art that various changes and modifications can be made without departing from the invention.

It is claimed:

1. A drug supply article comprising:
 a heat-conductive substrate having an impermeable surface;
 a drug composition comprising the drug coated on at least a portion of the surface in the form of a film, wherein said film is a solid having a thickness; and
 a heat source operable to supply heat to the substrate at a rate that achieves a temperature sufficient to vaporize all or a portion of the coated drug composition within a period of 2 seconds;
 wherein the vaporized drug composition comprises a therapeutically effective amount of the drug;
 wherein the film has a thickness between 0.05 and 20 microns;
 wherein the drug is selected from the group consisting of alprazolam, fentanyl, loxapine, prochlorperazine and zaleplon.

2. The drug supply article of claim 1, wherein the drug is in a free base form.

3. The drug supply article of claim 1, wherein the drug is in a salt form.

4. The drug supply article of claim 1, wherein the drug composition comprises only pure drug.

5. The drug supply article of claim 1, wherein the drug composition comprises a pharmaceutically acceptable excipient.

6. The drug supply article of claim 1, wherein the drug is alprazolam.

7. The drug supply article of claim 6, wherein the film thickness is between 1 and 10 microns.

8. The drug supply article of claim 1, wherein the drug is loxapine.

9. The drug supply article of claim 8, wherein the film thickness is between 1 and 20 microns.

10. The drug supply article of claim 1, wherein the drug is prochlorperazine.

11. The drug supply article of claim 10, wherein the film thickness is between 1 and 20 microns.

12. The drug supply article of claim 1, wherein the drug is zaleplon.

13. The drug supply article of claim 12, wherein the film thickness is between 1 and 15 microns.

14. The drug supply article of claim 1, wherein the drug is fentanyl.

15. The drug supply article of claim 14, wherein the film thickness is between 1 and 10 microns.

16. The drug supply article of claim 7, wherein the mass median aerodynamic diameter of the drug composition particles following vaporization is in the range of 0.5 to 3.5 microns.

17. The aerosol drug supply article of claim 16, wherein the mass median aerodynamic diameter of the drug composition particles following vaporization is in the range of 0.5 to 2.0 microns.

18. The drug composition of claim 6, wherein the drug composition particles following vaporization are characterized by less than 2.5% drug degradation products.

19. The drug composition of claim 18, wherein the drug composition particles following vaporization are characterized by less than 1.5% drug degradation products.

20. The drug supply article of claim 9, wherein the mass median aerodynamic diameter of the drug composition particles following vaporization is in the range of 1.0 to 3.5 microns.

21. The drug supply article of claim 20, wherein the mass median aerodynamic diameter of the drug composition particles following vaporization is in the range of 1.5 to 2.5 microns.

22. The drug composition of claim 8, wherein the drug composition particles following vaporization are characterized by less than 2.5% drug degradation products.

23. The drug composition of claim 22, wherein the drug composition particles following vaporization are characterized by less than 1.0% drug degradation products.

24. The drug supply article of claim 11, wherein the mass median aerodynamic diameter of the drug composition particles following vaporization is in the range of 1.0 to 3.5 microns.

25. The drug supply article of claim 24, wherein the mass median aerodynamic diameter of the drug composition particles following vaporization is in the range of 1.5 to 2.5 microns.

26. The drug composition of claim 10, wherein the drug composition particles following vaporization are characterized by less than 5% drug degradation products.

27. The drug composition of claim 26, wherein the drug composition particles following vaporization are characterized by less than 2.5% drug degradation products.

28. The drug supply article of claim 12, wherein the film thickness is between 0.1 and 15 microns.

29. The drug supply article of claim 12, wherein the film thickness is between 1 and 10 microns.

30. The drug supply article of claim 12, wherein the mass median aerodynamic diameter of the drug composition particles following vaporization is in the range of 0.5 to 3.5 microns.

31. The drug supply article of claim 30, wherein the mass median aerodynamic diameter of the drug composition particles following vaporization is in the range of 0.5 to 2.0 microns.

32. The drug composition of claim 12, wherein the drug composition particles following vaporization are characterized by less than 2.5% drug degradation products.

33. The drug supply article of claim 14, wherein the mass median aerodynamic diameter of the drug composition particles following vaporization is in the range of 0.5 to 3.5 microns.

34. The drug supply article of claim 33, wherein the mass median aerodynamic diameter of the drug composition particles following vaporization is in the range of 1.0 to 2.5 microns.

35. The drug composition of claim 14, wherein the drug composition particles following vaporization are characterized by less than 2.5% drug degradation products.

36. The drug composition of claim 35, wherein the drug composition particles following vaporization are characterized by less than 1.0% drug degradation products.

* * * * *